US010400222B2

(12) United States Patent
Bielecka et al.

(10) Patent No.: US 10,400,222 B2
(45) Date of Patent: Sep. 3, 2019

(54) DESATURASE NUCLEIC ACIDS AND POLYPEPTIDES

(71) Applicant: The University of York, York (GB)

(72) Inventors: Monika Bielecka, Wroclaw (PL); Filip Kaminski, York (GB); Thilo Winzer, York (GB); Ian Graham, York (GB)

(73) Assignee: The University of York, York (GB)

( * ) Notice: Subject to any disclaimer, the term of this patent is extended or adjusted under 35 U.S.C. 154(b) by 292 days.

(21) Appl. No.: 15/101,357

(22) PCT Filed: Dec. 8, 2014

(86) PCT No.: PCT/GB2014/053631
§ 371 (c)(1),
(2) Date: Jun. 2, 2016

(87) PCT Pub. No.: WO2015/087058
PCT Pub. Date: Jun. 18, 2015

(65) Prior Publication Data
US 2016/0333324 A1 Nov. 17, 2016

(30) Foreign Application Priority Data

Dec. 10, 2013 (GB) .................................. 1321786.4
Dec. 11, 2013 (GB) .................................. 1321889.6

(51) Int. Cl.
*C12N 15/82* (2006.01)
*C12N 9/02* (2006.01)
*A01H 5/10* (2018.01)
*A01H 5/12* (2018.01)
*A23D 9/00* (2006.01)
*C11B 1/06* (2006.01)

(52) U.S. Cl.
CPC ............. *C12N 9/0071* (2013.01); *A01H 5/10* (2013.01); *A01H 5/12* (2013.01); *A23D 9/00* (2013.01); *C11B 1/06* (2013.01); *C12N 9/0083* (2013.01); *C12N 15/8218* (2013.01); *C12N 15/8247* (2013.01); *C12Y 114/19006* (2013.01)

(58) Field of Classification Search
None
See application file for complete search history.

(56) References Cited

U.S. PATENT DOCUMENTS

| | | | |
|---|---|---|---|
| 6,063,947 A | 5/2000 | DeBonte et al. | |
| 2004/0010819 A1 | 1/2004 | DeBonte et al. | |
| 2007/0214516 A1* | 9/2007 | Fillatti ..................... | A01H 5/10 800/278 |
| 2008/0104732 A1 | 5/2008 | Waterhouse et al. | |
| 2013/0247451 A1* | 9/2013 | Vanhercke ........... | C07K 14/415 44/388 |
| 2013/0288318 A1 | 10/2013 | Wood et al. | |

FOREIGN PATENT DOCUMENTS

| | | |
|---|---|---|
| EP | 0 400 547 A1 | 12/1990 |
| EP | 0 794 250 A1 | 9/1997 |
| EP | 1 944 375 A1 | 7/2008 |
| WO | WO 1997/040698 A1 | 11/1997 |
| WO | WO 2001/079499 A1 | 10/2001 |
| WO | WO 2003/080802 A2 | 10/2003 |
| WO | WO 2006/034059 A1 | 3/2006 |
| WO | WO 2006/079567 A2 | 8/2006 |
| WO | WO 2006/127789 A2 | 11/2006 |
| WO | WO 2011/005998 A1 | 1/2011 |
| WO | WO 2012/166049 A1 | 12/2012 |
| WO | WO 2013/015782 A1 | 1/2013 |

OTHER PUBLICATIONS

Stout et al (The hexanoyl-CoA precursor for cannabinoid biosynthesis is formed by an acyl-activating enzyme in Cannabis sativa trichomes. The Plant Journal 71, 353-365, published online Jun. 1, 2012).*
Porto et al (Fatty acid composition and oxidation stability of hemp (*Cannabis sativa* L.) seed oil extracted by supercritical carbon dioxide. Industrial Crops and Products. 36, 401-404, published online Nov. 29, 2011).*
Van Bakel and Stout et al (JP482051, published Oct. 28, 2011).*
Pham et al (Mutant alleles of FAD2-1A and FAD2-1B combine to produce soybeans with the high oleic acid seed oil trait. BMC Plant Biology, 10:195, 2010).*
Accession No. JP482051, Oct. 28, 2011.
Accession No. EXB29003, Jun. 27, 2013.
Belide et al., "Modification of Seed Oil Composition in *Arabidopsis* by Artificial MicroRNA-Mediated Gene Silencing," *Front Plant Sci.* 3:168, 2012 (6 pages).
Bielecka et al., "Targeted Mutation of Δ12 and DΔ15 Desaturase Genes in Hemp Produce Major Alternations in Seed Fatty Acid Composition Including a High Oleic Hemp Oil," *Plant Biotechnol J.* 12:613-623, 2014.
Callaway et al., "Occurrence of 'omega-3' Stearidonic Acid (cis-6,9,12,15-octadecatetraenoic Acid in Hemp (*Cannabis sativa* L.) Seed," *J Intl Hemp Assoc.* 3:61-63, 1996.
Chapman et al., "Transgenic Cotton Plants with Increased Seed Oleic Acid Content," *J Am Oil Chem Soc.* 78:941-947, 2001.
Leizer et al., "The Composition of Hemp Seed Oil and Its Potential as an Important Source of Nutrition," *J. Nutraceuticals* 2:35-53, 2000.
Sunilkumar et al., "A Comprehensive Study of the Use of a Homologous Promoter in Antisense Cotton Lines Exhibiting a High Seed Oleic Acid Phenotype," *Plant Biotechnol J.* 3:319-330, 2005.
Qu et al., "Development of Marker-Free Transgenic *Jatropha* Plants with Increased Levels of Seed Oleic Acid" *Biotechnol. Biofuels* 5:10, 2012 (11 pages).

(Continued)

*Primary Examiner* — Medina A Ibrahim
*Assistant Examiner* — Wayne Zhong
(74) *Attorney, Agent, or Firm* — Klarquist Sparkman, LLP

(57) ABSTRACT

The disclosure relates to delta (12) and delta (15) desaturases and their use in the modification of oil content in hemp.

12 Claims, 20 Drawing Sheets

Specification includes a Sequence Listing.

(56) References Cited

OTHER PUBLICATIONS

Great Britain Application No. 1321786.4 Search Report dated Aug. 21, 2014 (5 pages).
PCT/GB2014/053631 International Search Report and Written Opinion dated Apr. 2, 2015 (16 pages).

\* cited by examiner

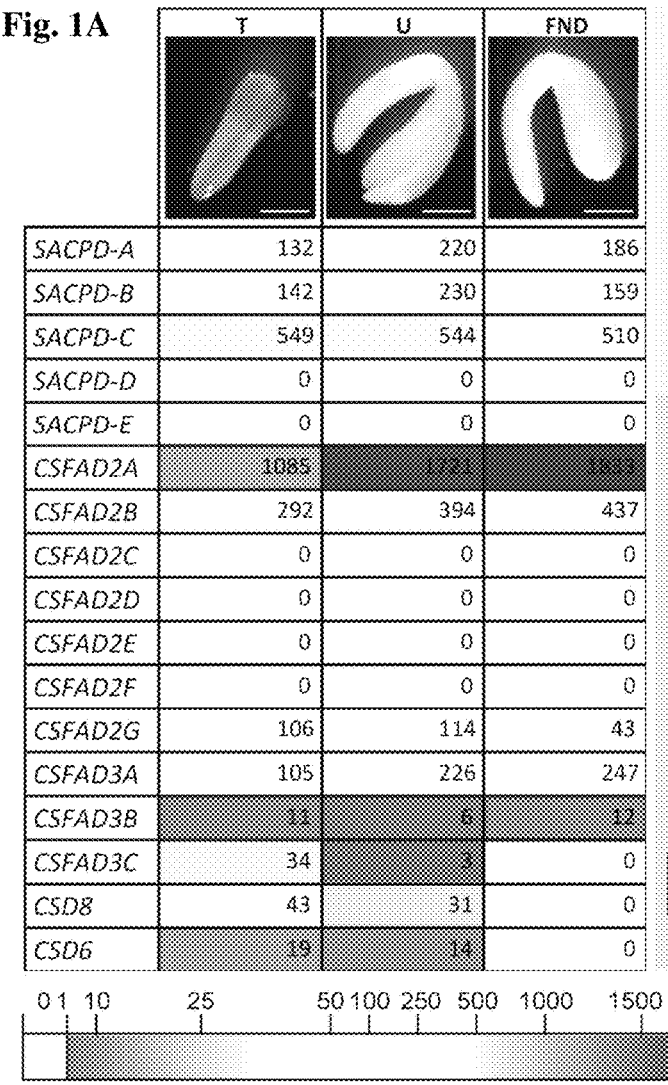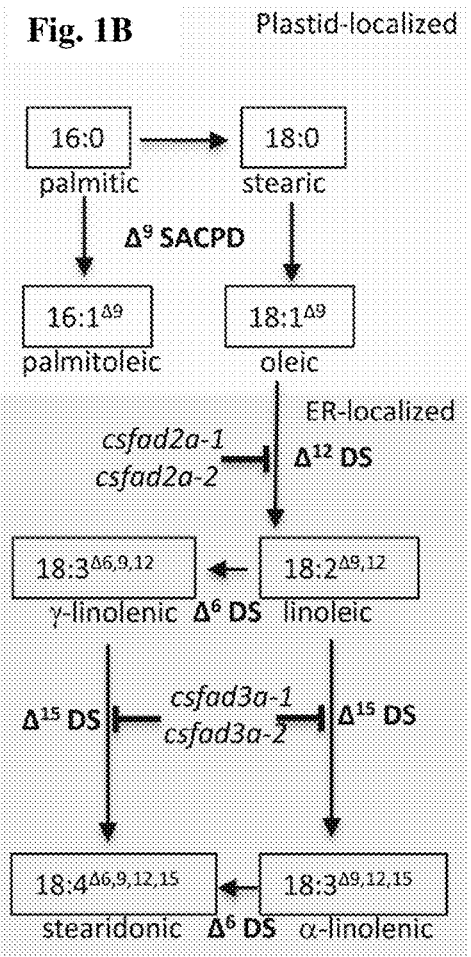
Fig. 1A
Fig. 1B

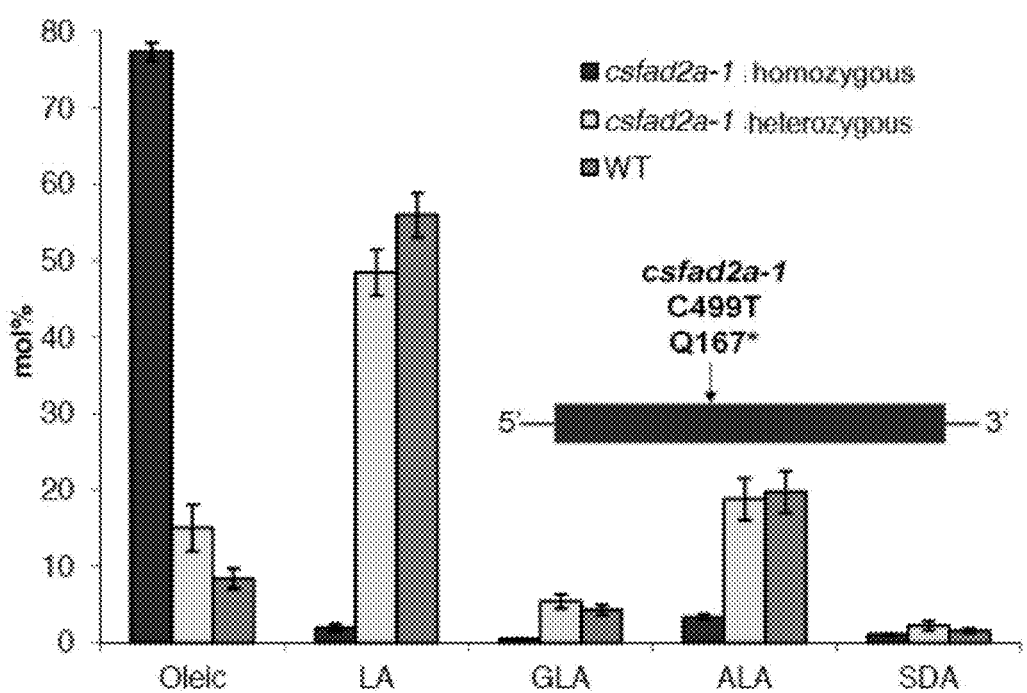
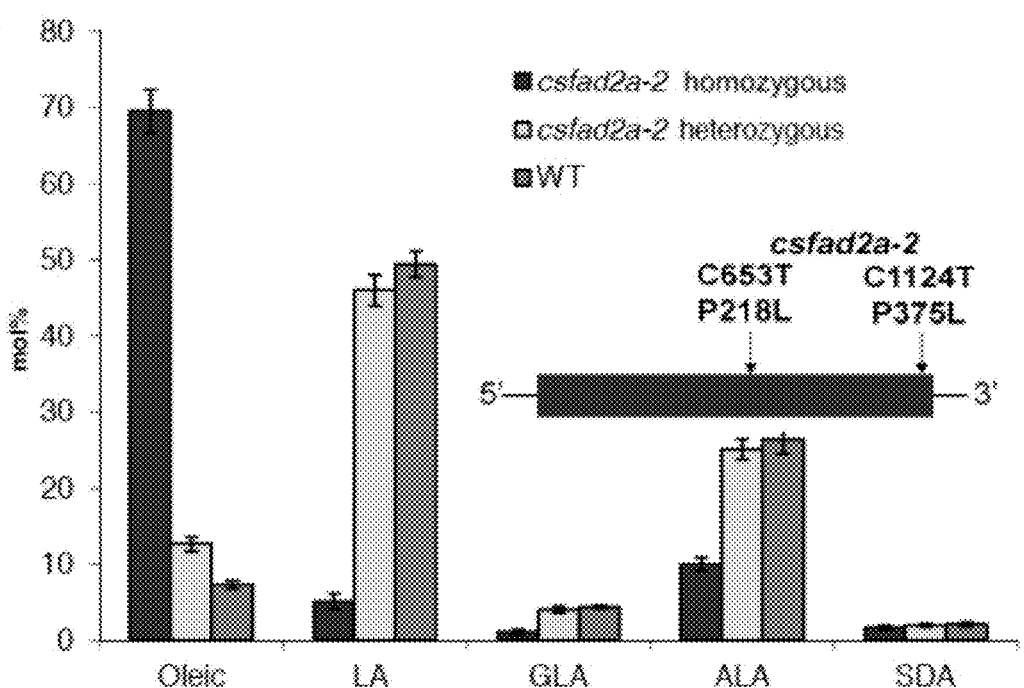

Fig. 12

CSFAD2A; nucleotide sequence (SEQ ID 1)

ATGGGAGCCGGTGGCCGAATGCCCGAGGCGAAATCCGAGTTGAATGGTAGTAAGAATAATAATAGGCTA
ATTGAGAGAGTACCACACACCAAACCACCATTCACATTAAGCGAAATCAAGAAAGCAATTCCGCCCCATTG
CTTTAAACGCTCTCTAATTCGCTCTTTTGCTTGTGTCTTTCACGACCTTTTTTCGCGTCATTGTTTTACTATG
TTGCAACCTCTTACTTTCACCTTATCCCGAAACCAATTTCATACATTGCTTGGCCAATTTATTGGATTTTCCA
AGGTTGTATTTTGACCGGGGTTTGGGTCATCGCTCATGAGTGTGGTCACCATGCTTTTAGTGACCACCAGT
GGGTGGATGACACCGTTGGTCTCATCCTCCACTCTGCTCTTCTTGTCCCATATTTTTCATGGAAGTATAGTC
ATCGTCGCCACCACTCAAACACGGGGTCCATTGATCGCGACGAAGTGTTTGTACCAAAACCAAAATCACA
AGTGTCACCATTCGCCAAATACTTAAACAATCCACCCGGGAGAGTCTTAAGCCTTTTTGTTACCCTAACACT
TGGTTGGCCTTTGTACTTAGCTTTCAATGTATCAGGCAGACCATATGACCGTTTCGCTTGTCATTATGATCC
CTATGGCCCAATCTACTCAAACCGCGAAAGGTTACAAATATTCATCTCGGACATAGGGATTTTCATTGCCA
CATTCGCGCTATACCACCTTGTCTCGGCCAAAGGGTTAGGTTGGGTTGTGTTAGTGTATGGTGTGCCTTTG
TTAATAGTAAATGGCTTCCTTGTTTTGATCACTTACTTGCAACACACTCACCCTGCATTGCCTCATTATGACT
CGTCCGAATGGGATTGGTTGAGAGGAGCATTGTCAACCGTTGATCGAGACTATGGAATTCTCAATAGGGT
TTTTCACAACATTACTGACACTCATGTTGTGCACCATTTATTCTCAACAATGCCACATTACAATGCAATGGA
AGCAACCAAAGCTGTGAAGCCGATATTAGGCGAGTACTACCGTTTAGATGACACTCCAATTGTTAAGGCT
ATGTGGAGAGAAGCTAAAGAGTGTCTCTATGTTGAGCAAGATGATGATTCTCCATCTAACAAGGTGTTT
TTTGGTACAAAAACAAGTTTTAG

Fig. 13

CSFAD2A; amino acid sequence (SEQ ID 3)

MGAGGRMPEAKSELNGSKNNNRLIERVPHTKPPFTLSEIKKAIPPHCFKRSLIRSFACVFHDLFFASLFYYVATSY
FHLIPKPISYIAWPIYWIFQGCILTGVWVIAHECGHHAFSDHQWVDDTVGLILHSALLVPYFSWKYSHRRHHSN
TGSIDRDEVFVPKPKSQVSPFAKYLNNPPGRVLSLFVTLTLGWPLYLAFNVSGRPYDRFACHYDPYGPIYSNRER
LQIFISDIGIFIATFALYHLVSAKGLGWVVLVYGVPLLIVNGFLVLITYLQHTHPALPHYDSSEWDWLRGALSTVD
RDYGILNRVFHNITDTHVVHHLFSTMPHYNAMEATKAVKPILGEYYRLDDTPIVKAMWREAKECLYVEQDDD
SPSNKGVFWYKNKF

Fig. 14

CSFAD3A; nucleotide sequence (SEQ ID 2)

ATGACAGAATCACATGCTTCGGAGGAAATGGCGAGAGAAGAAAAAGGTGACTACCCCATTAAGGTGGCA
AATGGGATCCGAAACCAAAACGGCGATTTCGATCTGAGTGATCCTCCACCGTTTAAGATAGCTGAGATCC
GAGCCGCCATTCCTAAGCATTGTTGGGTTAAGAATCCATGGCGCTCACTCAGCTATGTTTTCAGAGATCTC
TTTATCATTTTTGCATTGGCCTTTGCCGCTTTCTATTCCGATACTTGGGTCGTTTGGCCATTTTACTGGGCTG
CTCAAGGAACCATGTTCTGGGCTCTCTTCGTTCTCGGCCACGATTGTGGCCATGGAAGCTTTTCAAACAGT
CCTGAGCTGAATAGCGCTGTGGGTCATATTCTGCATTCTGCAATCCTTGTACCTTACAATGGATGGAGAAT
TAGCCATAGAACTCATCATCAAAACCATGGCCATGTTGAGAATGACGAGTCATGGGTTCCGTTGACTGAG
AAGATGTACAAACAGTTGGATGAGAAAACAAAGAGGCTGAGATTCAAAGTCCCATTTCCCTTATTTGCAT
ACCCTTTTTATCTGTGGAATAGAAGTCCAGGAAAAGAGGGCTCTCATTTCAATCCTTACAGCAAATTATTTA
CTCCAAGTGAGAGAAACCAAATAATAACTTCAACGGTTTGCTGGTCAACAATGGCTGCTTTGCTTGTCTGT
TTGTCCTTCATAGTAGGTCCTGTTCAAGTTCTCATGCTGTATGTTGTTCCTTATTGGATATTTGTGATGTGGC
TAGACATTGTCACTTACTTGCATCACCATGGTTATGAGCAAAAACTCCCTTGGTACCGGGGCAAGGAATGG
AGTTACCTAAGGGGAGGGCTAACAACAGTAGACCGTGACTATGGAATATTTAACAATATCCACCATGACA
TTGGAACTCATGTTATACACCATCTCTTCCCTCAAATCCCACACTACCATCTTGTGGAAGCTACCAAGGCAG
CCAAGCCAGTGCTCGGAAAGTATTACAGGGAGCCTAGAAAGTCAGGGCCAATTCCAGTCCACTTGATCGA
GAATCTAGTTAAGAGCATCAGCCAGGACCACTACGTGAGTGACAATGGCGAAGTAGTATACTACCAGACA
GACCCAGAACTTAATAATAATAATAATAAAAAAATATCTGAGGCCAAGCAAATGTAG

Fig. 15

CSFAD3A; Protein Sequence (SEQ ID 4)

MTESHASEEMAREEKGDYPIKVANGIRNQNGDFDLSDPPPFKIAEIRAAIPKHCWVKNPWRSLSYVFRDLFIIF
ALAFAAFYSDTWVVWPFYWAAQGTMFWALFVLGHDCGHGSFSNSPELNSAVGHILHSAILVPYNGWRISHR
THHQNHGHVENDESWVPLTEKMYKQLDEKTKRLRFKVPFPLFAYPFYLWNRSPGKEGSHFNPYSKLFTPSERN
QIITSTVCWSTMAALLVCLSFIVGPVQVLMLYVVPYWIFVMWLDIVTYLHHHGYEQKLPWYRGKEWSYLRGG
LTTVDRDYGIFNNIHHDIGTHVIHHLFPQIPHYHLVEATKAAKPVLGKYYREPRKSGPIPVHLIENLVKSISQDHYV
SDNGEVVYYQTDPELNNNNNKKISEAKQM

SEQUENCE LISTING

```
<160> NUMBER OF SEQ ID NOS: 50

<210> SEQ ID NO 1
<211> LENGTH: 1164
<212> TYPE: DNA
<213> ORGANISM: Cannabis sativa

<400> SEQUENCE: 1
atgggagccg gtggccgaat gcccgaggcg aaatccgagt tgaatggtag taagaataat      60
aataggctaa ttgagagagt accacacacc aaaccaccat tcacattaag cgaaatcaag     120
aaagcaattc cgcccattg ctttaaacgc tctctaattc gctcttttgc ttgtgtcttt      180
cacgaccttt ttttcgcgtc attgttttac tatgttgcaa cctcttactt tcaccttatc     240
ccgaaaccaa tttcatacat tgcttggcca atttattgga ttttccaagg ttgtattttg     300
accggggttt gggtcatcgc tcatgagtgt ggtcaccatg cttttagtga ccaccagtgg     360
```

```
gtggatgaca ccgttggtct catcctccac tctgctcttc ttgtcccata ttttttcatgg    420 aagtatagtc atcgtcgcca ccactcaaac acggggtcca ttgatcgcga cgaagtgttt    480
gtaccaaaac caaaatcaca agtgtcacca ttcgccaaat acttaaacaa tccacccggg    540
agagtcttaa gccttttgt taccctaaca cttggttggc ctttgtactt agctttcaat    600
gtatcaggca gaccatatga ccgtttcgct tgtcattatg atccctatgg cccaatctac    660
tcaaaccgcg aaaggttaca aatattcatc tcggacatag ggattttcat tgccacattc    720
gcgctatacc accttgtctc ggccaaaggg ttaggttggg ttgtgttagt gtatggtgtg    780
cctttgttaa tagtaaatgg cttccttgtt ttgatcactt acttgcaaca cactcacccct    840 gcattgcctc attatgactc gtccgaatgg gattggttga gaggagcatt gtcaaccgtt    900
gatcgagact atggaattct caatagggtt tttcacaaca ttactgacac tcatgttgtg    960
caccatttat tctcaacaat gccacattac aatgcaatgg aagcaaccaa agctgtgaag   1020
ccgatattag gcgagtacta ccgtttagat gacactccaa ttgttaaggc tatgtggaga   1080
gaagctaaag agtgtctcta tgttgagcaa gatgatgatt ctccatctaa caaaggtgtt   1140
ttttggtaca aaaacaagtt ttag                                           1164
```

<210> SEQ ID NO 2
<211> LENGTH: 1191
<212> TYPE: DNA
<213> ORGANISM: Cannabis sativa

<400> SEQUENCE: 2

```
atgacagaat cacatgcttc ggaggaaatg gcgagagaag aaaaaggtga ctacccccatt     60 aaggtggcaa atgggatccg aaaccaaaac ggcgatttcg atctgagtga tcctccaccg    120
tttaagatag ctgagatccg agccgccatt cctaagcatt gttgggttaa gaatccatgg    180
cgctcactca gctatgtttt cagagatctc tttatcattt ttgcattggc ctttgccgct    240
ttctattccg atacttgggt cgtttggcca ttttactggg ctgctcaagg aaccatgttc    300
tgggctctct tcgttctcgg ccacgattgt ggccatggaa gcttttcaaa cagtcctgag    360
ctgaatagcg ctgtgggtca tattctgcat tctgcaatcc ttgtacctta caatggatgg    420
agaattagcc atagaactca tcatcaaaac catggccatg ttgagaatga cgagtcatgg    480
gttccgttga ctgagaagat gtacaaacag ttggatgaga aaacaaagag gctgagattc    540
aaagtcccat ttcccttatt tgcataccct ttttatctgt ggaatagaag tccaggaaaa    600
gagggctctc atttcaatcc ttacagcaaa ttatttactc caagtgagag aaaccaaata    660
ataacttcaa cggtttgctg gtcaacaatg gctgctttgc ttgtctgttt gtccttcata    720
gtaggtcctg ttcaagttct catgctgtat gttgttcctt attggatatt tgtgatgtgg    780
ctagacattg tcacttactt gcatcaccat ggttatgagc aaaaactccc ttggtaccgg    840
ggcaaggaat ggagttacct aaggggaggg ctaacaacag tagaccgtga ctatggaata    900
tttaacaata tccaccatga cattggaact catgttatac accatctctt ccctcaaatc    960
ccacactacc atcttgtgga agctaccaag gcagccaagc cagtgctcgg aaagtattac   1020
agggagccta gaaagtcagg gccaattcca gtccacttga tcgagaatct agttaagagc   1080
atcagccagg accactacgt gagtgacaat ggcgaagtag tatactacca gacagaccca   1140
gaacttaata taataataa taaaaaaata tctgaggcca agcaaatgta g              1191
```

<210> SEQ ID NO 3
<211> LENGTH: 387

<212> TYPE: PRT
<213> ORGANISM: Cannabis sativa

<400> SEQUENCE: 3

```
Met Gly Ala Gly Gly Arg Met Pro Glu Ala Lys Ser Glu Leu Asn Gly
1               5                   10                  15

Ser Lys Asn Asn Asn Arg Leu Ile Glu Arg Val Pro His Thr Lys Pro
            20                  25                  30

Pro Phe Thr Leu Ser Glu Ile Lys Lys Ala Ile Pro Pro His Cys Phe
        35                  40                  45

Lys Arg Ser Leu Ile Arg Ser Phe Ala Cys Val Phe His Asp Leu Phe
    50                  55                  60

Phe Ala Ser Leu Phe Tyr Tyr Val Ala Thr Ser Tyr Phe His Leu Ile
65                  70                  75                  80

Pro Lys Pro Ile Ser Tyr Ile Ala Trp Pro Ile Tyr Trp Ile Phe Gln
                85                  90                  95

Gly Cys Ile Leu Thr Gly Val Trp Val Ile Ala His Glu Cys Gly His
            100                 105                 110

His Ala Phe Ser Asp His Gln Trp Val Asp Asp Thr Val Gly Leu Ile
        115                 120                 125

Leu His Ser Ala Leu Leu Val Pro Tyr Phe Ser Trp Lys Tyr Ser His
    130                 135                 140

Arg Arg His His Ser Asn Thr Gly Ser Ile Asp Arg Asp Glu Val Phe
145                 150                 155                 160

Val Pro Lys Pro Lys Ser Gln Val Ser Pro Phe Ala Lys Tyr Leu Asn
                165                 170                 175

Asn Pro Pro Gly Arg Val Leu Ser Leu Phe Val Thr Leu Thr Leu Gly
            180                 185                 190

Trp Pro Leu Tyr Leu Ala Phe Asn Val Ser Gly Arg Pro Tyr Asp Arg
        195                 200                 205

Phe Ala Cys His Tyr Asp Pro Tyr Gly Pro Ile Tyr Ser Asn Arg Glu
    210                 215                 220

Arg Leu Gln Ile Phe Ile Ser Asp Ile Gly Ile Phe Ile Ala Thr Phe
225                 230                 235                 240

Ala Leu Tyr His Leu Val Ser Ala Lys Gly Leu Gly Trp Val Val Leu
                245                 250                 255

Val Tyr Gly Val Pro Leu Leu Ile Val Asn Gly Phe Leu Val Leu Ile
            260                 265                 270

Thr Tyr Leu Gln His Thr His Pro Ala Leu Pro His Tyr Asp Ser Ser
        275                 280                 285

Glu Trp Asp Trp Leu Arg Gly Ala Leu Ser Thr Val Asp Arg Asp Tyr
    290                 295                 300

Gly Ile Leu Asn Arg Val Phe His Asn Ile Thr Asp Thr His Val Val
305                 310                 315                 320

His His Leu Phe Ser Thr Met Pro His Tyr Asn Ala Met Glu Ala Thr
                325                 330                 335

Lys Ala Val Lys Pro Ile Leu Gly Glu Tyr Tyr Arg Leu Asp Asp Thr
            340                 345                 350

Pro Ile Val Lys Ala Met Trp Arg Glu Ala Lys Glu Cys Leu Tyr Val
        355                 360                 365

Glu Gln Asp Asp Asp Ser Pro Ser Asn Lys Gly Val Phe Trp Tyr Lys
    370                 375                 380

Asn Lys Phe
385
```

<210> SEQ ID NO 4
<211> LENGTH: 396
<212> TYPE: PRT
<213> ORGANISM: Cannabis sativa

<400> SEQUENCE: 4

```
Met Thr Glu Ser His Ala Ser Glu Glu Met Ala Arg Glu Glu Lys Gly
1               5                   10                  15

Asp Tyr Pro Ile Lys Val Ala Asn Gly Ile Arg Asn Gln Asn Gly Asp
            20                  25                  30

Phe Asp Leu Ser Asp Pro Pro Phe Lys Ile Ala Glu Ile Arg Ala
        35                  40                  45

Ala Ile Pro Lys His Cys Trp Val Lys Asn Pro Trp Arg Ser Leu Ser
    50                  55                  60

Tyr Val Phe Arg Asp Leu Phe Ile Ile Phe Ala Leu Ala Phe Ala Ala
65                  70                  75                  80

Phe Tyr Ser Asp Thr Trp Val Val Trp Pro Phe Tyr Trp Ala Ala Gln
            85                  90                  95

Gly Thr Met Phe Trp Ala Leu Phe Val Leu Gly His Asp Cys Gly His
            100                 105                 110

Gly Ser Phe Ser Asn Ser Pro Glu Leu Asn Ser Ala Val Gly His Ile
        115                 120                 125

Leu His Ser Ala Ile Leu Val Pro Tyr Asn Gly Trp Arg Ile Ser His
    130                 135                 140

Arg Thr His His Gln Asn His Gly His Val Glu Asn Asp Glu Ser Trp
145                 150                 155                 160

Val Pro Leu Thr Glu Lys Met Tyr Lys Gln Leu Asp Glu Lys Thr Lys
                165                 170                 175

Arg Leu Arg Phe Lys Val Pro Phe Pro Leu Phe Ala Tyr Pro Phe Tyr
            180                 185                 190

Leu Trp Asn Arg Ser Pro Gly Lys Glu Gly Ser His Phe Asn Pro Tyr
        195                 200                 205

Ser Lys Leu Phe Thr Pro Ser Glu Arg Asn Gln Ile Ile Thr Ser Thr
    210                 215                 220

Val Cys Trp Ser Thr Met Ala Ala Leu Leu Val Cys Leu Ser Phe Ile
225                 230                 235                 240

Val Gly Pro Val Gln Val Leu Met Leu Tyr Val Pro Tyr Trp Ile
                245                 250                 255

Phe Val Met Trp Leu Asp Ile Val Thr Tyr Leu His His Gly Tyr
            260                 265                 270

Glu Gln Lys Leu Pro Trp Tyr Arg Gly Lys Glu Trp Ser Tyr Leu Arg
        275                 280                 285

Gly Gly Leu Thr Thr Val Asp Arg Asp Tyr Gly Ile Phe Asn Asn Ile
    290                 295                 300

His His Asp Ile Gly Thr His Val Ile His His Leu Phe Pro Gln Ile
305                 310                 315                 320

Pro His Tyr His Leu Val Glu Ala Thr Lys Ala Ala Lys Pro Val Leu
                325                 330                 335

Gly Lys Tyr Tyr Arg Glu Pro Arg Lys Ser Gly Pro Ile Pro Val His
            340                 345                 350

Leu Ile Glu Asn Leu Val Lys Ser Ile Ser Gln Asp His Tyr Val Ser
        355                 360                 365

Asp Asn Gly Glu Val Val Tyr Tyr Gln Thr Asp Pro Glu Leu Asn Asn
```

Asn Asn Asn Lys Lys Ile Ser Glu Ala Lys Gln Met
385              390              395

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
aaaatgggag ccggtggccg aat                                           23

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
gggcggaatt gctttcttga tttcgc                                        26

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
gcagacgata tgaccgtttc gcttctca                                      28

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
gcgagttggt acaacacgaa tgtggtga                                      28

<210> SEQ ID NO 9
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t

<400> SEQUENCE: 9
acncaycayc araaycaygg                                               20

<210> SEQ ID NO 10
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)

```
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 10
caytgyttnc cnckrtacca                                               20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ggcgattcct aagcactgtt g                                             21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tcaccagtgt cgctgacgta a                                             21

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cacggccatg ttgagaatga cgag                                          24

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
ggacaaacag acaagcaaag cagcca                                        26

<210> SEQ ID NO 15
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(39)
<223> OTHER INFORMATION: R=A or G; V=A, C or G; N=A/T or C/G

<400> SEQUENCE: 15
attctagatc cracatgttt tttttttttt tttttttvn                          39

<210> SEQ ID NO 16
<211> LENGTH: 23
<212> TYPE: DNA
<213> ORGANISM: Artificial Sequence
```

```
<220> FEATURE:
<223> OTHER INFORMATION: Primer

<400> SEQUENCE: 16
ctcggacata gggattttca ttg                                              23

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
caacccaacc taaccctttg g                                                21

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
tcaaatccca cactaccatc ttgt                                             24

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
tttctaggct ccctgtaata ctttcc                                           26

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gggtcacact gtgccaatct ac                                               22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cccagcaagg tcaagacgaa                                                  20

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
cccattgctt taaacgctct ctaattcgct                                       30
```

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
cacccctaac cacattaagc catacccat                               30

<210> SEQ ID NO 24
<211> LENGTH: 42
<212> TYPE: DNA
<213> ORGANISM: Artificial Sequence
<220> FEATURE:
<223> OTHER INFORMATION: Primer

<400> SEQUENCE: 24
tgtaaaacga cggccagtgg gctgctcaag gaaccatgtt ct                42

<210> SEQ ID NO 25
<211> LENGTH: 42
<212> TYPE: DNA
<213> ORGANISM: Artificial Sequence
<220> FEATURE:
<223> OTHER INFORMATION: Primer

<400> SEQUENCE: 25
aggaaacagc tatgaccatc cttggtagct tccacaagat gg                42

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
ataggatcca aaatgggagc cggt                                    24

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
gcctcgagcc taaaacttgt ttttgtacc                               29

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
ggggaattca taatgacaga atcacatgc                               29

<210> SEQ ID NO 29
<211> LENGTH: 28
<212> TYPE: DNA
<213> ORGANISM: Artificial Sequence
<220> FEATURE:
<223> OTHER INFORMATION: Primer

```
<400> SEQUENCE: 29
tagcggccgc atactacatt tgcttggc                                          28

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
ataggatcca aatgggagc cggt                                                24

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
gcctcgagcc taaaacttgt ttttgtacc                                          29

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
ggggaattca taatgacaga atcacatgc                                          29

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
tagcggccgc atactacatt tgcttggc                                          28

<210> SEQ ID NO 34
<211> LENGTH: 1191
<212> TYPE: DNA
<213> ORGANISM: Cannabis sativa

<400> SEQUENCE: 34
atggctctca aactcaaccc caccatcgct caatctccaa agttaccagc ttttgctctt        60
ccaccaatgg ctagcctcag atctcccaag ttcttcatgg cctccaccct ccgttctggc      120
tccaaagagg ttgataatat caagaagcct tcactcctc ctagagagt ccatgttcaa        180 gtaacacatt ccatgccacc tcagaagatt gagatcttta gtcattgga agattgggct      240 gatcagaacc ttttggttca ccttaagcca gttgagaagt gctggcaacc tcaggatttt      300
ctccctgaac catcatctga tgatttcat gagcaggtga tggaacttag ggagagggct      360
agggagcttc ctgatgatta ctttgttgtt ctggttggtg atatgatcac agaagaagca      420
ctcccaactt atcaaactat gcttaataca ttggatggag ttaggatga aactggtgcc      480 agcccaactt cttgggctat ttggactaga gcatggactg ctgaagagaa caggcatggt      540
```

```
gacctcctca acaagtatct ttacctcagt ggacgagtcg atatgaggca aattgagaag      600
accattcagt atctgatcgg ttctggaatg gatccccgga cagagaacaa tccttatctt      660
ggtttcatct acacttcatt ccaagaaaga gccaccttta tctcacatgg taacactgcc      720
aggctagcaa aggagcatgg ggacttaaaa ttggcacaaa tatgtggtac catagctgca      780
gacgagaagc gccacgagac agcctacact aagatagttg agaagctatt tgagattgat      840
cctgatggga ctgtgttagc atttgctgac atgatgagga agaagatagc catgccagca      900
cacttgatgt acgatggccg agatgacaat cttttcgata acttttctgc tgttgcacaa      960
cggcttggag tgtacacggc caaggattac gcggacatat ggagttcttg gttgggagg      1020
tggaaggtgg agaagctaag tggactttcc ggggaggggc ttaaggctca ggagtatgtt     1080
tgcgggttac ctccaagaat cagaaggctg gaggaaagag ctcaaggaag ggtgaaacaa     1140
gctaggagtg tacccttcag ttgggtatat gatagacaag tgagtctcta a              1191

<210> SEQ ID NO 35
<211> LENGTH: 1182
<212> TYPE: DNA
<213> ORGANISM: Cannabis sativa

<400> SEQUENCE: 35
atggctctca gactcagctc aacgatcaac ttcccaactc acaacgtctc ttctaagcct       60
cacactctca gatctccaag gctctgcatg gcctccactc tccactccat ttctaaagag      120
actgaaaatg gaaaaaagcc ttattcgcct ccgaaggagg tacatcttca agtgactcat      180
tcactaccac ctcaaaaggt tgagatcttc aagtcattag aaggctgggc tgaagataac      240
attttggtgc acttgaaacc tgtggagaaa tgttggcagc acaagatttt ctacccgag       300
ccggaatctg aagggtttta tgatcaagtc agggagttaa gggaaagggc gaaagaaatt      360
cccgatgact attttgttgc gttggtcggt gatatgatca ctgaagaagc tctaccgaca      420
taccagacaa tgcttaatac tttagacggg gttagagatg agaccggtgc aagccctact      480
tcttggggaa tatggaccag ggcgtggact gctgaggaga ataggcatgg agaccttctc      540
aacaagtatc tgtatctctc tggaagggtt gatatgaagc aagttgagaa gaccatccaa      600
tatctcattg gctcaggaat ggatcccaaa acggaaaaca acccgtattt gggtttcatc      660
tacacctcct tcaagagag gctacattc atctcccatg gaaatactgc caggcaagcc       720
aaagagcacg gtgacctgaa actggcgcag atatgcggca caattgctgc cgatgagaaa      780
cgccatgaaa ctgcctacac aaagattgtg gagaagctct ttgagattga cccgaatggc      840
actgttatgg ctttгtgctga catgatgaag aagaagatat cgatgcctgc ccacttgatg      900
tacgacggga aggatgacaa tcttttcgat cactttgcag cagttacaca gaagcttgaa      960
gtttacactg ccaaggatta tgctgatatc atggagtttc tggttggaag atggaagatt     1020
gagaaattga gtggtctttc gagtgagggc cacagagcac aagattatgt gtgtaaattg     1080
ccccagagga taagaaagtt ggaggagaga gctcaggaa ggaccaagca agcatcaatg      1140
gttcctttca gctggatatt tggtagagaa atcaagattt ga                        1182

<210> SEQ ID NO 36
<211> LENGTH: 1173
<212> TYPE: DNA
<213> ORGANISM: Cannabis sativa

<400> SEQUENCE: 36
atgcacgcag gagcctcctc ttcttacctt agaaatcttc aatgggccca acccaacggc       60
```

```
ccaataagcc caaaaacact cccactgaac ccctacgtca gtttccgagt ctccgccgtg      120
gcagccccac cgccgcagct aaagtttcag agaacgcatt cgatgccgcc agagaaagtt      180
gaaatcttta agtcgttaga aggttgggcc tccaaatctg ttctgccatt gttgaagccc      240
gtggaccaat gctggcagcc tcaagatttt ttacccgacc cggctaagac tagagaagag      300
ttctttgatc aggtccgtca attgcgtgat cggacggtcg agcttccaga tgagttttc       360 gttgtgttag ttggggatat gatcacggag gacgcattgc ctacgtacca gaccatgata      420 aatacccctgg acggcgttaa ggacgagacc ggagctagct caagcccatg ggcccaatgg     480
actcgggcct ggaccgccga agagaatcgc acggtgatt tgcttcgaac ttatctgtat       540
ttaacgggtc gggtcgatat gaccatgatc gaaagaaccg tccagtacct gattggagct      600
ggcatggatc cgggaacaga gaacagtccg tacttgggat tgtgtacac gtcattccaa       660 gaacgtgcca cgtttgtgtc acatggcaac acagcacgca tggcaaagga gagcggggat     720
ccagtgttgg cgcgtatatg cgggaccatt gcatccgacg agaaacgcca cgagaatgcc     780
tattccaaga tcgttgagaa gcttctagaa gtggacccca acaatgccat gctggcaatc     840
gctgatatga tgaggaagaa aataacaatg ccggctcacc ttatgtacga tggacgggac     900
cctatgatat ttgagcactt ctcggctgtg gctcagcggc tcggtgtgta tacggctgat    960
gattacgctg atatcttgga attcttgatc gggcggtgga ggttgagaa gatggtgggg     1020 tgtcggctg aggctcagcg agctcagaac tatgtttgtg ggttggcgcc caggattagg    1080
aagctgcagg agcgagccga tgatcgggcg cgtaagatgg agccacaaag tgtcaagttt    1140
agctggatat ttaataagga agtcctcttg taa                                 1173
```

<210> SEQ ID NO 37
<211> LENGTH: 1164
<212> TYPE: DNA
<213> ORGANISM: Cannabis sativa

<400> SEQUENCE: 37

```
atgcaagtac aggtcagtaa tatttcattg tgggccttaa atggccacca aagcccaaac       60
aagctccaac tgagaagccc atcaccaaaa cccagattcc aagtctcagc cgtggcctca      120
ccaccgcggc cgatgaaact ccatcagcca acgatgccgc cggctaaaga agaagtgttc      180
aagtcgctaa aagggtgggc cacccaatcg attcttccac tgctaaagcc ggtggaggaa      240
tgttggcagc cccaagactt tttacccaac ccatcaaatt ctgacgaaga attcttcgat      300
gagatccgtt tgattcaaga tcgtgcggct gagattccag atgagtactt tgttgtcttg      360
gttggagata tgatcacgga ggaagcattg cctacttacc agaccattat gaactctatt      420
gatgccgtta aggataggac tggagtttgc tccagtccat gggctcggtg gacccgcgag      480
tggtccgccg aggagaatcg gcacggtgac ttgcttcgta cgtatttata cttatcgggt      540
cgggtcgata tgaccatggt tgaacggact atccaacatt tgattggagc tggcatgaat      600
ggaaatttca caacaatcc atacttgggt tatgtgtaca catcatttca agagcgagca      660
acatttgtgt cgcatggcaa cacagctcac ttagcgaaaa agagcggaga tccactcttg     720
gcgcgcattt gcggaactat tgcagccgat gagaagcgac acgagattgc ttacgtaaaa     780
atgaccgaga agctcttaga agttgaccca aataatgtca tgctcgcaat cgaggaaatg     840
atgaggagaa agatcacaat gccggccgcc cttatgtacg atggatgcga ccccatgtta    900
ttccaccact tctcggctgt ggctcagcgc ctcggcatct acacagctga tgactacgcc    960
```

```
gacatcttgg agttcttaat caaaaggtgg aggttagaga agatggaagg gttgaatccc    1020
gaggctcaaa gggcgcaaga ctttgtttgt ggccttgcgc cgagaattag gaagcttcaa    1080
gagcgagctg atgagcgtgc acaaaagatg gagcctctta gtgtcaagtt tagttggatt    1140
tttaacaaag aggttcttgt gtag                                           1164

<210> SEQ ID NO 38
<211> LENGTH: 1143
<212> TYPE: DNA
<213> ORGANISM: Cannabis sativa

<400> SEQUENCE: 38
atgcaagtac tacaagtttc atggcaggcc ttaagtggct ccaaagccc aaaaaatctc     60 caactgagaa gcccatcacc aaagcccaga ttccgagtct ccgccgtggc cttaccacca    120
ccaccgatgt cgccggatat agaagaagtt ttcaagtcac tagagagctg gccacccaa    180 tcaattatcc cactgctaaa gccggtggag gaatcttggc agccccaaga tttgttacca    240
agcccaacct ataataatgt cgaggaagaa ttcttcgatc agatccgttc gattcaagat    300
cgtgcggctg agattccaga tgagtacttt gttgtcttgg ttggagatat gatcacggag    360
gaagcattgc ctacatacca gaccattatg aattctattg atgccattaa ggataagact    420
ggagtttgct ccagtccatg ggctcggtgg acccgcgcat ggtccgccga ggagaatcgc    480
catggtgact tgcttcgtac ctatttatat ttaacgggtc gggtagatat gaccatggtt    540
gaacgtacta tccaacactt gattggagct ggcatggatg caagattcaa caacaatcca    600
tacttgtttt acgtgtacac atcatttcaa gaacgagcca cgtttgtgtc ccacggcaac    660
acggcccgct tagcgaaaaa caacggaaac ccactcttgg cgcgcatttg tgggactatt    720
gcggccgatg agaagcgtca cgagattgcg tacgtaaaag tgaccgagaa gctcttagaa    780
gttgacccaa ataatgccat gctagcaatt gaagaaatga tgaggagaaa gatcacaatg    840
ccggccttcc ttatgtacga tggatgcgac cccatgctat ccaccatttt ctcggctgtg    900
gctcagcgcc tcggcgtcta cacaactgat gactacgcca acatcttgga gttcttaatc    960
ggacagtgga agttagagaa gatggaaggg ttgaaacctg aagctcaaag agcgcaagac    1020
tatgtttgtg gccttgcacc gagaattagg aggctgcaag agcgagctga tgagcgcgca    1080
cggaagatgg ggcctcttag tgtcaagttt agttgggttt taacaagga ggttcttctc    1140 tag                                                                  1143

<210> SEQ ID NO 39
<211> LENGTH: 1164
<212> TYPE: DNA
<213> ORGANISM: Cannabis sativa

<400> SEQUENCE: 39
atgggagccg gtggccgaat gcccgaggcg aaatccgagt tgaatggtag taagaataat    60
aataggctaa ttgagagagt accacacacc aaaccaccat tcacattaag cgaaatcaag    120
aaagcaattc cgccccattg ctttaaacgc tctctaattc gctcttttgc ttgtgtcttt    180
cacgaccttt ttttcgcgtc attgttttac tatgttgcaa cctcttactt tcaccttatc    240
ccgaaaccaa tttcatacat tgcttggcca atttattgga ttttccaagg ttgtattttg    300
accggggttt gggtcatcgc tcatgagtgt ggtcaccatg cttttagtga ccaccagtgg    360
gtggatgaca ccgttggtct catcctccac tctgctcttc ttgtcccata ttttcatgg    420 aagtatagtc atcgtcgcca ccactcaaac acggggtcca ttgatcgcga cgaagtgttt    480
```

```
gtaccaaaac caaaatcaca agtgtcacca ttcgccaaat acttaaacaa tccacccggg      540
agagtcttaa gccttttgt taccctaaca cttggttggc ctttgtactt agctttcaat       600
gtatcaggca gaccatatga ccgtttcgct tgtcattatg atccctatgg cccaatctac      660
tcaaaccgcg aaaggttaca aatattcatc tcggacatag ggattttcat tgccacattc      720
gcgctatacc accttgtctc ggccaaaggg ttaggttggg ttgtgttagt gtatggtgtg      780
cctttgttaa tagtaaatgg cttccttgtt ttgatcactt acttgcaaca cactcaccct      840
gcattgcctc attatgactc gtccgaatgg gattggttga gaggagcatt gtcaaccgtt      900
gatcgagact atggaattct caatagggtt tttcacaaca ttactgacac tcatgttgtg      960
caccatttat tctcaacaat gccacattac aatgcaatgg aagcaaccaa agctgtgaag     1020
ccgatattag gcgagtacta ccgtttagat gacactccaa ttgttaaggc tatgtggaga    1080
gaagctaaag agtgtctcta tgttgagcaa gatgatgatt ctccatctaa caaggtgtt    1140 ttttggtaca aaacaagtt ttag                                             1164

<210> SEQ ID NO 40
<211> LENGTH: 1164
<212> TYPE: DNA
<213> ORGANISM: Cannabis sativa

<400> SEQUENCE: 40
atgggagtta aaagtcgaat gctcgagcca aaatccgagt tgaaagatag taagaacaat       60
aataatagcc caattgagag agcaccacac actaaaccac cattcacact aagccaaatc      120
aagaaagcca ttccacccca ttgcttccaa cgctctcttc ttcgctcctt cttttatgtc      180
tttcgagacc ttttctatgt cactttgttc tactacttag caacctctta cttccacctt      240 ctccccatc cactcccata cctagcttgg ccactttatt ggatcttcca aggttgtgct      300
ttgtttgctt tcgggctcat tggtcatgaa tgtggtcacc atgcctttag tgactacaaa      360
tggattgatg acatggttgg ttttgttatc cactctgcaa ttcttctccc atacttctca      420
tttaagtata gtcaccgtcg ccaccattca aacactggat ccattgatcg cgatgaagct      480
tttgttccaa agacgaaatc tcaaatgcca tggttctcca aatacttaaa caatccatta      540
ggaagagtcc taaccctagg ttttctatta accgtcggtt ttccttcata cttaactttc      600
aatatattag gcagacgata tgaccgtttc gcttctcatt atgatcctta ctctcctata      660
tactccaaca atgaaaggct tcaaatatta atttccgatg tgggggtttt catcaccaca      720
ttcgtgttgt accaactcgc cttagcaaga gggttgagtt gggttatgtt agtgtatggg      780
gtgccaatgg tattagtgag tggttggctt gttttggtca cttacttaca acacactcac      840
cctgcattgc ctcactatga ttcttccgaa tgggattggt tgagaggtgc tttgtcgaca      900
gttgatcgag actttggagt gctcaatagt atttttcata acatttcaaa cactcatgtt      960
gtgcaccatt tattcccccac aataccatat tacaatgcag tggaagcaac taaagctgtg     1020
aagccaatat taggagagta ctaccgttta gatgagactc caataattaa agctgtgtgg     1080
agagaggcaa aagagtgtct ctatgttgag agtgatgatg agtctcctct ttacaaaggt     1140
gttttttggt ataagaacaa gtaa                                             1164

<210> SEQ ID NO 41
<211> LENGTH: 1119
<212> TYPE: DNA
<213> ORGANISM: Cannabis sativa
```

<400> SEQUENCE: 41

```
atgggagtca atggtgaaaa tagtagactt gatcgagcac cacacaccac gccatcattc      60
acactaagcc aactcaagaa agccattcca ccccattgct tcaaccgttc tcttctccga     120
tccttctctt atctccttcg agaccttttt ttcgcctctt tgttctacta cgtagcaact     180
tcttactacc accttttccc tcaaccactc ttatactttg cttggccact ttattgggtc     240
tcccaaggct gcattttatt cggcttaggg ctcattggtc atgagtgtgg tcaccatgcc     300
tttagtgact acaaatgggt tgatgacatg gttggtttcg ttattcactc tgcttttctt     360
ctcccatact tttcgtttaa gtatagtcac cgacgccacc attcaaacac tggctccatt     420
gaccgcgatg aagcctttgt tccaaagacg aaatctcaaa tgccatggtt ctctaaatac     480
ttgaacaatc cactagggag agtcctaaca cttggtttct ttttaaccat ggttggcct      540
ttgtacttag cttgcaatat attaggtaga ccatatgacc gtttcgcttg tcattacgat     600
ccttactctc caatatactc aaaaaatgaa aggcttcaaa tattgatttc agatattggt     660
gttttcatca ccacattggt gttacaccaa cttgtcttag ccaaaggatt gagttgggtt     720
ttgttcgtgc atgggatacc attgctaata gtaggtgtct tgctagtttt gaccacttat     780
ttacaacaca ctcaccctgc attgccacac tatgactcgt ccgaatggga ttggttgaga     840
ggtgctttgt caaccgttga tcgagatttt ggagttctca atagtatttt tcataacgtt     900
tcaaacactc atgtgttgca tcatttattc cccaaaatac cacattacaa tgcaatagaa     960
gcaacaaaag ctgtgaagcc aatattagga gagtactatt gtttagatga gacttcaata    1020
attaaggcta tgtggcgaga ggccaaagaa tgtcttacg ttgaatcaga tgatgaatct    1080
tcgaaaaaag gtgttctttg gtacaagaac aaactttga                          1119
```

<210> SEQ ID NO 42
<211> LENGTH: 1132
<212> TYPE: DNA
<213> ORGANISM: Cannabis sativa

<400> SEQUENCE: 42

```
atggaagttg tagatgacca atatagtaac cttgttaggc gagcaccaca caccgaacca      60
ccattcacgc taagcgaaat caagaaagcc attccacccc attgcttcaa cgctctctt     120
ctccgctcct tctcttatct ccttcaagac cttttcttag tctctttact ctactacata     180
gcaacatctt acttccacct tcttcctcat tgcccatttt catacttagc ttggcccctt     240
tattggatct cccaaggctg catctcattt ggtatttggg tcattgctca tgagtgtggc     300
caccatgctt ttagtgatca ccaatgggtg gatgacaccg ttggtttcgt ccttcattcc     360
gctcttctct tcccatattt ctcttggaag tatagtcacc gtcgccacca caccaacact     420
ggctccatgg agcgcgatga agtgtgtgtc ccaaagccga atctcaaat gtcatggctc     480
tacaaatact tgaacaatcc attagggaga gtcctaagac ttagtgttac attgttcctt     540
ggttggcctc tttacttagg gttcaatgta tcaggtagat catataaccg tttcgcttgt     600
catttttgatc cttactcccc aatcttcaca aaaagggaaa ggcttcaagt attaatttca     660
aattttggtg ttttaattac tatatttgta ttgtaccaac tcagctcaac cagagggttg     720
agctggggttg tattcgtgta cgggggtgcca ttgcttatag tcaatggcac cattctctttg    780
atgacatatt tgcatcacac tcaccttgca ttgcctcact atgactcgtc cgaatgggat     840
tggttaaggg gtgctttgtc aacagtcgat cgagactatg gagttttcaa tagaattttt     900
cataatgtta cagacactca tgtattgcac catttattct caacaatacc tcattacaat     960
```

```
gcaatggaag ccaccaaagc tattaagcca atattgggag agtactattg tttcgatgag    1020
acttcgataa ttaaagctat gtggagagag attaaggagt gtgtctatgt tgaaccagat    1080
gatgaatctt cttctaataa aggtgtttta atggtataag aacaagttct aa            1132
```

<210> SEQ ID NO 43
<211> LENGTH: 1122
<212> TYPE: DNA
<213> ORGANISM: Cannabis sativa

<400> SEQUENCE: 43

```
atgggaactg aaggtggcca atatagtaga gttgtgagag caccacacac caaaccacca      60
ttcacactaa gccaaatcaa gaaatccatt ccgccccatt gcttcaaccg ctctcttctc     120
cgttccttct cttatctcct tcgagacctt tttttcgcct ctttattcta ctacgtagca     180
acctcttact tacaccttct cccacaccca cttttgtaca tggcttggcc actttactgg     240
atctcccaag gctgcatttg tttcggtatt tggatcattg ctcacgagtg cggtcaccat     300
gcttttagtg accaccaatg ggtggatgac actcttggct ttatcttcca ctctgctctt     360
ctcgtcccat acttctcatg gaagtatagt caccgtcgcc accattccaa caccggctct     420
attgagcgcg atgaagtgat tgttccaaag agaaaatcac aaatgccatg cattacaaa      480 tacctcaaca attcattagg gagattctta aggcttggtc ttaccgtgat tttcggttgg     540
cctttgtatg tgtgtttcaa tgcattaggt agaccatatg atcgtttcgc ttgtcatttt     600
gatccttact ctccaatcta ctcaaaaagc gaaaggcttc atatactaat ttcagatatt     660
ggtgttttaa ttaccatatt tttattgtac caactcagct cagttaaagg gttgagttgg     720
gttgtgatca cgtacgggat gccattacta gtagtaaata gcatccttgc ggtgatcaca     780
tacttgaatc acactcacct tgcattgcca cattatgact cgtcggaatg ggattggttt     840 agggtgctt tgtcaacggt tgatcgagat ttcggagttc tcaatggggt ttttcataac     900
atcacaaaca ctcatgtggt gcaccattta ttctcaacaa tgccacatta caatgcagtg     960
gaagcaacca aagctgtgaa gccaatattg ggagagtatt attgttttga tgacactccg    1020
gtaattaaag ctatgtggag agaggttaag gagtgtgtct atgttgagtc agatgatgaa    1080
tcttctaata aggtgttttt atggtataag aacaagttct ag                       1122
```

<210> SEQ ID NO 44
<211> LENGTH: 996
<212> TYPE: DNA
<213> ORGANISM: Cannabis sativa

<400> SEQUENCE: 44

```
atgggagccg gtggcaaaaa tagtagactt gagcgagcac cacacaccac accaccattc      60
acactaagcc aactcaagaa agccattcca cccattgct tcaaccgttc tcttcttcgt     120
tccttctctc atgtccttca agacctttt ttcgtctttt tgttctacta catagcaacc     180
tcttacttcc atcttctccc acacccgctc caatacttag cttggccact ttattggatc     240
ttccaaggca gcattttgtgc tggtatttgg gtccttggtc atgattgtgg tcaccaagct     300
ttcagtgacc accaatgggt ggatgacact gttggctttg cctccactc cgctcttctc     360 ttcccatact tctcttttaa gtatagtcat cgtcgccatc attcaaacat cggctccctt     420
gaacatgatc aattgtttgt tccagtcccc gaatctcaaa tcgcatggct ctacaaacat     480
tacttggaca atccactagg aagagcccta aagctttcta ttatagtgtt ccttggttct     540
```

```
ccttttgtact taggtttcaa tcttacaggc aaacaatatg atcgttctgc atgtcattat      600
gatccttact ctccactcta ctcaaaaagt gaaaggcttc atatattgat ttcagatatc      660
ggtgttttca tcaccacatt ggtgttatac cagcttggct cgactaaagg gttgagttgg      720
cttgtgttca tgtatggggt gccattgttt acagggaata gcatccttgt gacaatcgca      780
tacttgaatc atactcactc ttcattgcct cattatgact cgtcagagtg ggattggttg      840
aaaggagcat tgtcaacaat tgatcgaaac tatggatcaa ttctcaatag ggttttccat      900
caccttacag atgctcatat ggcacaccat ttattcgcaa caatacctca ttaccatgca      960
aatgaagcca ccagagctat caaacccata ttggga                                996

<210> SEQ ID NO 45
<211> LENGTH: 1152
<212> TYPE: DNA
<213> ORGANISM: Cannabis sativa

<400> SEQUENCE: 45
atgggtgccg gtggtcgaat gaatgttcct ccaggctcaa aaaatcaga ggccgaaagc        60 cttaaacgag ttccacacac aaaaccacca ttcacacttg gcgaaatcaa gaaagccatt      120 ccacccatt gtttccagcg ctctgttgtt cgctcattct cttatgtcgt ttatgacctt      180
accattgctg ccatccttta ctatattgct actcgttaca tccccctcct cccacaccct      240
ctgtcttacc tggcttggcc catttatggg ttcatccagg gttgtgtcct aactggtgtt      300
tgggtcatag cccacgagtg tggccaccac gcctttagtg accaccaatg gcttgacgat      360
accgtgggct tagtccttca ctctttcctt ctcgtcccct acttttcatg gaaatacagc      420
caccgtcgcc accattccaa cacaggctct cttgacaaag atgaagtctt tgttcccaag      480
aaaaagtctg ccatgaaatg gtactctaaa tacctcaaca atccccctgg cagattcctc      540
actctaacaa tcactctcac tctgggctgg cctctttact tggccttcaa tgtctcgggc      600 cggcccctatg accgttttgc atgccacttc gatccatacg gcccaatcta ctcggaccgt      660
gagcgggccc agatatacct atctgatgtg ggcattctcg caatgtgttt cggcctttac      720
aagctggcta tggcaaatgg gcttgcttgg gttttatgcg tgtatggagt cccattgttg      780
gtggtgaatg ggttttttggt gctgatcact ttcttgcaac acactcaccc atcgttgcct      840
cattacgata catccggagtg ggattggctt aggggagctt tggctacagt ggacagagat      900
tacggtttgt tgaacaaggt cttccataac atcacagaca cccatgtggc tcaccacttg      960
ttctccacaa tgcctcatta tcatgccatg gaggccacaa aagctatcaa gccaatactt     1020
ggagagtact accaatttga cggaacacca gtgtacaaag ccatgtggag agagactaag     1080
gaatgtgttt ttgtcgaagc ggatgaaggt gaaggcaaag gtgtcttctg gtacaacaag     1140
cttcgggatt ga                                                         1152

<210> SEQ ID NO 46
<211> LENGTH: 1191
<212> TYPE: DNA
<213> ORGANISM: Cannabis sativa

<400> SEQUENCE: 46
atgacagaat cacatgcttc ggaggaaatg gcgagagaag aaaaaggtga ctaccccatt        60
aaggtggcaa atgggatccg aaaccaaaac ggcgatttcg atctgagtga tcctccaccg      120
tttaagatag ctgagatccg agccgccatt cctaagcatt gttgggttaa gaatccatgg      180
cgctcactca gctatgtttt cagagatctc tttatcattt ttgcattggc ctttgccgct     240
```

```
ttctattccg atacttgggt cgtttggcca ttttactggg ctgctcaagg aaccatgttc      300
tgggctctct tcgttctcgg ccacgattgt ggccatggaa gcttttcaaa cagtcctgag      360
ctgaatagcg ctgtgggtca tattctgcat tctgcaatcc ttgtaccttta caatggatgg     420 agaattagcc atagaactca tcatcaaaac catggccatg ttgagaatga cgagtcatgg      480
gttccgttga ctgagaagat gtacaaacag ttggatgaga aaacaaagag gctgagattc      540
aaagtcccat ttcccttatt tgcatacccT tttatctgt ggaatagaag tccaggaaaa       600
gaaggctctc atttcaatcc ttacagcaaa ttatttactc caagtgagag aaaccaaata      660
ataacttcaa cggtttgctg tcaacaatg gctgctttgc ttgtctgttt gtccttcata       720
gtaggtcctg ttcaagttct catgctatat gttgttcctt attggatatt tgtgatgtgg      780
ctagacattg tcacttactt gcatcaccat ggttatgagc aaaaactccc ttggtaccgg      840
ggcaaggaat ggagttacct aaggggaggg ctaacaacag tagaccgtga ctatggaata     900
tttaacaata tccaccatga cattggaact catgttatac accatctctt ccctcaaatc      960
ccacactacc atcttgtgga agctaccaag gcagccaagc cagtgctcgg aaagtattac      1020
agggagccta aaagtcagg gccaattcca gtccacttga tcgagaatct agttaagagc       1080
atcagccagg accactatgt gagtgacaat ggcgaagtag tatactacca gacagaccca     1140
gaacttaata ataataataa taaaaaaata tctgaggcca agcaaatgta g              1191

<210> SEQ ID NO 47
<211> LENGTH: 1359
<212> TYPE: DNA
<213> ORGANISM: Cannabis sativa

<400> SEQUENCE: 47
atggcgagtt gggttttgtc agaatgtgga ttaaagccac tccctcaaaa ttttcctcga      60
cccagaacag ggattacctc aaccaaccca acaacaaaga ctcggttttt gagttctaac      120
aagagctcgg cggatcttag attcccaaag gtgaatttct caactgggtt tttgaaaagg      180
aggagttttg aggtgagagt gagcgcccca ttgaaggttg cttttgtaga agaggaagac      240
agaggagaga gagtagagga atcgttaat ggagttgaag aagaagaaga agagggaatc      300
aaatttgatc ctggctcggc tccaccttc aaattggctg atattcgggc tgctattcca      360
aaacattgtt gggttaagga tccatggaag tctatgagct atgtggtgag agatgtggct      420
atcatatttg ggttggctgc ggctgctgct tctattaaca actgggttgt ttggcctttg      480
tactgggctc tcagggggac tatgtttttgg gctctatttg ttcttggtca tgactgtggc      540
catggaagct tttcaaacga tcataagcta acagtgtag ttgggcatct cttgcattcc      600
tcaattcttg tacctatca tggatggaaa actagccata aaaccatca ccaaaaccat       660 ggacatgttg agaatgatga atcatggcat ccgttacctg aaagaattta caggaaactg      720
gataacatca caaaagttt gagatttact ctaccatttc caatgcttgc ttatcctttc       780
tacctttggg gaagaagtcc aggaaaggct ggttctcatt ttcatccaaa tagtgacttg      840
tttgttccaa gtgagaagaa agatgtgatc acttccactt tatgttggac agctatggct      900
gctatacttg tttggtttggg ctttgtgatg gtcctattcc aattgcttaa gctctatggc     960
attccttatt gggttttgt catgtggctg gatttagtga catacttgca tcaccatggc      1020
catgaagaaa aattaccatg gtaccgcgga aaggaatgga gttacttaag aggagggctc      1080
acgacacttg atcgcgatta tggagtgatt aacaacattc atcatgatat tggaactcat     1140
```

| | | | |
|---|---|---|---|
| gtaatccacc | atcttttccc | tcaaattcct cactaccact tggtggaagc aaccgaggca | 1200 |
| gctaaaccag | tgatagggaa | atactacaga gagccgaaga aatcgggtcc tctaccgttt | 1260 |
| cacttgatag | gtgctttgat | tagaagcttg aaacaagatc actatgttag tgacactggt | 1320 |
| gatgttgtgt | actacaaaac | tgatcctgat cttaagtga | 1359 |

<210> SEQ ID NO 48
<211> LENGTH: 1350
<212> TYPE: DNA
<213> ORGANISM: Cannabis sativa

<400> SEQUENCE: 48

| | | | |
|---|---|---|---|
| atggcgactt | gggtcttatc | agaatgtggc gtaaaacctc ttcttagagt ctaccctcaa | 60 |
| cccagaaccg | gaatgttgtt | gaagccttcc atcccgtcga gtcttaggac attgccggtc | 120 |
| tgtaagagta | gccaattggg | tttctcattg tcttcctcaa gtgggtttag ggggcagaat | 180 |
| tggaaactta | atgtgagtgc | tccattaaga gtctctgatg ttggtgaaga agataatgag | 240 |
| aagagggtag | tggaagatga | aagtggattc gaccctggtg cgccgcctcc atttaagttg | 300 |
| gctgatatta | gagcagccat | tcctaaacac tgttggatta aggacccatg gagatctatg | 360 |
| agctatgttt | tgagggacgt | tgttgtcgtt tttggtatgg cggctgcggc tgcttattta | 420 |
| aacaactggg | ccgtttggcc | tctgtactgg attgctcaag gaaccatgtt ctgggctctt | 480 |
| tttgttcttg | gccacgactg | tggtcatgga agttttctcta ataacgcaaa ccttaatagc | 540 |
| gtggtgggtc | atattcttca | ttcttcaatc cttgtcccat accatggatg gagaataagc | 600 |
| cacaggactc | atcatcagaa | ccatggacac attgaaaacg atgaatcttg catccgcta | 660 |
| tctgagaaaa | tctacaatag | cttggataag ggtaccaaat tgctgaggtt taccttgcct | 720 |
| ttccctatgc | ttgcttaccc | ttttatctg tggagtcgaa gtcccggaaa gaagggttct | 780 |
| cattttgatc | caaacagtga | cttgtttgtt gagagtgaaa ggaaagacat catcacctcc | 840 |
| actgcatgtt | ggactgccat | ggttgctctg ctcggtgtgc tctcctttgt aatgggtcct | 900 |
| gttcaactca | ttaagctcta | tattgttccc tactggattt ttgtcatgtg gttggacttg | 960 |
| gtcacttact | tgcatcatca | tggccacgag gacaaacttc catggtatcg tggaaaggag | 1020 |
| tggagttatc | taagaggtgg | actaactact cttgaccgtg attatggatg gatcaataac | 1080 |
| attcaccatg | atattggaac | tcatgttata catcatctct cccctcaaat cccacattat | 1140 |
| cacttagtgg | aagcaacaga | ggcagctaga cctgtatttg gtaaatacta taaggagcca | 1200 |
| aataaatctg | gacctttacc | atttcacttg cttggaagtt taataagaag catgaaaaag | 1260 |
| gatcactatg | ttagtgatac | aggggatgtt gtttactacc aaactgatcc aaagctatat | 1320 |
| gggccttctg | aatctgactc | ttccacatga | 1350 |

<210> SEQ ID NO 49
<211> LENGTH: 1344
<212> TYPE: DNA
<213> ORGANISM: Cannabis sativa

<400> SEQUENCE: 49

| | | | |
|---|---|---|---|
| atggaagccg | agaagaagta | cattaccact gaggaactga aggagcacaa caaggcaggg | 60 |
| gatctgtgga | tctctattca | gggtaaggtt tataatgtat cagaatggct taaggatcac | 120 |
| cctggtgggg | atgcgcctct | actaagtttc gctggcagag atgttactga tgcttttatt | 180 |
| gcataccatc | ccggtactgc | gtggaagcat cttgatcagt ttttcaccgg ttattatgtc | 240 |
| aaagatttcg | tggtctcaga | gatttccaag gattatagga gaatttcaaa cgagtttacc | 300 |

```
aaactggggt tgtttgaaaa gaaaggtcat gggattttct acactctcac atgtgttgct    360
ataatgcttt ccatggttgt ttatggtgtt gtgaaatctg agagcatttt agtccatatg    420
ggttgtgctg tcgtattggg gatgctttgg attcaaagcg cttatgttgg catgattct     480 gggcattatc aggtcatgtt aagccctgga tataacaaat ttgctcagct tttggctggg    540
aattgtctta ctgggattag cattgcttgg tggaaatgga ctcataatgc ccatcatatt    600
gcttgcaaca gccttgatta tgatccagat cttcaacaca ttcccgtctt tgcagtgtct    660
tctaaattct tcaagtccat tacttcacgc ttttatggaa gggagttgac attcgattca    720
ttgtctaggt tcatgatcag ttaccaacat tggacatatt atccagttat gtgtgttgcc    780
agggttaact tgtttgtaca gacactattg ttgctcttgt caaaaagacc tatcccaaat    840
agagctttga acataatggg aaccttgtgt tctggactt ggttccctct ccttgtttca     900
tgtttgccca cctggacaga gaggacgatg tttgtgctct tgagctttgc agtcacatca    960
gttcaacatg ttcaattcac tttgaaccat ttctcagcag atgtttatct cggtcaccct   1020
ggtgggaatg attggtttga aagcaggct gctgggacta tagatatttc atgctcacct    1080
tggatggatt ggttctatgg agggctgcag tttcagcttg agcatcattt gttcccacgc   1140
atgcctcgtt gccaattgag gaacatttct cctattgttg ttgacctttg caagaagcac   1200
aatttgcctt acaggagctt atcattctgg gacgccaatg tttccaccct taaaactctc   1260
aggactgctg cccttcaagc acgagatctc accaacccta tccccaagaa cttggtctgg   1320
gaagctgtta atactcatgg ctga                                          1344

<210> SEQ ID NO 50
<211> LENGTH: 1344
<212> TYPE: DNA
<213> ORGANISM: Cannabis sativa

<400> SEQUENCE: 50
atggcggatt caacaaaata cattacccaa gaagagctta acaacacaca caaacatgga     60
gatctatgga tctcaatcca aggcaaaatc tacaacgtct cagattgggc caaagaccat    120
cccggcggcg aacacccatt actaaatctc gccggtcaag acgtaacaga agctttcata    180
gcttaccatc caaggtcggc atggcaatac atggaccaat tctttactgg gtttcatctc    240
aaagatcact cctttaccga ggtttcaaag gattacagaa aactcgtcaa tgaatttacc    300
aaaatgggtt tgtttgagaa gaaaggacat ggggtttgct tctcattctt cttcattaca    360
ttgtttttta tactcagtgt ttatggtgtt atgtgttctg atagtatttt ggttcatttc    420
tgttctggat gtttattagg ttttttatgg attcaaagtg ttggttaggt catgattca    480 ggtcattatc aaatcatgac taatcaattt tataacagat ttgttcagat cttaactggg    540
aattgtttag ctgggattag tattgcttgg tggaaatgga atcacaatgc tcatcattta    600
gcttgtaata gtcttgaatt tgatcctgat cttcaacaca tgccattctt tgttgtatca    660
tcaaaattct ttgattcact cacgtcacat ttctatggca gaaaattgag ttttgattca    720
atcacaagat cttagttag ttaccaacat tggacatttt accctgtcat gtgtttagct    780
aggcttaatc tcttcgctca atcatttgct ttgttattat ctaagagaaa agttcataat    840
agaggtcaag agattcttgg gttacttgtg ttttggattt ggtatccact tttggtttca    900
tatttaccaa attggagtga aagggttatg tttgtcatgg caagttttttc agtaactggt    960 atccaacatg ttcaattttg tttgaaccat ttctcagcta atgtttatgt tggtttgcca   1020
```

```
agtagttatg attggtttga gaagcaaaca aaagggacac ttaatatcct ttgtccttct   1080
tggatggatt ggtttcatgg cggtttgcag tttcagattg aacaccattt gtttccaaga   1140
ttgcccaaat cacaactgag gaaaatttct ccctttgttt atgaactgtg taagaagcat   1200
aatttgcctt ataattgtgc ttcgttttgg gaagctaatg taatgacagt gaatactctt   1260
aagaccgcgg ctttgcaggc tcgcgatctt actaatcctg ttccgaagaa cttggtttgg   1320
gaagctgtca atactcatgg atag                                          1344
```

DESATURASE NUCLEIC ACIDS AND POLYPEPTIDES

CROSS REFERENCE TO RELATED APPLICATIONS

This is the U.S. National Stage of International Application No. PCT/GB2014/053631, filed Dec. 8, 2014, which was published in English under PCT Article 21(2), which in turn claims the benefit of Great Britain Application No. 1321786.4, filed Dec. 10, 2013 and Great Britain Application No. 1321889.6, filed Dec. 11, 2013.

FIELD OF THE INVENTION

This disclosure relates to the identification of delta-12 and delta-15 desaturase genes involved in the desaturation of oleic acid to linoleic acid and further to alpha linolenic acid; plants comprising mutations in the delta-12 and/or delta-15 desaturase genes that have seed with altered fatty acid content are also disclosed.

BACKGROUND TO THE INVENTION

Edible oils containing lower levels of saturated fatty acids and elevated concentrations of oleic acids and poly unsaturated fatty acids such a linoleic acid are highly desirable due to the perceived dietary health benefits and possibly preventing diseases such as arteriosclerosis or diabetes. Moreover, monounsaturated oils, such as oleic acid are suitable replacements to petroleum-based feedstocks in the manufacture of plastic, lubricants and cosmetics and are known to enhance the combustion of biodiesel.

Vegetable oils extracted from plants comprise various amounts of saturated, mono- and polyunsaturated fatty acids and although mono- and polyunsaturated oils both have their use, polyunsaturated oils are considered contaminants in oils for industrial use as they are prone to oxidation and difficult to remove during oil processing. Therefore, plants with high concentrations of oleic acid (OA), a monounsaturated fatty acid, and low amounts of polyunsaturated fatty acids such as linoleic acid (LA) or alpha-linolenic acid (ALA) are highly desirable.

Two multifunctional classes of desaturases have been found in plants, one soluble and the other membrane bound. In plants C16- and C18-fatty acids are synthesized in the stroma of plastids and with desaturation of 18:0 to 18:1 by a soluble delta-9 stearoyl ACP desaturase also occurring in plastids. Further desaturation of fatty acids in membrane lipids of the chloroplast and endoplasmic reticulum (ER) is carried out by the membrane bound desaturases, a number of which have been designated FAD2 to FAD8.

The seeds of *Cannabis sativa* L. (hemp, marijuana) are an important source of oil and protein in human nutrition dating back to Neolithic times in ancient China. *C. sativa* has an annual life cycle and is mostly dioecious with male and female flowers borne on separate plants. Selective breeding has produced marijuana strains accumulating high levels of psychoactive cannabinoids in the female flowers and hemp cultivars typically having low levels of cannabinoids but good fibre and/or seed oil traits. Hemp has modest agrochemical requirements, is an excellent break crop and is suited to warm-to-temperate growing conditions. At over 80% in polyunsaturated fatty acids (PUFAs), hemp seed oil rivals most of the commonly used vegetable oils. At 56% LA and 22% ALA hemp oil is a rich source of these essential fatty acids. In addition, hemp oil also contains gamma linolenic acid (GLA) and stearidonic acid (SDA) which occur at about 4% and 2% respectively.

This disclosure relates to two novel desaturase genes in hemp catalysing desaturation of oleic acid (OA) to LA and LA to ALA. Homozygous plants lacking the delta-12 desaturase [also known as FAD2 desaturase] show increased amounts of OA, whereas plants lacking the delta-15 desaturase [also known as FAD3 desaturase] show increased amounts of LA and near zero levels of ALA. Plants carrying a specific point mutation in the delta-12 desaturase show increased amounts of GLA and when this delta-12 desaturase point mutation is crossed into plants lacking the delta-15 desaturase there is a further increase in the amounts of GLA, a profile desired to efficiently purify GLA from plants. Plants carrying single delta-12 desaturase or delta-15 desaturase mutations or both mutations are also disclosed, as are plants engineered to down-regulate or ablate expression of delta-12 desaturase and/or delta-15 desaturase.

STATEMENT OF THE INVENTION

According to an aspect of the invention there is provided a modified *Cannabis* spp plant wherein said plant is modified in a gene encoding a delta-12 desaturase polypeptide wherein the modification reduces or abrogates the expression or activity of said delta-12 desaturase and said modified plant has enhanced oleic acid content when compared to a wild-type *Cannabis* spp plant comprising an unmodified delta-12 desaturase gene.

In a preferred embodiment of the invention said modified plant has an increased oleic acid content of between 70-85% of total oil content of the modified plant when compared to the wild-type plant comprising a wild-type copy of said delta-12 desaturase gene.

In a further embodiment of the invention said modified plant has reduced linoleic acid content when compared to a wild-type plant.

In a preferred embodiment of the invention the linoleic acid content is between 1-5% of the total oil content of the modified plant when compared to a wild-type plant.

In a preferred embodiment of the invention said modified plant has reduced alpha linolenic acid content when compared to a wild-type plant.

In a preferred embodiment of the invention said modified plant has an alpha linolenic acid content between 2.5-7.5% of the total oil content of the modified plant when compared to a wild-type plant.

In a preferred embodiment of the invention said modified plant has reduced gamma linolenic acid content when compared to a wild-type plant.

In a preferred embodiment of the invention the gamma linolenic acid content of said modified plant is between 0.5-1.5% of the total oil content of the modified plant when compared to a wild-type plant.

In a preferred embodiment of the invention said modified plant includes a modification to a delta-12 desaturase genomic sequence comprising the nucleotide sequence as set forth in SEQ ID NO: 1, or a polymorphic sequence variant thereof.

According to a further aspect of the invention there is provided a modified *Cannabis* spp plant wherein said plant is modified in a gene encoding a delta-12 desaturase polypeptide wherein the modification modulates said delta-12 desaturase expression and/or activity relative to other membrane bound desaturases and said modified plant has enhanced gamma linolenic acid content when compared to a wild-type *Cannabis* spp plant comprising an unmodified delta-12 desaturase gene.

In a preferred embodiment of the invention said delta-12 desaturase is modified at or around amino acid residue proline 341.

In a preferred embodiment of the invention said delta-12 desaturase is modified at amino acid residue proline 341 by amino acid substitution. Preferably said substitution is replacement of amino acid residue proline 341 with leucine.

In a preferred embodiment of the invention said modified *Cannabis* spp plant has a gamma linolenic acid content 5-15% of the total oil content of the modified plant when compared to a wild-type plant.

According to a further aspect of the invention there is provided a modified *Cannabis* spp plant wherein said plant is modified in a gene encoding a delta-15 desaturase polypeptide wherein the modification reduces or abrogates the expression or activity of said delta-15 desaturase and said modified plant has enhanced linoleic acid content when compared to a wild-type *Cannabis* spp plant comprising an unmodified delta-15 desaturase gene.

In a preferred embodiment of the invention said modified *Cannabis* spp plant has low or undetectable alpha linolenic acid content when compared to a wild-type plant.

In a preferred embodiment of the invention said modified *Cannabis* spp plant has a linoleic acid content between 60% to 70% of the total oil content of the modified plant when compared to a wild-type plant.

In a preferred embodiment of the invention said modified plant comprising a modification to a delta-12 desaturase genomic sequence and further comprising a modification to a delta-15 desaturase genomic sequence has increased gamma linolenic acid when compared to the wild type plant.

In a further preferred embodiment of the invention the gamma linolenic acid content of said modified plant is 10 to 15%; for example 10.9 to 11.7%.

In a further preferred embodiment of the invention the oleic acid content of said modified plant is 7.5% to 10%; for example 8.5 to 8.9%.

In a further preferred embodiment of the invention the linoleic acid content of said modified plant is 50% to 75%; for example 63 to 70.5%.

In a further preferred embodiment of the invention the alpha linolenic acid content of said modified plant is 0.1 to 1%; for example 0.4 to 0.6%.

In a preferred embodiment of the invention said modified plant includes a modification to a delta-15 desaturase genomic sequence comprising the nucleotide sequence as set forth in SEQ ID NO: 2, or a polymorphic sequence variant thereof.

In a preferred embodiment of the invention said delta-12 and/or delta-15 desaturase gene[s] are modified in the nucleotide coding sequence to introduce one or more termination or nonsense codons thereby preventing expression of said desaturase[s].

According to an aspect of the invention there is provided an isolated nucleic acid molecule that encodes a *Cannabis* spp desaturase polypeptide wherein said nucleic acid molecule comprises or consists of a nucleotide sequence selected from the group consisting of:

i) a nucleotide sequence as represented by the sequence in SEQ ID NO: 1 or 2;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the sequence in SEQ ID NO: 1 or 2 wherein said nucleic acid molecule encodes a desaturase;

iv) a nucleotide sequence that encodes a polypeptide comprising an amino acid sequence as represented in SEQ ID NO: 3 or 4;

v) a nucleotide sequence that encodes a polypeptide comprising an amino acid sequence wherein said amino acid sequence is modified by addition deletion or substitution of at least one amino acid residue as represented in iv) above and which has retained or enhanced desaturase activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
 Hybridization: 5×SSC at 65° C. for 16 hours
 Wash twice: 2×SSC at room temperature (RT) for 15 minutes each
 Wash twice: 0.5×SSC at 65° C. for 20 minutes each High Stringency (Allows Sequences that Share at Least 80% Identity to Hybridize)
 Hybridization: 5×-6×SSC at 65° C.-70° C. for 16-20 hours
 Wash twice: 2×SSC at RT for 5-20 minutes each
 Wash twice: 1×SSC at 55° C.-70° C. for 30 minutes each Low Stringency (Allows Sequences that Share at Least 50% Identity to Hybridize)
 Hybridization: 6×SSC at RT to 55° C. for 16-20 hours
 Wash at least twice: 2×-3×SSC at RT to 55° C. for 20-30 minutes each.

In a preferred embodiment of the invention said nucleic acid molecule comprises or consists of a nucleotide sequence as set forth in SEQ ID NO: 1 or 2.

In a preferred embodiment of the invention said nucleic acid molecule comprises of a nucleotide sequence set forth in SEQ ID NO: 1 and encodes a delta-12 desaturase.

In a preferred embodiment of the invention said nucleic acid molecule comprises of a nucleotide sequence set forth in SEQ ID NO: 2 and encodes a delta-15 desaturase.

In a preferred embodiment of the invention said nucleotide sequence is a cDNA sequence.

In an alternative embodiment of the invention said nucleotide sequence is a genomic sequence.

According to a further aspect of the invention there is provided an isolated polypeptide selected from the group consisting of:

i) a polypeptide comprising or consisting of an amino acid sequence as represented in SEQ ID NO: 3 or 4; or ii) a modified polypeptide comprising or consisting of a modified amino acid sequence wherein said polypeptide is modified by addition, deletion or substitution of at least one amino acid residue of the sequence presented in SEQ ID NO: 3 or 4 and which has retained or enhanced desaturase activity.

A modified polypeptide as herein disclosed may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 50% identity, even more preferably at least 55% identity, still more preferably at least 60%, 65%, 70%, 75%, 80%, 85%, 90%, 95% identity, and at least 99% identity with most or the full length amino acid sequence illustrated herein.

In a further preferred embodiment of the invention the variant polypeptides have at least 84% identity with reference to the full length amino acid sequence set forth in SEQ ID NO: 3.

In a further preferred embodiment of the invention the variant polypeptides have at least 78% identity with reference to the amino acid sequence set forth in SEQ ID NO: 4.

In a preferred embodiment of the invention said polypeptide according to the invention or said variant polypeptide comprises or consists of the amino acid sequence set forth in SEQ ID NO: 3 wherein said polypeptide is a delta-12 desaturase.

In a preferred embodiment of the invention said polypeptide according to the invention or said variant polypeptide comprises or consists of the amino acid sequence set forth in SEQ ID NO: 4 wherein said polypeptide is a delta-15 desaturase.

According to a further aspect of the invention there is provided a vector comprising a nucleic acid molecule encoding a desaturase polypeptide according to the invention wherein said nucleic acid molecule is operably linked to a nucleic acid molecule comprising a promoter sequence.

In a preferred embodiment of the invention said nucleic acid sequence comprising a promoter confers constitutive expression on said desaturase.

In an alternative preferred embodiment of the invention said nucleic acid molecule comprising a promoter confers regulated expression on said desaturase.

In a preferred embodiment of the invention said regulated expression is tissue or developmentally regulated expression.

In a further alternative embodiment of the invention said regulated expression is inducible expression.

Preferably the nucleic acid molecule in the vector is under the control of, and operably linked to, an appropriate promoter or other regulatory elements for transcription in a host cell such as a microbial, (e.g. bacterial, yeast), or plant cell. The vector may be a bi-functional expression vector which functions in multiple hosts. In the case of desaturase genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. Application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference).

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is a tissue specific promoter, an inducible promoter or a developmentally regulated promoter.

Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809). If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

According to a further aspect of the invention there is provided a transgenic cell transformed or transfected with a nucleic acid molecule or vector according to the invention.

In a preferred embodiment of the invention said cell is a plant cell.

In a preferred embodiment of the invention said plant cell is from the genus *Cannabis* spp.

In a preferred embodiment of the invention said plant cell is a *Cannabis sativa* cell.

According to a further aspect of the invention there is provided a plant comprising a plant cell according to the invention.

In a preferred embodiment of the invention said plant is from the genus *Cannabis*; preferably *Cannabis sativa*.

According to a further aspect of the invention there is provided a seed obtained from the plant according to the invention.

In an alternative preferred embodiment of the invention said cell is a microbial cell; preferably a bacterial or fungal cell [e.g. yeast, *Saccharomyces cerevisae*].

In a preferred embodiment of the invention said cell is adapted such that the nucleic acid molecule encoding the desaturase is over-expressed when compared to a non-transgenic cell of the same species.

According to a further aspect of the invention there is provided a nucleic acid molecule comprising a transcription cassette wherein said cassette includes a nucleotide sequence designed with reference to part of SEQ ID NO: 1 or 2 and is adapted for expression by provision of at least one promoter operably linked to said nucleotide sequence such that both sense and antisense molecules are transcribed from said cassette.

In a preferred embodiment of the invention said cassette is adapted such that both sense and antisense ribonucleic acid molecules are transcribed from said cassette wherein said sense and antisense nucleic acid molecules are adapted to anneal over at least part or all of their length to form a inhibitory RNA or short hairpin RNA.

In a preferred embodiment of the invention said cassette is provided with at least two promoters adapted to transcribe both sense and antisense strands of said ribonucleic acid molecule.

In an alternative preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an ribonucleic acid molecule which forms a double stranded region by complementary base pairing of said first and second parts thereby forming an short hairpin RNA.

A technique to specifically ablate gene function is through the introduction of double stranded RNA, also referred to as small inhibitory/interfering RNA (siRNA) or short hairpin RNA [shRNA], into a cell which results in the destruction of mRNA complementary to the sequence included in the siRNA/shRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said nucleic acid molecule is part of a vector adapted for expression in a plant cell.

According to a further aspect of the invention there is provided a plant cell transfected with a nucleic acid molecule or vector according to the invention wherein said cell has reduced expression of one or more desaturase[s] according to the invention.

According to a further aspect of the invention there is provided a plant wherein said plant comprises a transfected plant cell according to the invention.

According to a further aspect of the invention there is provided the use of a gene encoded by a nucleic acid molecule comprising the nucleic acid sequence in SEQ ID NO: 1 or 2, or a nucleic acid molecule the complementary strand of which hybridizes under stringent hybridization conditions to the nucleotide sequence in SEQ ID NO: 1 or 2 wherein said nucleic acid molecule encodes a polypeptide with desaturase activity as a means to identify a locus wherein said locus is associated with altered expression or activity of said desaturase.

Mutagenesis as a means to induce phenotypic changes in organisms is well known in the art and includes but is not limited to the use of mutagenic agents such as chemical mutagens [e.g. base analogues, deaminating agents, DNA intercalating agents, alkylating agents, transposons, bromine, sodium azide] and physical mutagens [e.g. ionizing radiation, psoralen exposure combined with UV irradiation].

According to a further aspect of the invention there is provided a method to produce a *Cannabis* spp plant that has altered expression of a desaturase polypeptide according to the invention comprising the steps of:
 i) mutagenesis of wild-type seed from a *Cannabis* spp plant that does express said desaturase;
 ii) cultivation of the seed in i) to produce first and subsequent generations of plants;
 iii) obtaining seed from the first generation plant and subsequent generations of plants;
 iv) determining if the seed from said first and subsequent generations of plants has altered nucleotide sequence and/or altered expression of said desaturase polypeptide;
 v) obtaining a sample and analysing the nucleic acid sequence of a nucleic acid molecule selected from the group consisting of:
  a) a nucleic acid molecule comprising a nucleotide sequence as represented in SEQ ID NO: 1 or 2;
  b) a nucleic acid molecule that hybridises to the nucleic acid molecule in a) under stringent hybridisation conditions and that encodes a polypeptide with desaturase polypeptide activity; and optionally vi) comparing the nucleotide sequence of the nucleic acid molecule in said sample to a nucleotide sequence of a nucleic acid molecule of the original wild-type plant.

In a preferred method of the invention said nucleic acid molecule is analysed by a method comprising the steps of:
i) extracting nucleic acid from said mutated plants;
ii) amplification of a part of said nucleic acid molecule by a polymerase chain reaction;
iii) forming a preparation comprising the amplified nucleic acid and nucleic acid extracted from wild-type seed to form heteroduplex nucleic acid;
iv) incubating said preparation with a single stranded nuclease that cuts at a region of heteroduplex nucleic acid to identify the mismatch in said heteroduplex; and
v) determining the site of the mismatch in said nucleic acid heteroduplex.

In a preferred method of the invention said *Cannabis* spp plant has enhanced desaturase polypeptide expression and/or activity.

In an alternative preferred method of the invention said *Cannabis* spp plant has reduced or abrogated desaturase polypeptide expression and/or activity.

According to a further aspect of the invention there is provided a plant obtained by the method according to the invention.

According to an aspect of the invention there is provided a plant wherein said plant comprises a viral vector that includes all or part of a gene comprising a nucleic acid molecule according to the invention.

In a preferred embodiment of the invention said gene is encoded by a nucleic acid molecule comprising a nucleic acid sequence selected from the group consisting of:
i) a nucleic acid molecule comprising a nucleotide sequence as represented in SEQ ID NO: 1 or 2;
ii) a nucleic acid molecule comprising a nucleotide sequence that hybridises under stringent hybridisation conditions to a nucleic acid molecule in (i) and which encodes a desaturase polypeptide;
iii) a nucleic acid molecule that encodes a variant polypeptide that varies from a polypeptide comprising the amino acid sequence as represented in SEQ ID NO: 3 or 4.

According to a further aspect of the invention there is provided a viral vector comprising all or part of a nucleic acid molecule according to the invention.

According to an aspect of the invention there is provided the use of a viral vector according to the invention in viral induced gene silencing in a plant.

In a preferred embodiment of the invention said plant is from the genus *Cannabis* spp.

Virus induced gene silencing [VIGS] is known in the art and exploits a RNA mediated antiviral defense mechanism. Plants that are infected with an unmodified virus induce a mechanism that specifically targets the viral genome. However, viral vectors which are engineered to include nucleic acid molecules derived from host plant genes also induce specific inhibition of viral vector expression and additionally target host mRNA. This allows gene specific gene silencing without genetic modification of the plant genome and is essentially a non-transgenic modification.

According to a further aspect of the invention there is provided a process for the preparation of oil from a *Cannabis* spp plant comprising the steps:
i) obtaining seed according to the invention;
ii) extracting from the seed a fraction comprising plant oil; and optionally
iii) isolating said oil fraction to provide an enriched oil fraction.

In a preferred embodiment of the invention said material is cold press extracted.

According to a further aspect of the invention there is provided an oleic acid-enriched oil preparation obtained or obtainable by the process according to the invention.

In a preferred embodiment of the invention said preparation comprises 70-85% oleic acid.

In a preferred embodiment of the invention said preparation comprises 2.5-7.5% alpha linolenic acid.

In a preferred embodiment of the invention said preparation comprises 0.5-1.5% gamma linolenic acid.

In a preferred embodiment of the invention said oleic acid-enriched oil preparation is at least 7 fold more stable than oil preparation extracted from seed of a wild type *Cannabis* spp plant.

According to an alternative aspect of the invention there is provided a gamma linolenic acid-enriched oil preparation obtained or obtainable by the process according to the invention.

In a preferred embodiment of the invention said preparation comprises 10 to 15% gamma linolenic acid, for example 10.9-11% gamma linolenic acid.

In a preferred embodiment of the invention said preparation comprises 7.5% to 10% oleic acid, for example 8.5-8.9% oleic acid.

In a preferred embodiment of the invention said preparation comprises 50-75% linoleic acid, for example 63-70.5% linoleic acid.

In a preferred embodiment of the invention said preparation comprises 0.1-1% alpha linolenic acid, for example 0.4-0.6% alpha linolenic acid.

According to a further aspect of the invention there is provided a gamma linolenic acid-enriched oil preparation obtained or obtainable by the process according to the invention.

In a preferred embodiment of the invention said preparation comprises 5-15% gamma linolenic acid.

According to a further aspect of the invention there is provided a linoleic acid-enriched oil preparation obtained or obtainable by the process according to the invention.

In a preferred embodiment of the invention said preparation has low or undetectable alpha linolenic acid content.

In a preferred embodiment of the invention said preparation comprises 60-70% linoleic acid.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures:

FIGS. 1A-1B Expression of putative desaturase genes in developing embryos of the hemp cultivar Finola and metabolic context. (A) Embryos representative of each developmental stage used for RNA isolation are shown (Scale bar=1 mm). EST libraries from torpedo (T), upturned (U) and filled not dessicated (FND) stages of embryo development were generated by deep sequencing and read counts analysed in silico. Raw reads were mapped to reference sequence, which consisted of the open reading frames of 17 putative desaturase genes as detailed in Table 1 with BWA mapping software (Li, 2009). The raw read counts were retrieved from the resulting output file for each gene in the EST libraries and the counts were then normalized to RPKM (Reads Per Kilobase per Million) values which is considered representative of transcript abundance. Gene expression is depicted in a heat map format with RPKM values included. (B) Schematic presentation of the biosynthetic pathway giving rise to the major fatty acids in hemp seed oil. SACPD—stearoyl ACP desaturase, DS—desaturase. Enzymatic steps are shown in bold and those steps compromised by mutation in specific CSFAD2 and CSFAD3 genes as detailed in FIGS. 2C-2D and FIGS. 3C-3D are indicated;

FIGS. 2A-2D Characterisation of CSFAD2A gene function. (A) Expression of CSFAD2A and CSFAD2B in developing embryo and mature leaf tissue compared to levels in young hemp leaves. Raw quantitative PCR data were normalised to hemp ACT2 transcript level in each tissue and expressed on a logarithmic scale as $(1+E)-\Delta\Delta Ct$ where E is the amplification efficiency. Mean values represent the average of three biological replicas each consisting of three technical replicates. (YL, young leaves; ML, mature leaves; TORP, torpedo stage of hemp embryo; UPT, U-upturned stage of hemp embryo; FND, filled-not-desiccated stage of hemp embryo; MAT mature seed embryo). (B) Fatty acid composition of S. cerevisiae transformed with either CSFAD2A cDNA or an empty vector (pESC-TRP) control. Each value is the mean±SD from three independent experiments. (C) Fatty acid composition of seed oil from homozygous csfad2a-1 ($BC_2F_1$) and (D) homozygous csfad2a-2 ($BC_1F_1$) plants compared to respective segregating heterozygous and wild type plants from the same generation as detailed in Table 2. Each value is the mean±SD from 8 to 28 seeds from the same line and generation;

FIG. 12 Nucleotide sequence encoding CSFAD2A (SEQ ID NO: 1);

FIG. 13 Amino acid sequence of CSFAD2A (SEQ ID NO: 3);

FIG. 14 Nucleotide sequence encoding CSFAD3A (SEQ ID NO: 2);

FIG. 15 Amino acid sequence of CSFAD3A (SEQ ID NO: 4); and

TABLE 1

Figure 2A:
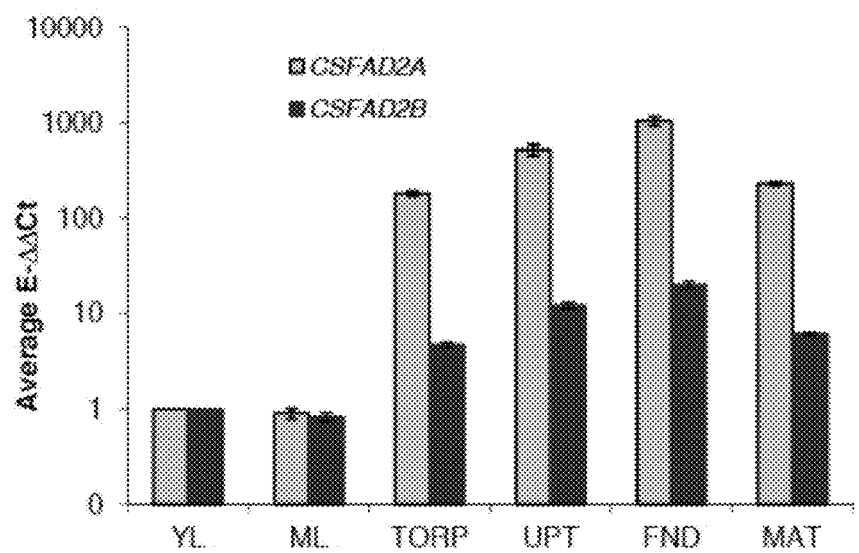

Nucleotide sequences, exon number and source of soluble and membrane bound desaturases from *C. sativa*;

| gene name | class | genomic sequences | exon number | nucleotide (ORF) derived from genome sequence |
|---|---|---|---|---|
| CSSACPD-A (SEQ ID No 34) | delta9 | FN1_14572637 | 3 | ATGGCTCTCAAACTCAACCCCACCATCGCTCAATCTCCAA AGTTACCAGCTTTTGCTCTTCCACCAATGGCTAGCCTCAG ATCTCCCAAGTTCTTCATGGCCTCCACCCTCCGTTCTGGC TCCAAAGAGGTTGATAATATCAAGAAGCCTTTCACTCCTC CTAGAGAGGTCCATGTTCAAGTAACACATTCCATGCCACC TCAGAAGATTGAGATCTTTAAGTCATTGGAAGATTGGGCT GATCAGAACCTTTTGGTTCACCTTAAGCCAGTTGAGAAGT GCTGGCAACCTCAGGATTTTCTCCCTGAACCATCATCTGA TGGATTTCATGAGCAGGTGATGGAACTTAGGGAGAGGGCT AGGGAGCTTCCTGATGATTACTTTGTTGTTCTGGTTGGTG ATATGATCACAGAAGAAGCACTCCCAACTTATCAAACTAT GCTTAATACATTGGATGGAGTTAGGGATGAAACTGGTGCC AGCCCAACTTCTTGGGCTATTTGGACTAGAGCATGGACTG CTGAAGAGAACAGGCATGGTGACCTCCTCAACAAGTATCT TTACCTCAGTGGACGAGTCGATATGAGGCAAATTGAGAAG ACCATTCAGTATCTGATCGGTTCTGGAATGGATCCCCGGA CAGAGAACAATCCTTATCTTGGTTTCATCTACACTTCATT CCAAGAAAGAGCCACCTTTATCTCACATGGTAACACTGCC AGGCTAGCAAAGGAGCATGGGGACTTAAAATTGGCACAAA TATGTGGTACCATAGCTGCAGACGAGAAGCGCCACGAGAC AGCCTACACTAAGATAGTTGAGAAGCTATTTGAGATTGAT CCTGATGGGACTGTGTTAGCATTTGCTGACATGATGAGGA AGAAGATAGCCATGCCAGCACACTTGATGTACGATGGCCG AGATGACAATCTTTTCGATAACTTTTCTGCTGTTGCACAA CGGCTTGGAGTGTACACGGCCAAGGATTACGCGGACATAT TGGAGTTCTTGGTTGGGAGGTGGAAGGTGGAGAAGCTAAG TGGACTTTCCGGGGAGGGGCTTAAGGCTCAGGAGTATGTT TGCGGGTTACCTCCAAGAATCAGAAGGCTGGAGGAAAGAG CTCAAGGAAGGGTGAAACAAGCTAGGAGTGTACCCTTCAG TTGGGTATATGATAGACAAGTGAGTCTCTAA |
| CSSACPD-B (SEQ ID No 35) | delta9 | FN1_14548126 | 3 | ATGGCTCTCAGACTCAGCTCAACGATCAACTTCCCAACTC ACAACGTCTCTTCTAAGCCTCACACTCTCAGATCTCCAAG GCTCTGCATGGCCTCCACTCTCCACTCCATTTCTAAAGAG ACTGAAAATGGAAAAAAGCCTTATTCGCCTCCGAAGGAGG TACATCTTCAAGTGACTCATTCACTACCACCTCAAAAGGT TGAGATCTTCAAGTCATTAGAAGGCTGGGCTGAAGATAAC ATTTTGGTGCACTTGAAACCTGTGGAGAAATGTTGGCAGC CACAAGATTTTCTACCCGAGCCGGAATCTGAAGGGTTTTA TGATCAAGTCAGGGAGTTAAGGGAAAGGGCGAAAGAAATT CCCGATGACTATTTTGTTGCGTTGGTCGGTGATATGATCA CTGAAGAAGCTCTACCGACATACCAGACAATGCTTAATAC TTTAGACGGGGTTAGAGATGAGACCGGTGCAAGCCCTACT TCTTGGGGAATATGGACCAGGGCGTGGACTGCTGAGGAGA ATAGGCATGGAGACCTTCTCAACAAGTATCTGTATCTCTC TGGAAGGGTTGATATGAAGCAAGTTGAGAAGACCATCCAA TATCTCATTGGCTCAGGAATGGATCCCAAAACGGAAAACA ACCCGTATTTGGGTTTCATCTACACCTCCTTTCAAGAGAG GGCTACATTCATCTCCCATGGAAATACTGCCAGGCAAGCC AAAGAGCACGGTGACCTGAAACTGGCGCAGATATGCGGCA CAATTGCTGCCGATGAGAAACGCCATGAAACTGCCTACAC AAAGATTGTGGAGAAGCTCTTTGAGATTGACCCGAATGGC |

TABLE 1-continued

Nucleotide sequences, exon number and source of soluble and membrane bound desaturases from *C. sativa*;

| gene name class | genomic sequences | exon number | nucleotide (ORF) derived from genome sequence |
| --- | --- | --- | --- |
| | | | ACTGTTATGGCTTTTGCTGACATGATGAAGAAGAAGATAT CGATGCCTGCCCACTTGATGTACGACGGGAAGGATGACAA TCTTTTCGATCACTTTGCAGCAGTTACACAGAAGCTTGAA GTTTACACTGCCAAGGATTATGCTGATATCATGGAGTTTC TGGTTGGAAGATGGAAGATTGAGAAATTGAGTGGTCTTTC GAGTGAGGGCCACAGAGCACAAGATTATGTGTGTAAATTG CCCCAGAGGATAAGAAAGTTGGAGGAGAGAGCTCAGGGAA GGACCAAGCAAGCATCAATGGTTCCTTTCAGCTGGATATT TGGTAGAGAAATCAAGATTTGA |
| CSSACPD-C delta9 (SEQ ID No 36) | FN1_14565533 | 2 | ATGCACGCAGGAGCCTCCTCTTCTTACCTTAGAAATCTTC AATGGGCCCAACCCAACGGCCCAATAAGCCCAAAAACACT CCCACTGAACCCCTACGTCAGTTTCCGAGTCTCCGCCGTG GCAGCCCCACCGCCGCAGCTAAAGTTTCAGAGAACGCATT CGATGCCGCCAGAGAAAGTTGAAATCTTTAAGTCGTTAGA AGGTTGGGCCTCCAAATCTGTTCTGCCATTGTTGAAGCCC GTGGACCAATGCTGGCAGCCTCAAGATTTTTTACCCGACC CGGCTAAGACTAGAGAAGAGTTCTTTGATCAGGTCCGTCA ATTGCGTGATCGGACGGTCGAGCTTCCAGATGAGTTTTTC GTTGTGTTAGTTGGGGATATGATCACGGAGGACGCATTGC CTACGTACCAGACCATGATAAATACCCTGGACGGCGTTAA GGACGAGACCGGAGCTAGCTCAAGCCCATGGGCCCAATGG ACTCGGGCCTGGACCGCCGAAGAGAATCGCCACGGTGATT TGCTTCGAACTTATCTGTATTTAACGGGTCGGGTCGATAT GACCATGATCGAAAGAACCGTCCAGTACCTGATTGGAGCT GGCATGGATCCGGGAACAGAGAACAGTCCGTACTTGGGAT TTGTGTACACGTCATTCCAAGAACGTGCCACGTTTGTGTC ACATGGCAACACAGCACGCATGGCAAAGGAGAGCGGGGAT CCAGTGTTGGCGCGTATATGCGGGACCATTGCATCCGACG AGAAACGCCACGAGAATGCCTATTCCAAGATCGTTGAGAA GCTTCTAGAAGTGGACCCCAACAATGCCATGCTGGCAATC GCTGATATGATGAGGAAGAAAATAACAATGCCGGCTCACC TTATGTACGATGGACGGGACCCTATGATATTTGAGCACTT CTCGGCTGTGGCTCAGCGGCTCGGTGTGTATACGGCTGAT GATTACGCTGATATCTTGGAATTCTTGATCGGGCGGTGGA GGTTGGAGAAGATGGTGGGGTTGTCGGCTGAGGCTCAGCG AGCTCAGAACTATGTTTGTGGGTTGGCGCCCAGGATTAGG AAGCTGCAGGAGCGAGCCGATGATCGGGCGCGTAAGATGG AGCCACAAAGTGTCAAGTTTAGCTGGATATTTAATAAGGA AGTCCTCTTGTAA |
| CSSACPD-D delta9 (SEQ ID No 37) | FN1_14539699 + FN1_13882113 | 2 | ATGCAAGTACAGGTCAGTAATATTTCATTGTGGGCCTTAA ATGGCCACCAAAGCCCAAACAAGCTCCAACTGAGAAGCCC ATCACCAAAACCCAGATTCCAAGTCTCAGCCGTGGCCTCA CCACCGCGGCCGATGAAACTCCATCAGCCAACGATGCCGC CGGCTAAAGAAGAAGTGTTCAAGTCGCTAGAAGGGTGGGC CACCCAATCGATTCTTCCACTGCTAAAGCCGGTGGAGGAA TGTTGGCAGCCCCAAGACTTTTTACCCAACCCATCAAATT CTGACGAAGAATTCTTCGATGAGATCCGTTTGATTCAAGA TCGTGCGGCTGAGATTCCAGATGAGTACTTTGTTGTCTTG GTTGGAGATATGATCACGGAGGAAGCATTGCCTACTTACC AGACCATTATGAACTCTATTGATGCCGTTAAGGATAGGAC TGGAGTTTGCTCCAGTCCATGGGCTCGGTGGACCCGCGAG TGGTCCGCCGAGGAGAATCGGCACGGTGACTTGCTTCGTA CGTATTTATACTTATCGGGTCGGGTCGATATGACCATGGT TGAACGGACTATCCAACATTTGATTGGAGCTGGCATGAAT GGAAATTTCAACAACAATCCATACTTGGGTTATGTGTACA CATCATTTCAAGAGCGAGCAACATTTGTGTCGCATGGCAA CACAGCTCACTTAGCGAAAAAGAGCGGAGATCCACTCTTG GCGCGCATTTGCGGAACTATTGCAGCCGATGAGAAGCGAC ACGAGATTGCTTACGTAAAAATGACCGAGAAGCTCTTAGA AGTTGACCCAAATAATGTCATGCTCGCAATCGAGGAAATG ATGAGGAGAAAGATCACAATGCCGGCCGCCCTTATGTACG ATGGATGCGACCCCATGTTATTCCACCACTTCTCGGCTGT GGCTCAGCGCCTCGGCATCTACACAGCTGATGACTACGCC GACATCTTGGAGTTCTTAATCAAAAGGTGGAGGTTAGAGA AGATGGAAGGGTTGAATCCCGAGGCTCAAAGGGCGCAAGA CTTTGTTTGTGGCCTTGCGCCGAGAATTAGGAAGCTTCAA GAGCGAGCTGATGAGCGTGCACAAAAGATGGAGCCTCTTA GTGTCAAGTTTAGTTGGATTTTTAACAAAGAGGTTCTTGT GTAG |

TABLE 1-continued

Nucleotide sequences, exon number and source of soluble and membrane bound desaturases from C. sativa;

| gene name | class | genomic sequences | exon number | nucleotide (ORF) derived from genome sequence |
|---|---|---|---|---|
| CSSACPD-E (SEQ ID No 38) | delta9 | FN1_14576833 FN1_13944518 | + 2 | ATGCAAGTACTACAAGTTTCATGGCAGGCCTTAAGTGGCT TCCAAAGCCCAAAAAATCTCCAACTGAGAAGCCCATCACC AAAGCCCAGATTCCGAGTCTCCGCCGTGGCCTTACCACCA CCACCGATGTCGCCGGATATAGAAGAAGTTTTCAAGTCAC TAGAGAGCTGGGCCACCCAATCAATTATCCCACTGCTAAA GCCGGTGGAGGAATCTTGGCAGCCCCAAGATTTGTTACCA AGCCCAACCTATAATAATGTCGAGGAAGAATTCTTCGATC AGATCCGTTCGATTCAAGATCGTGCGGCTGAGATTCCAGA TGAGTACTTTGTTGTCTTGGTTGGAGATATGATCACGGAG GAAGCATTGCCTACATACCAGACCATTATGAATTCTATTG ATGCCATTAAGGATAAGACTGGAGTTTGCTCCAGTCCATG GGCTCGGTGGACCCGCGCATGGTCCGCCGAGGAGAATCGC CATGGTGACTTGCTTCGTACCTATTTATATTTAACGGGTC GGGTAGATATGACCATGGTTGAACGTACTATCCAACACTT GATTGGAGCTGGCATGGATGCAAGATTCAACAACAATCCA TACTTGTTTTACGTGTACACATCATTTCAAGAACGAGCCA CGTTTGTGTCCCACGGCAACACGGCCCGCTTAGCGAAAAA CAACGGAAACCCACTCTTGGCGCGCATTTGTGGGACTATT GCGGCCGATGAGAAGCGTCACGAGATTGCGTACGTAAAAG TGACCGAGAAGCTCTTAGAAGTTGACCCAAATAATGCCAT GCTAGCAATTGAAGAAATGATGAGGAGAAAGATCACAATG CCGGCCTTCCTTATGTACGATGGATGCGACCCCATGCTAT TCCACCATTTCTCGGCTGTGGCTCAGCGCCTCGGCGTCTA CACAACTGATGACTACGCCAACATCTTGGAGTTCTTAATC GGACAGTGGAAGTTAGAGAAGATGGAAGGGTTGAAACCTG AAGCTCAAAGAGCGCAAGACTATGTTTGTGGCCTTGCACC GAGAATTAGGAGGCTGCAAGAGCGAGCTGATGAGCGCGCA CGGAAGATGGGGCCTCTTAGTGTCAAGTTTAGTTGGGTTT TTAACAAGGAGGTTCTTCTCTAG |
| CSFAD2A (SEQ ID No 39) | delta12 | FN1_7054927 | 1 | ATGGGAGCCGGTGGCCGAATGCCCGAGGCGAAATCCGAGT TGAATGGTAGTAAGAATAATAATAGGCTAATTGAGAGAGT ACCACACACCAAACCACCATTCACATTAAGCGAAATCAAG AAAGCAATTCCGCCCCATTGCTTTAAACGCTCTCTAATTC GCTCTTTTGCTTGTGTCTTTCACGACCTTTTTTTCGCGTC ATTGTTTTACTATGTTGCAACCTCTTACTTTCACCTTATC CCGAAACCAATTTCATACATTGCTTGGCAATTTATTGGA TTTTCCAAGGTTGTATTTTGACCGGGGTTTGGGTCATCGC TCATGAGTGTGGTCACCATGCTTTTAGTGACCACCAGTGG GTGGATGACACCGTTGGTCTCATCCTCCACTCTGCTCTTC TTGTCCCATATTTTTCATGGAAGTATAGTCATCGTCGCCA CCACTCAAACACGGGGTCCATTGATCGCGACGAAGTGTTT GTACCAAAACCAAAATCACAAGTGTCACCATTCGCCAAAT ACTTAAACAATCCACCCGGGAGAGTCTTAAGCCTTTTTGT TACCCTAACACTTGGTTGGCCTTTGTACTTAGCTTTCAAT GTATCAGGCAGACCATATGACCGTTTCGCTTGTCATTATG ATCCCTATGGCCCAATCTACTCAAACCGCGAAAGGTTACA AATATTCATCTCGGACATAGGGATTTTCATTGCCACATTC GCGCTATACCACCTTGTCTCGGCCAAAGGGTTAGGTTGGG TTGTGTTAGTGTATGGTGTGCCTTTGTTAATAGTAAATGG CTTCCTTGTTTTGATCACTTACTTGCAACACACTCACCCT GCATTGCCTCATTATGACTCGTCCGAATGGGATTGGTTGA GAGGAGCATTGTCAACCGTTGATCGAGACTATGGAATTCT CAATAGGGTTTTTCACAACATTACTGACACTCATGTTGTG CACCATTTATTCTCAACAATGCCACATTACAATGCAATGG AAGCAACCAAAGCTGTGAAGCCGATATTAGGCGAGTACTA CCGTTTAGATGACACTCCAATTGTTAAGGCTATGTGGAGA GAAGCTAAAGAGTGTCTCTATGTTGAGCAAGATGATGATT CTCCATCTAACAAAGGTGTTTTTTGGTACAAAAACAAGTT TTAG |
| CSFAD2B (SEQ ID No 40) | delta12 | FN1_4063495 | 1 | ATGGGAGTTAAAAGTCGAATGCTCGAGCCAAAATCCGAGT TGAAAGATAGTAAGAACAATAATAATAGCCCAATTGAGAG AGCACCACACACTAAACCACCATTCACACTAAGCCAAATC AAGAAAGCCATTCCACCCCATTGCTTCCAACGCTCTCTTC TTCGCTCCTTCTTTTATGTCTTTCGAGACCTTTTCTATGT CACTTTGTTCTACTACTTAGCAACCTCTTACTTCCACCTT CTCCCCCATCCACTCCCATACCTAGCTTGGCCACTTTATT GGATCTTCCAAGGTTGTGTTTTGTTTGCTTTCGGGCTCAT TGGTCATGAATGTGGTCACCATGCCTTTAGTGACTACAAA TGGATTGATGACATGGTTGGTTTTGTTATCCACTCTGCAA TTCTTCTCCCATACTTCTCATTTAAGTATAGTCACCGTCG CCACCATTCAAACACTGGATCCATTGATCGCGATGAAGCT TTTGTTCCAAAGACGAAATCTCAAATGCCATGGTTCTCCA |

TABLE 1-continued

Nucleotide sequences, exon number and source of soluble and membrane bound desaturases from *C. sativa*;

| gene name | class | genomic sequences | exon number | nucleotide (ORF) derived from genome sequence |
|---|---|---|---|---|
| | | | | AATACTTAAACAATCCATTAGGAAGAGTCCTAACCCTAGG<br>TTTTCTATTAACCGTCGGTTTTCCTTCATACTTAACTTTC<br>AATATATTAGGCAGACGATATGACCGTTTCGCTTCTCATT<br>ATGATCCTTACTCTCCTATATACTCCAACAATGAAAGGCT<br>TCAAATATTAATTTCCGATGTGGGGGTTTTCATCACCACA<br>TTCGTGTTGTACCAACTCGCCTTAGCAAGAGGGTTGAGTT<br>GGGTTATGTTAGTGTATGGGGTGCCAATGGTATTAGTGAG<br>TGGTTGGCTTGTTTTGGTCACTTACTTACAACACACTCAC<br>CCTGCATTGCCTCACTATGATTCTTCCGAATGGGATTGGT<br>TGAGAGGTGCTTTGTCGACAGTTGATCGAGACTTTGGAGT<br>GCTCAATAGTATTTTTCATAACATTTCAAACACTCATGTT<br>GTGCACCATTTATTCCCCACAATACCATATTACAATGCAG<br>TGGAAGCAACTAAAGCTGTGAAGCAATATTAGGAGAGTA<br>CTACCGTTTAGATGAGACTCCAATAATTAAAGCTGTGTGG<br>AGAGAGGCAAAAGAGTGTCTCTATGTTGAGAGTGATGATG<br>AGTCTCCTCTTTACAAAGGTGTTTTTTGGTATAAGAACAA<br>GTAA |
| CSFAD2C (SEQ ID No 41) | delta12 | FN1_14553312 | 1 | ATGGGAGTCAATGGTGAAAATAGTAGACTTGATCGAGCAC<br>CACACACCACGCCATCATTCACACTAAGCCAACTCAAGAA<br>AGCCATTCCACCCCATTGCTTCAACCGTTCTCTTCTCCGA<br>TCCTTCTCTTATCTCCTTCGAGACCTTTTTTTCGCCTCTT<br>TGTTCTACTACGTAGCAACTTCTTACTACCACCTTTTCCC<br>TCAACCACTCTTATACTTTGCTTGGCCACTTTATTGGGTC<br>TCCCAAGGCTGCATTTTATTCGGCTTAGGGCTCATTGGTC<br>ATGAGTGTGGTCACCATGCCTTTAGTGACTACAAATGGGT<br>TGATGACATGGTTGGTTTCGTTATTCACTCTGCTTTTCTT<br>CTCCCATACTTTTCGTTTAAGTATAGTCACCGACGCCACC<br>ATTCAAACACTGGCTCCATTGACCGCGATGAAGCCTTTGT<br>TCCAAAGACGAAATCTCAAATGCCATGGTTCTCTAAATAC<br>TTGAACAATCCACTAGGGAGAGTCCTAACACTTGGTTTCT<br>TTTTAACCATTGGTTGGCCTTTGTACTTAGCTTGCAATAT<br>ATTAGGTAGACCATATGACCGTTTCGCTTGTCATTACGAT<br>CCTTACTCTCCAATATACTCAAAAAATGAAAGGCTTCAAA<br>TATTGATTTCAGATATTGGTGTTTTCATCACCACATTGGT<br>GTTACACCAACTTGTCTTAGCCAAAGGATTGAGTTGGGTT<br>TTGTTCGTGCATGGGATACCATTGCTAATAGTAGGTGTCT<br>TGCTAGTTTTGACCACTTATTTACAACACACTCACCCTGC<br>ATTGCCACACTATGACTCGTCCGAATGGGATTGGTTGAGA<br>GGTGCTTTGTCAACCGTTGATCGAGATTTTGGAGTTCTCA<br>ATAGTATTTTTCATAACGTTTCAAACACTCATGTGTTGCA<br>TCATTTATTCCCCAAAATACCACATTACAATGCAATAGAA<br>GCAACAAAAGCTGTGAAGCAATATTAGGAGAGTACTATT<br>GTTTAGATGAGACTTCAATAATTAAGGCTATGTGGCGAGA<br>GGCCAAAGAATGTCTTTACGTTGAATCAGATGATGAATCT<br>TCGAAAAAGGTGTTCTTTGGTACAAGAACAAACTTTGA |
| CSFAD2D (SEQ ID No 42) | delta12 | FN1_14570259 | 1 | ATGGAAGTTGTAGATGACCAATATAGTAACCTTGTTAGGC<br>GAGCACCACACACCGAACCACCATTCACGCTAAGCGAAAT<br>CAAGAAAGCCATTCCACCCCATTGCTTCAAACGCTCTCTT<br>CTCCGCTCCTTCTCTTATCTCCTTCAAGACCTTTTCTTAG<br>TCTCTTTACTCTACTACATAGCAACATCTTACTTCCACCT<br>TCTTCCTCATTGCCCATTTTCATACTTAGCTTGGCCCCTT<br>TATTGGATCTCCCAAGGCTGCATCTCATTTGGTATTTGGG<br>TCATTGCTCATGAGTGTGGCCACCATGCTTTTAGTGATCA<br>CCAATGGGTGGATGACACCGTTGGTTTCGTCCTTCATTCC<br>GCTCTTCTCTTCCCATATTTCTCTTGGAAGTATAGTCACC<br>GTCGCCACCACACCAACACTGGCTCCATGGAGCGCGATGA<br>AGTGTGTGTCCCAAAGCCGAAATCTCAAATGTCATGGCTC<br>TACAAATACTTGAACAATCCATTAGGGAGAGTCCTAAGAC<br>TTAGTGTTACATTGTTCCTTGGTTGGCCTCTTTACTTAGG<br>GTTCAATGTATCAGGTAGATCATATAACCGTTTCGCTTGT<br>CATTTTGATCCTTACTCCCAATCTTCACAAAAAGGGAAA<br>GGCTTCAAGTATTAATTTCAAATTTTGGTGTTTTAATTAC<br>TATATTTGTATTGTACCAACTCAGCTCAACCAGAGGGTTG<br>AGCTGGGTTGTATTCGTGTACGGGGTGCCATTGCTTATAG<br>TCAATGGCACCATTTCTTTGATGACATATTTGCATCACAC<br>TCACCTTGCATTGCCTCACTATGACTCGTCCGAATGGGAT<br>TGGTTAAGGGGTGCTTTGTCAACAGTCGATCGAGACTATG<br>GAGTTTTCAATAGAATTTTTCATAATGTTACAGACACTCA<br>TGTATTGCACCATTTATTCTCAACAATACCTCATTACAAT<br>GCAATGGAAGCCACCAAAGCTATTAAGCCAATATTGGGAG<br>AGTACTATTGTTTCGATGAGACTTCGATAATTAAAGCTAT<br>GTGGAGAGAGATTAAGGAGTGTGTCTATGTTGAACCAGAT |

TABLE 1-continued

Nucleotide sequences, exon number and source of soluble and membrane bound desaturases from *C. sativa*;

| gene name | class | genomic sequences | exon number | nucleotide (ORF) derived from genome sequence |
|---|---|---|---|---|
| | | | | GATGAATCTTCTTCTAATAAAGGTGTTTTAATGGTATAAG AACAAGTTCTAA |
| CSFAD2E (SEQ ID No 43) | delta12 | FN1_14530645 | 1 | ATGGGAACTGAAGGTGGCCAATATAGTAGAGTTGTGAGAG CACCACACACCAAACCACCATTCACACTAAGCCAAATCAA GAAATCCATTCCGCCCCATTGCTTCAACCGCTCTCTTCTC CGTTCCTTCTCTTATCTCCTTCGAGACCTTTTTTTCGCCT CTTTATTCTACTACGTAGCAACCTCTTACTTACACCTTCT CCCACACCCACTTTTGTACATGGCTTGGCCACTTTACTGG ATCTCCCAAGGCTGCATTTGTTTCGGTATTTGGATCATTG CTCACGAGTGCGGTCACCATGCTTTTAGTGACCACCAATG GGTGGATGACACTCTTGGCTTTATCTTCCACTCTGCTCTT CTCGTCCCATACTTCTCATGGAAGTATAGTCACCGTCGCC ACCATTCCAACACCGGCTCTATTGAGCGCGATGAAGTGAT TGTTCCAAAGAGAAAATCACAAATGCCATGGCATTACAAA TACCTCAACAATTCATTAGGGAGATTCTTAAGGCTTGGTC TTACCGTGATTTTCGGTTGGCCTTTGTATGTGTGTTTCAA TGCATTAGGTAGACCATATGATCGTTTCGCTTGTCATTTT GATCCTTACTCTCCAATCTACTCAAAAAGCGAAAGGCTTC ATATACTAATTTCAGATATTGGTGTTTTAATTACCATATT TTTATTGTACCAACTCAGCTCAGTTAAAGGGTTGAGTTGG GTTGTGATCACGTACGGGATGCCATTACTAGTAGTAAATA GCATCCTTGCGGTGATCACATACTTGAATCACACTCACCT TGCATTGCCACATTATGACTCGTCGGAATGGGATTGGTTT AGGGGTGCTTTGTCAACGGTTGATCGAGATTTCGGAGTTC TCAATGGGGTTTTTCATAACATCACAAACACTCATGTGGT GCACCATTTATTCTCAACAATGCCACATTACAATGCAGTG GAAGCAACCAAAGCTGTGAAGCCAATATTGGGAGAGTATT ATTGTTTTGATGACACTCCGGTAATTAAAGCTATGTGGAG AGAGGTTAAGGAGTGTGTCTATGTTGAGTCAGATGATGAA TCTTCTAATAAAGGTGTTTTATGGTATAAGAACAAGTTCT AG |
| CSFAD2F (SEQ ID No 44) | delta12 | SAT3_scaffold7 1447 | 1 | ATGGGAGCCGGTGGCAAAAATAGTAGACTTGAGCGAGCAC CACACACCACACCACCATTCACACTAAGCCAACTCAAGAA AGCCATTCCACCCCATTGCTTCAACCGTTCTCTTCTTCGT TCCTTCTCTCATGTCCTTCAAGACCTTTTTTTCGTCTTTT TGTTCTACTACATAGCAACCTCTTACTTCCATCTTCTCCC ACACCCGCTCCAATACTTAGCTTGGCCACTTTATTGGATC TTCCAAGGCAGCATTTTTGCTGGTATTTGGGTCCTTGGTC ATGATTGTGGTCACCAAGCTTTCAGTGACCACCAATGGGT GGATGACACTGTTGGCTTTGTCCTCCACTCCGCTCTTCTC TTCCCATACTTCTCTTTTAAGTATAGTCATCGTCGCCATC ATTCAAACATCGGCTCCCTTGAACATGATCAATTGTTTGT TCCAGTCCCCGAATCTCAAATCGCATGGCTCTACAAACAT TACTTGGACAATCCACTAGGAAGAGCCCTAAAGCTTTCTA TTATAGTGTTCCTTGGTTCTCCTTTGTACTTAGGTTTCAA TCTTACAGGCAAACAATATGATCGTTCTGCATGTCATTAT GATCCTTACTCTCCACTCTACTCAAAAAGTGAAAGGCTTC ATATATTGATTTCAGATATCGGTGTTTTCATCACCACATT GGTGTTATACCAGCTTGGCTCGACTAAAGGGTTGAGTTGG CTTGTGTTCATGTATGGGGTGCCATTGTTTACAGGGAATA GCATCCTTGTGACAATCGCATACTTGAATCATACTCACTC TTCATTGCCTCATTATGACTCGTCAGAGTGGGATTGGTTG AAAGGAGCATTGTCAACAATTGATCGAAACTATGGATCAA TTCTCAATAGGGTTTTCCATCACCTTACAGATGCTCATAT GGCACACCATTTATTCGCAACAATACCTCATTACCATGCA AATGAAGCCACCAGAGCTATCAAACCCATATTGGGA |
| CSFAD2G (SEQ ID No 45) | delta12 | FN1_14504247 | 1 | ATGGGTGCCGGTGGTCGAATGAATGTTCCTCCAGGCTCAA AAAAATCAGAGGCCGAAAGCCTTAAACGAGTTCCACACAC AAAACCACCATTCACACTTGGCGAAATCAAGAAAGCCATT CCACCCCATTGTTTCCAGCGCTCTGTTGTTCGCTCATTCT CTTATGTCGTTTATGACCTTACCATTGCTGCCATCCTTTA CTATATTGCTACTCGTTACATCCCCCTCCTCCCACACCCT CTGTCTTACCTGGCTTGGCCCATTTATGGGTTCATCCAGG GTTGTGTCCTAACTGGTGTTTGGGTCATAGCCCACGAGTG TGGCCACCACGCCTTTAGTGACCACCAATGGCTTGACGAT ACCGTGGGCTTAGTCCTTCACTCTTTCCTTCTCGTCCCCT ACTTTTCATGGAAATACAGCCACCGTCGCCACCATTCCAA CACAGGCTCTCTTGACAAAGATGAAGTCTTTGTTCCCAAG AAAAAGTCTGCCATGAAATGGTACTCTAAATACCTCAACA ATCCCCCTGGCAGATTCCTCACTCTAACAATCACTCTCAC TCTGGGCTGGCCTCTTTACTTGGCCTTCAATGTCTCGGGC |

TABLE 1-continued

Nucleotide sequences, exon number and source of soluble and membrane bound desaturases from *C. sativa*;

| gene name | class | genomic sequences | exon number | nucleotide (ORF) derived from genome sequence |
|---|---|---|---|---|
| | | | | CGGCCCTATGACCGTTTTGCATGCCACTTCGATCCATACG GCCCAATCTACTCGGACCGTGAGCGGGCCCAGATATACCT ATCTGATGTGGGCATTCTCGCAATGTGTTTCGGCCTTTAC AAGCTGGCTATGGCAAATGGGCTTGCTTGGGTTTTATGCG TGTATGGAGTCCCATTGTTGGTGGTGAATGGGTTTTTGGT GCTGATCACTTTCTTGCAACACACTCACCCATCGTTGCCT CATTACGATACATCGGAGTGGGATTGGCTTAGGGGAGCTT TGGCTACAGTGGACAGAGATTACGGTTTGTTGAACAAGGT CTTCCATAACATCACAGACACCCATGTGGCTCACCACTTG TTCTCCACAATGCCTCATTATCATGCCATGGAGGCCACAA AAGCTATCAAGCCAATACTTGGAGAGTACTACCAATTTGA CGGAACACCAGTGTACAAAGCCATGTGGAGAGAGACTAAG GAATGTGTTTTTGTCGAAGCGGATGAAGGTGAAGGCAAAG GTGTCTTCTGGTACAACAAGCTTCGGGATTGA |
| CSFAD3A (SEQ ID No 46) | delta15 | FN1_13245263 | 8 | ATGACAGAATCACATGCTTCGGAGGAAATGGCGAGAGAAG AAAAAGGTGACTACCCCATTAAGGTGGCAAATGGGATCCG AAACCAAAACGGCGATTTCGATCTGAGTGATCCTCCACCG TTTAAGATAGCTGAGATCCGAGCCGCCATTCCTAAGCATT GTTGGGTTAAGAATCCATGGCGCTCACTCAGCTATGTTTT CAGAGATCTCTTTATCATTTTTGCATTGGCCTTTGCCGCT TTCTATTCCGATACTTGGGTCGTTTGGCCATTTTACTGGG CTGCTCAAGGAACCATGTTCTGGGCTCTCTTCGTTCTCGG CCACGATTGTGGCCATGGAAGCTTTTCAAACAGTCCTGAG CTGAATAGCGCTGTGGGTCATATTCTGCATTCTGCAATCC TTGTACCTTACAATGGATGGAGAATTAGCCATAGAACTCA TCATCAAAACCATGGCCATGTTGAGAATGACGAGTCATGG GTTCCGTTGACTGAGAAGATGTACAAACAGTTGGATGAGA AAACAAAGAGGCTGAGATTCAAAGTCCCATTTCCCTTATT TGCATACCCTTTTTATCTGTGGAATAGAAGTCCAGGAAAA GAAGGCTCTCATTTCAATCCTTACAGCAAATTATTTACTC CAAGTGAGAGAAACCAAATAATAACTTCAACGGTTTGCTG GTCAACAATGGCTGCTTTGCTTGTCTGTTTGTCCTTCATA GTAGGTCCTGTTCAAGTTCTCATGCTATATGTTGTTCCTT ATTGGATATTTGTGATGTGGCTAGACATTGTCACTTACTT GCATCACCATGGTTATGAGCAAAAACTCCCTTGGTACCGG GGCAAGGAATGGAGTTACCTAAGGGGAGGGCTAACAACAG TAGACCGTGACTATGGAATATTTAACAATATCCACCATGA CATTGGAACTCATGTTATACACCATCTCTTCCCTCAAATC CCACACTACCATCTTGTGGAAGCTACCAAGGCAGCCAAGC CAGTGCTCGGAAAGTATTACAGGGAGCCTAGAAAGTCAGG GCCAATTCCAGTCCACTTGATCGAGAATCTAGTTAAGAGC ATCAGCCAGGACCACTATGTGAGTGACAATGGCGAAGTAG TATACTACCAGACAGACCCAGAACTTAATAATAATAATAA TAAAAAATATCTGAGGCCAAGCAAATGTAG |
| CSFAD3B (SEQ ID No 47) | delta15 | FN1_14584234 | 8 | ATGGCGAGTTGGGTTTTGTCAGAATGTGGATTAAAGCCAC TCCCTCAAAATTTTCCTCGACCCAGAACAGGGATTACCTC AACCAACCCAACAACAAAGACTCGGTTTTTGAGTTCTAAC AAGAGCTCGGCGGATCTTAGATTCCCAAAGGTGAATTTCT CAACTGGGTTTTTGAAAAGGAGGAGTTTTGAGGTGAGAGT GAGCGCGCCCATTGAAGGTTGCTTTTGTAGAAGAGGAAGAC AGAGGAGAGAGAGTAGAGGAAATCGTTAATGGAGTTGAAG AAGAAGAAGAAGAGGGAATCAAATTTGATCCTGGCTCGGC TCCACCCTTTCAAATTGGCTGATATTCGGGCTGCTATTCCA AAACATTGTTGGGTTAAGGATCCATGGAAGTCTATGAGCT ATGTGGTGAGAGATGTGGCTATCATATTTGGGTTGGCTGC GGCTGCTGCTTCTATTAACAACTGGGTTGTTTGGCCTTTG TACTGGGCTGCTCAGGGGACTATGTTTGGGCTCTATTTG TTCTTGGTCATGACTGTGGCCATGGAAGCTTTTCAAACGA TCATAAGCTAAACAGTGTAGTTGGGCATCTCTTGCATTCC TCAATTCTTGTACCTTATCATGGATGGAAAACTAGCCATA AAACCCATCACCAAAACCATGGACATGTTGAGAATGATGA ATCATGGCATCCGTTACCTGAAAGAATTTACAGGAAACTG GATAACATCACAAAAAGTTTGAGATTTACTCTACCATTTC CAATGCTTGCTTATCCTTTCTACCTTTGGGGAAGAAGTCC AGGAAAGGCTGGTTCTCATTTTCATCCAAATAGTGACTTG TTTGTTCCAAGTGAGAAGAAAGATGTGATCACTTCCACTT TATGTTGGACAGCTATGGCTGCTATACTTGTTGGTTTGGG CTTTGTGATGGGTCCTATTCAATTGCTTAAGCTCTATGGC ATTCCTTATTGGGTTTTTGTCATGTGGCTGGATTTAGTGA CATACTTGCATCACCATGGCCATGAAGAAAAATTACCATG GTACCGCGGAAAGGAATGGAGTTACTTAAGAGGAGGGCTC ACGACACTTGATCGCGATTATGGAGTGATTAACAACATTC |

TABLE 1-continued

Nucleotide sequences, exon number and source of soluble and membrane bound desaturases from *C. sativa*;

| gene name | class | genomic sequences | exon number | nucleotide (ORF) derived from genome sequence |
|---|---|---|---|---|
| | | | | ATCATGATATTGGAACTCATGTAATCCACCATCTTTTCCC |
| | | | | TCAAATTCCTCACTACCACTTGGTGGAAGCAACCGAGGCA |
| | | | | GCTAAACCAGTGATAGGGAAATACTACAGAGAGCCGAAGA |
| | | | | AATCGGGTCCTCTACCGTTTCACTTGATAGGTGCTTTGAT |
| | | | | TAGAAGCTTGAAACAAGATCACTATGTTAGTGACACTGGT |
| | | | | GATGTTGTGTACTACAAAACTGATCCTGATCTTAAGTGA |
| CSFAD3C (SEQ ID No 48) | delta15 | SAT3_scaffold1 4620 | 8 | ATGGCGACTTGGGTCTTATCAGAATGTGGCGTAAAACCTC |
| | | | | TTCTTAGAGTCTACCCTCAACCCAGAACCGGAATGTTGTT |
| | | | | GAAGCCTTCCATCCCGTCGAGTCTTAGGACATTGCCGGTC |
| | | | | TGTAAGAGTAGCCAATTGGGTTTCTCATTGTCTTCCTCAA |
| | | | | GTGGGTTTAGGGGGCAGAATTGGAAACTTAATGTGAGTGC |
| | | | | TCCATTAAGAGTCTCTGATGTTGGTGAAGAAGATAATGAG |
| | | | | AAGAGGGTAGTGGAAGATGAAAGTGGATTCGACCCTGGTG |
| | | | | CGCCGCCTCCATTTAAGTTGGCTGATATTAGAGCAGCCAT |
| | | | | TCCTAAACACTGTTGGATTAAGGACCCATGGAGATCTATG |
| | | | | AGCTATGTTTTGAGGGACGTTGTTGTCGTTTTTGGTATGG |
| | | | | CGGCTGCGGCTGCTTATTTAAACAACTGGGCCGTTTGGCC |
| | | | | TCTGTACTGGATTGCTCAAGGAACCATGTTCTGGGCTCTT |
| | | | | TTTGTTCTTGGCCACGACTGTGGTCATGGAAGTTTTTCTA |
| | | | | ATAACGCAAACCTTAATAGCGTGGTGGGTCATATTCTTCA |
| | | | | TTCTTCAATCCTTGTCCCATACCATGGATGGAGAATAAGC |
| | | | | CACAGGACTCATCATCAGAACCATGGACACATTGAAAACG |
| | | | | ATGAATCTTGGCATCCGCTATCTGAGAAAATCTACAATAG |
| | | | | CTTGGATAAGGGTACCAAATTGCTGAGGTTTACCTTGCCT |
| | | | | TTCCCTATGCTTGCTTACCCTTTTTATCTGTGGAGTCGAA |
| | | | | GTCCCGGAAAGAAGGGTTCTCATTTTGATCCAAACAGTGA |
| | | | | CTTGTTTGTTGAGAGTGAAAGGAAAGACATCATCACCTCC |
| | | | | ACTGCATGTTGGACTGCCATGGTTGCTCTGCTCGGTGTGC |
| | | | | TCTCCTTTGTAATGGGTCCTGTTCAACTCATTAAGCTCTA |
| | | | | TATTGTTCCCTACTGGATTTTTGTCATGTGGTTGGACTTG |
| | | | | GTCACTTACTTGCATCATCATGGCCACGAGGACAAACTTC |
| | | | | CATGGTATCGTGGAAAGGAGTGGAGTTATCTAAGAGGTGG |
| | | | | ACTAACTACTCTTGACCGTGATTATGGATGGATCAATAAC |
| | | | | ATTCACCATGATATTGGAACTCATGTTATACATCATCTCT |
| | | | | TCCCTCAAATCCCACATTATCACTTAGTGGAAGCAACAGA |
| | | | | GGCAGCTAGACCTGTATTTGGTAAATACTATAAGGAGCCA |
| | | | | AATAAATCTGGACCTTTACCATTTCACTTGCTTGGAAGTT |
| | | | | TAATAAGAAGCATGAAAAAGGATCACTATGTTAGTGATAC |
| | | | | AGGGGATGTTGTTTACTACCAAACTGATCATCAAAGCTATAT |
| | | | | GGGCCTTCTGAATCTGACTCTTCCACATGA |
| CSD8 (SEQ ID No 49) | delta6/8 | FN1_14584615 | 1 | ATGGAAGCCGAGAAGAAGTACATTACCACTGAGGAACTGA |
| | | | | AGGAGCACAACAAGGCAGGGGATCTGTGGATCTCTATTCA |
| | | | | GGGTAAGGTTTATAATGTATCAGAATGGCTTAAGGATCAC |
| | | | | CCTGGTGGGGATGCGCCTCTACTAAGTTTCGCTGGCAGAG |
| | | | | ATGTTACTGATGCTTTTATTGCATACCATCCCGGTACTGC |
| | | | | GTGGAAGCATCTTGATCAGTTTTTCACCGGTTATTATGTC |
| | | | | AAAGATTTCGTGGTCTCAGAGATTTCCAAGGATTATAGGA |
| | | | | GAATTTCAAACGAGTTTACCAAACTGGGGTTGTTTGAAAA |
| | | | | GAAAGGTCATGGGATTTTCTACACTCTCACATGTGTTGCT |
| | | | | ATAATGCTTTCCATGGTTGTTTATGGTGTTGTGAAATCTG |
| | | | | AGAGCATTTTAGTCCATATGGGTTGTGCTGTCGTATTGGG |
| | | | | GATGCTTTGGATTCAAAGCGCTTATGTTGGGCATGATTCT |
| | | | | GGGCATTATCAGGTCATGTTAAGCCCTGGATATAACAAAT |
| | | | | TGCTCAGCTTTTGGCTGGGAATTGTCTTACTGGGATTAG |
| | | | | CATTGCTTGGTGGAAATGGACTCATAATGCCCATCATATT |
| | | | | GCTTGCAACAGCCTTGATTATGATCCAGATCTTCAACACA |
| | | | | TTCCCGTCTTTGCAGTGTCTTCTAAATTCTTCAAGTCCAT |
| | | | | TACTTCACGCTTTTATGGAAGGGAGTTGACATTCGATTCA |
| | | | | TTGTCTAGGTTCATGATCAGTTACCAACATTGGACATATT |
| | | | | ATCCAGTTATGTGTGTTGCCAGGGTTAACTTGTTTGTACA |
| | | | | GACACTATTGTTGCTCTTGTCAAAAAGACCTATCCCAAAT |
| | | | | AGAGCTTTGAACATAATGGGAACCCTTGTGTTCTGGACTT |
| | | | | GGTTCCCTCTCCTTGTTTCATGTTTGCCCACCTGGACAGA |
| | | | | GAGGACGATGTTTGTGCTCTTGAGCTTTGCAGTCACATCA |
| | | | | GTTCAACATGTTCAATTCACTTTGAACCATTTCTCAGCAG |
| | | | | ATGTTTATCTCGGTCACCCTGGTGGGAATGATTGGTTTGA |
| | | | | GAAGCAGGCTGCTGGGACTATAGATATTTCATGCTCACCT |
| | | | | TGGATGGATTGGTTCTATGGAGGGCTGCAGTTTCAGCTTG |
| | | | | AGCATCATTTGTTCCCACGCATGCCTCGTTGCCAATTGAG |
| | | | | GAACATTTCTCCTATTGTTGTTGACCTTTGCAAGAAGCAC |
| | | | | AATTTGCCTTACAGGAGCTTATCATTCTGGGACGCCAATG |
| | | | | TTTCCACCCTTAAAACTCTCAGGACTGCTGCCCCTTCAAGC |

TABLE 1-continued

Nucleotide sequences, exon number and source of soluble and membrane bound desaturases from *C. sativa*;

| gene name | class | genomic sequences | exon number | nucleotide (ORF) derived from genome sequence |
|---|---|---|---|---|
| | | | | ACGAGATCTCACCAACCCTATCCCCAAGAACTTGGTCTGG<br>GAAGCTGTTAATACTCATGGCTGA |
| CSD6<br>(SEQ ID<br>No 50) | delta6/8 | FN1_2469249 | 1 | ATGGCGGATTCAACAAAATACATTACCCAAGAAGAGCTTA<br>AACAACACAACAAACATGGAGATCTATGGATCTCAATCCA<br>AGGCAAAATCTACAACGTCTCAGATTGGGCCAAAGACCAT<br>CCCGGCGGCGAACACCCATTACTAAATCTCGCCGGTCAAG<br>ACGTAACAGAAGCTTTCATAGCTTACCATCCAAGGTCGGC<br>ATGGCAATACATGGACCAATTCTTTACTGGGTTTCATCTC<br>AAAGATCACTCCTTTACCGAGGTTTCAAAGGATTACAGAA<br>AACTCGTCAATGAATTTACCAAAATGGGTTTGTTTGAGAA<br>GAAAGGACATGGGGTTTGCTTCTCATTCTTCTTCATTACA<br>TTGTTTTTTATACTCAGTGTTTATGGTGTTATGTGTTCTG<br>ATAGTATTTTGGTTCATTTCTGTTCTGGATGTTTATTAGG<br>GTTTTTATGGATTCAAAGTGGTTGGTTAGGTCATGATTCA<br>GGTCATTATCAAATCATGACTAATCAATTTTATAACAGAT<br>TTGTTCAGATCTTAACTGGGAATTGTTTAGCTGGGATTAG<br>TATTGCTTGGTGGAAATGGAATCACAATGCTCATCATTTA<br>GCTTGTAATAGTCTTGAATTTGATCCTGATCTTAACACA<br>TGCCATTCTTTGTTGTATCATCAAAATTCTTTGATTCACT<br>CACGTCACATTTCTATGGCAGAAAATTGAGTTTTGATTCA<br>ATCACAAGATCCTTAGTTAGTTACCAACATTGGACATTTT<br>ACCCTGTCATGTGTTTAGCTAGGCTTAATCTCTTCGCTCA<br>ATCATTTGCTTTGTTATTATCTAAGAGAAAAGTTCATAAT<br>AGAGGTCAAGAGATTCTTGGGTTACTTGTGTTTTGGATTT<br>GGTATCCACTTTTGGTTTCATATTTACCAAATTGGAGTGA<br>AAGGGTTATGTTTGTCATGGCAAGTTTTTCAGTAACTGGT<br>ATCCAACATGTTCAATTTTGTTTGAACCATTTCTCAGCTA<br>ATGTTTATGTTGGTTTGCCAAGTAGTTATGATTGGTTTGA<br>GAAGCAAACAAAAGGGACACTTAATATCCTTTGTCCTTCT<br>TGGATGGATTGGTTTCATGGCGGTTTGCAGTTTCAGATTG<br>AACACCATTTGTTTCCAAGATTGCCCAAATCACAACTGAG<br>GAAAATTTCTCCCTTTGTTTATGAACTGTGTAAGAAGCAT<br>AATTTGCCTTATAATTGTGCTTCGTTTTGGGAAGCTAATG<br>TAATGACAGTGAATACTCTTAAGACCGCGGCTTTGCAGGC<br>TCGCGATCTTACTAATCCTGTTCCGAAGAACTTGGTTTGG<br>GAAGCTGTCAATACTCATGGATAG |

TABLE 2

Fatty acid content in seed oil of hemp csfad2a and csfad3a mutants;
Table 2. Fatty acid content in seed oil of hemp csfad2a and csfad3a mutants.

| | molar percent of total hempseed fatty acids | | | | | | | | |
|---|---|---|---|---|---|---|---|---|---|
| Mutant name | 16:0 | 18:0 | 18:1$^{\Delta 9}$ Oleic | 18:2$^{\Delta 9,12}$ LA | 18:3$^{\Delta 6,9,12}$ GLA | 18:3$^{\Delta 9,12,15}$ ALA | 18:4$^{\Delta 6,9,12,15}$ SDA | 18:2$^{\Delta 6,9}$ | 18:2$^{\Delta 9,15}$ |
| csfad2a-1 (BC$_2$F$_1$) | 4.34 ± 0.24 | 1.84 ± 0.31 | 77.35 ± 1.25 | 1.96 ± 0.51 | 0.56 ± 0.11 | 3.39 ± 0.39 | 1.13 ± 0.12 | 5.33 ± 0.30 | 2.17 ± 0.24 |
| csfad2a-1 (BC$_2$F$_1$), hetero | 5.87 ± 1.50 | 2.12 ± 0.44 | 15.04 ± 3.05 | 48.46 ± 3.02 | 5.46 ± 0.96 | 18.79 ± 2.72 | 2.26 ± 0.64 | 0 | 0 |
| segregating WT | 5.74 ± 0.54 | 2.38 ± 0.47 | 8.43 ± 1.31 | 55.94 ± 2.93 | 4.33 ± 0.66 | 19.76 ± 2.70 | 1.60 ± 0.30 | 0 | 0 |
| csfad2a-2 (BC$_1$F$_1$) | 4.24 ± 0.48 | 2.52 ± 0.48 | 69.48 ± 2.85 | 5.11 ± 1.08 | 1.10 ± 0.29 | 10.05 ± 0.88 | 1.67 ± 0.12 | 2.99 ± 0.68 | 0.76 ± 0.23 |
| csfad2a-2 (BC$_1$F$_1$), hetero | 5.77 ± 0.43 | 2.89 ± 0.38 | 12.74 ± 0.93 | 46.02 ± 2.06 | 4.01 ± 0.39 | 25.12 ± 1.34 | 1.96 ± 0.19 | 0 | 0 |
| segregating WT | 5.91 ± 0.34 | 2.95 ± 0.44 | 7.29 ± 0.55 | 49.49 ± 1.70 | 4.36 ± 0.23 | 26.45 ± 1.88 | 2.11 ± 0.28 | 0 | 0 |
| csfad3a-1 (BC$_2$F$_1$) | 6.37 | 1.50 | 7.73 | 75.20 | 7.20 | 0.69 | 0.00 | 0 | 0 |
| csfad3a-1 (BC$_2$F$_1$), hetero | 4.99 ± 1.03 | 1.69 ± 0.19 | 8.60 ± 1.32 | 69.32 ± 1.85 | 3.75 ± 0.40 | 9.94 ± 2.21 | 0.54 ± 0.11 | 0 | 0 |

TABLE 2-continued

Fatty acid content in seed oil of hemp csfad2a and csfad3a mutants;
Table 2. Fatty acid content in seed oil of hemp csfad2a and csfad3a mutants.

| | molar percent of total hempseed fatty acids | | | | | | | | |
|---|---|---|---|---|---|---|---|---|---|
| Mutant name | 16:0 | 18:0 | 18:1$^{\Delta 9}$ Oleic | 18:2$^{\Delta 9,12}$ LA | 18:3$^{\Delta 6,9,12}$ GLA | 18:3$^{\Delta 9,12,15}$ ALA | 18:4$^{\Delta 6,9,12,15}$ SDA | 18:2$^{\Delta 6,9}$ | 18:2$^{\Delta 9,15}$ |
| segregating WT | 4.95 | 1.63 | 6.94 | 55.35 | 3.73 | 24.74 | 1.63 | 0 | 0 |
| csfad3a-1 (BC$_3$F$_1$) | 6.04 ± 0.70 | 2.44 ± 0.49 | 7.69 ± 1.23 | 74.71 ± 2.85 | 6.99 ± 2.21 | 0.66 ± 0.13 | 0.08 ± 0.04 | 0 | 0 |
| csfad3a-1 (BC$_3$F$_1$), hetero | 5.18 ± 0.51 | 2.72 ± 0.58 | 8.77 ± 1.20 | 63.67 ± 1.38 | 5.64 ± 1.60 | 11.79 ± 0.86 | 0.99 ± 0.27 | 0 | 0 |
| segregating WT | 4.93 ± 0.53 | 2.50 ± 0.58 | 8.45 ± 1.69 | 53.70 ± 3.04 | 4.98 ± 1.49 | 22.23 ± 2.33 | 1.92 ± 0.63 | 0 | 0 |
| csfad3a-2 (BC$_2$F$_1$) | 4.17 ± 0.25 | 2.12 ± 0.33 | 9.32 ± 1.24 | 77.11 ± 1.26 | 4.35 ± 0.62 | 1.10 ± 0.21 | 0.07 ± 0.04 | 0 | 0 |
| csfad3a-2 (BC$_2$F$_1$), hetero | 4.56 ± 0.43 | 2.37 ± 0.37 | 10.11 ± 1.27 | 65.06 ± 4.18 | 4.00 ± 0.68 | 11.39 ± 4.32 | 0.80 ± 0.34 | 0 | 0 |
| segregating WT | 5.23 ± 0.57 | 2.50 ± 0.87 | 9.36 ± 0.07 | 59.63 ± 5.19 | 3.78 ± 0.48 | 16.76 ± 4.33 | 1.24 ± 0.53 | 0 | 0 |
| csfad2a-3 (BC4F1) | 6.88 ± 0.92 | 2.10 ± 0.46 | 8.14 ± 1.87 | 51.42 ± 2.25 | 8.95 ± 1.04 | 16.95 ± 2.71 | 2.58 ± 0.54 | 0 | 0 |
| segregating WT | 6.78 ± 0.85 | 2.38 ± 0.43 | 8.28 ± 1.67 | 54.65 ± 2.07 | 5.39 ± 0.78 | 17.90 ± 2.98 | 1.66 ± 0.26 | 0 | 0 |
| csfad2a-3 x csfad3a-1 (BC4F3), homo | 6.67 ± 1.76 | 2.85 ± 1.38 | 8.74 ± 0.16 | 66.88 ± 3.66 | 11.33 ± 0.38 | 0.48 ± 0.09 | 0.10 ± 0.01 | 0.24 ± 0.02 | |
| segregating csfad2a-3 (BC4F3), homo | 7.51 ± 0.62 | 1.64 ± 0.47 | 6.25 ± 1.08 | 48.23 ± 2.22 | 8.38 ± 0.55 | 21.65 ± 2.49 | 3.14 ± 0.44 | 0.14 ± 0.03 | |
| segregating csfad3a-1 (BC4F3), homo | 6.48 ± 0.95 | 1.84 ± 0.56 | 7.93 ± 2.52 | 74.39 ± 3.41 | 5.79 ± 2.53 | 0.63 ± 0.15 | 0.06 ± 0.04 | 0.13 ± 0.05 | |
| BC4F3 WT | 7.20 ± 0.61 | 1.37 ± 0.17 | 6.63 ± 1.24 | 52.24 ± 5.65 | 3.25 ± 1.87 | 24.75 ± 4.49 | 1.39 ± 0.88 | 0.09 ± 0.03 | |

TABLE 3

Fatty acid content in leaves of hemp csfad2a and csfad3a desaturase mutants;
Table 3. Fatty acid content in leaves of hemp csfad2a and csfad3a desaturase mutants.

| | molar percent of total leaf fatty acids | | | | | | | | |
|---|---|---|---|---|---|---|---|---|---|
| Mutant name | 16:0 | 18:0 | 18:1$^{\Delta 9}$ Oleic | 18:2$^{\Delta 9,12}$ LA | 18:3$^{\Delta 6,9,12}$ GLA | 18:3$^{\Delta 9,12,15}$ ALA | 18:4$^{\Delta 6,9,12,15}$ SDA | 18:2$^{\Delta 6,9}$ | 18:2$^{\Delta 9,15}$ |
| csfad2a-1 (BC$_2$F$_1$) | 13.29 ± 1.06 | 1.55 ± 0.23 | 1.21 ± 0.31 | 8.32 ± 1.27 | 0.36 ± 0.03 | 67.15 ± 2.00 | 0.53 ± 0.09 | 0 | 0 |
| csfad2a-2 (BC$_1$F$_1$) | 13.74 ± 0.15 | 1.77 ± 0.10 | 1.97 ± 0.33 | 9.95 ± 1.62 | 0.34 ± 0.02 | 67.10 ± 1.95 | 1.95 ± 0.27 | 0 | 0 |
| csfad3a-1 (BC$_3$F$_1$) | 14.24 ± 1.64 | 1.54 ± 0.02 | 2.49 ± 0.06 | 17.93 ± 2.31 | 1.39 ± 0.24 | 60.02 ± 3.75 | 0.80 ± 0.21 | 0 | 0 |
| csfad3a-2 (BC$_2$F$_1$) | 12.28 ± 0.52 | 1.64 ± 0.22 | 3.10 ± 0.46 | 16.05 ± 1.98 | 0.28 ± 0.04 | 58.96 ± 2.41 | 0.71 ± 0.10 | 0 | 0 |
| wild type (Finola) | 13.76 ± 2.02 | 1.56 ± 0.20 | 2.21 ± 0.62 | 9.26 ± 1.36 | 0.33 ± 0.05 | 66.29 ± 2.86 | 1.27 ± 0.57 | 0 | 0 |

Table 4. Fatty acid composition of the yeast transformants led with fatty acid substrates.

TABLE 4

Fatty acid composition of the yeast transformants fed with fatty acid substrates. As controls, yeast cells transformed with empty pESC-TRP vector were subjected to similar conditions. Percent conversion was calculated as product/(substrate + product) * 100 at the assay endpoint. Each value is the mean ± SD from three independent experiments.

| substrate | substrate endpoint mol % total fatty acids | product | product endpoint mol % total fatty acids | % conversion |
|---|---|---|---|---|
| | | Pesc | | |
| $16:1^{\Delta 9}$* | 38.3 ± 0.6 | — | — | — |
| $18:1^{\Delta 9}$* | 45.4 ± 0.6 | — | — | — |
| $18:2^{\Delta 9, 12}$ | 10.9 ± 0.3 | — | — | — |
| $18:3^{\Delta 6, 9, 12}$ | 14.1 ± 0.5 | — | — | — |
| $20:1^{\Delta 11}$ | 0.8 ± 0.05 | — | — | — |
| | | pCSFAD2A | | |
| $16:1^{\Delta 9}$* | 19.3 ± 0.7 | $16:2^{\Delta 9, 12}$ | 14.8 ± 0.6 | 43 ± 1.4 |
| $18:1^{\Delta 9}$* | 12.3 ± 0.5 | $18:2^{\Delta 9, 12}$ | 31.7 ± 0.4 | 72 ± 0.8 |
| $20:1^{\Delta 11}$ | 0.3 ± 0.01 | $20:1^{\Delta 11, 14}$ | 0.5 ± 0.01 | 62 ± 0.3 |
| | | pCSFAD3A | | |
| $16:1^{\Delta 9}$* | 38.2 ± 0.3 | $16:2^{\Delta 9, 15}$ | 1.6 ± 0.04 | 3.9 ± 0.1 |
| $18:1^{\Delta 9}$* | 38.0 ± 0.8 | $18:2^{\Delta 9, 15}$ | 3.6 ± 0.1 | 8.7 ± 0.4 |
| $18:2^{\Delta 9, 12}$ | 4.2 ± 0.2 | $18:3^{\Delta 9, 12, 15}$ | 5.4 ± 0.2 | 56.3 ± 0.5 |
| $18:3^{\Delta 6, 9, 12}$ | 10.7 ± 0.8 | $18:4^{\Delta 6, 9, 12, 15}$ | 3.2 ± 0.2 | 23.1 ± 0.4 |
| $20:1^{\Delta 11}$ | 0.59 ± 0.6 | — | — | — |

*Endogenous substrate; no fatty acid added to medium

Material and Methods cDNA Library Construction and EST Preparation from Developing Seeds of *Cannabis sativa*

Total fatty acid analysis revealed that during seed development the maximum fold increase in fatty acid content occurs at the Upturned (U) stage depicted in FIG. 1A. Upturned stage tissue was ground to a fine powder in liquid nitrogen and RNA extracted using the RNAeasy kit (Qiagen, Hilden, Germany). Starting with 1.2 µg total RNA, first and second strand cDNA synthesis was carried out with the Creator™ SMART™ cDNA Library Construction Kit (Clontech, Mountain View, Calif.) according to the manufacturer's protocol. Twenty cycles of amplification were used for Long Distance-PCR during second strand synthesis. The resulting cDNA samples were treated with Proteinase K, digested with SfiI and size-fractionated on Chroma-spin 400 columns (Clontech) according to the manufacturer's protocol. Pooled cDNA-containing fractions were ligated into pDNR-LIB vector (Clontech) and transformed into *E. coli* TOP10 cells (Invitrogen, Groningen, Netherlands) by electroporation. Transformants were recovered into 96-well plates and insert sizes determined by colony PCR using M13 primers.

From the cDNA library, a total of 1852 ESTs were generated through single-pass Sanger sequencing, yielding 1082 unigene sequences. Blast similarity search identified two unigene sequences with homology to FAD2 desaturases. These sequences were used to prepare primers for Random amplification of cDNA ends (RACE). RACE primers for CSFAD2A: 5'-AAAATGGGAGCCGGTGGCCGAAT-3' (SEQ ID No 5) and 5'-GGGCGGAATTGCTTTCTT-GATTTCGC-3 (SEQ ID No 6)'; RACE primers for CSFAD2B: 5'-GCAGACGATATGACCGTTTCGCT-TCTCA-3' (SEQ ID No 7) and 5'-GCGAGTTGGTA-CAACACGAATGTGGTGA-3' (SEQ ID No 8).

In order to obtain FAD3 homologues that are expressed in developing hemp seeds, degenerate primers from a published source (Lee et al., 1998) were used to amplify a short section of the gene from hemp cDNA (sequences of degenerate primers for FAD3 homologues: 5'-ACNCAYCAY-CARAAYCAYGG-3' (SEQ ID No 9) and 5'-CAYT-GYTTNCCNCKRTACCA-3'(SEQ ID No 10) and sequences for *Arabidopsis* FAD3: 5'-GGCGATTC-CTAAGCACTGTTG-3' (SEQ ID No 11) and 5'-TCACCA-GTGTCGCTGACGTAA-3' (SEQ ID No 12)). The RACE technique was again carried out to obtain full length CSFAD3 cDNA sequence. RACE primers for FAD3: 5'-CACGGCCATGTTGAGAATGACGAG-3' (SEQ ID No 13) and 5'-GGACAAACAGACAAGCAAAGCAGCCA-3' (SEQ ID No 14).

Deep Sequencing the Developing Hemp Seed Transcriptome

Embryos were dissected from developing seed at the Torpedo, Upturned and Filled Not Dessicated stages. Following grinding of the respective tissues in liquid nitrogen, 50 mg of finely ground material was homogenized in 1 mL Tri-reagent (Ambion®, Life Technologies, Carlsbad, Calif.) and RNA extracted according to the manufacturer's protocol. RNA samples were treated with TURBO™ DNase (Ambion®) prior to cDNA synthesis. cDNA was prepared with the SMART cDNA Library Construction Kit (Clontech) according to the manufacturer's instructions but using SuperScript II Reverse Transcriptase (Invitrogen) for first strand synthesis. The CDSIII/3'PCR primer was modified to: 5'-ATTCTAGATCCRACAT-GTTTTTTTTTTTTTTTTTTTTVN-3' (SEQ ID No 15) where R=A or G, V=A, C or G; N=A/T or C/G. A total volume of 500 µL of each second strand reaction was concentrated on AMICON ULTRA 30K columns (Merck Millipore, Billerica, Mass.), digested with MmeI (Fermentas/Thermo Fisher Scientific, Burlington, Canada) and purified with the QIAquick PCR Purification kit (Qiagen, Hilden, Germany).

Pyro-sequencing was carried out on three cDNA libraries prepared from dissected embryos at Torpedo, Upturned and Filled Not Desiccated stages at the GenePool genomics facility at the University of Edinburgh on the 454 GS-FLX sequencing platform (Roche Diagnostics, Branford, Conn., USA). Raw sequence analysis, contiguous sequence assembly and annotation were performed as described previously (Graham et al., 2010). Abundance of membrane bound and soluble desaturase transcripts were analysed in silico by determining read counts in the three EST libraries. The raw reads were mapped to the reference sequence, which consisted of the open reading frames of the 17 desaturase genes (included in Table 1) with BWA mapping software (Li and Durbin, 2009). The raw read counts were retrieved from the resulting output file for each gene in the libraries and the counts were then normalized to an RPKM (reads per kilobase per million reads) value as an approximation of gene expression.

Quantitative Real Time PCR

Total RNA from leaves of two week old and four week old hemp plants was extracted with the TRI Reagent Solution (Ambion®). Single-strand cDNA was synthesised from Turbo DNA-free (Ambion®). DNase-treated RNA using SuperScript II (Invitrogen) reverse transcriptase with oligo $(dT)_{16-18}$ primer (Invitrogen). The completed first-strand cDNA was then diluted to the concentration of 50 ng $\mu L^{-1}$. To estimate the accumulation of CSFAD2A, CSFAD2B and CSFAD3 transcripts, quantitative real time PCR was performed using an ABI Prism 7300 detection system (Applied Biosystems, California, USA) and SYBR Green PCR Master mix (Applied Biosystems) to monitor dsDNA synthesis. The following gene specific primers were used: 5'CTCGGACATAGGGATTTTCATTG3' (SEQ ID No 16) and 5'CAACCCAACCTAACCCTTTGG3' (SEQ ID No 17) for CSFAD2A, 5'TCAAATCCCACACTACCATCTTGT3' (SEQ ID No 18) and 5'TTTCTAGGCTCCCTGTAATACTTTCC3' (SEQ ID No 19) for CSFAD3. All amplification plots were analysed with an $R_n$ threshold of 0.2 to obtain CT (threshold cycle) values. The amount of each transcript was normalised to that of hemp actin-2 gene (hACT2) amplified with primers: 5'GGGTCACACTGTGCCAATCTAC3' (SEQ ID No 20) and 5'CCCAGCAAGGTCAAGACGAA3' (SEQ ID No 21) and compared among samples.

PCR efficiency (E) was estimated by LinRegPCR software (Ramakers et al., 2003; Ruijter et al., 2009). Expression ratios of normalised sample A to normalised sample B were then obtained from the equation $(1+E)^{-\Delta\Delta CT}$ where $\Delta\Delta CT$ represents $\Delta CTA$ minus $\Delta CTB$, and E is the PCR reaction efficiency. Normalised transcript levels in young leaves sample (YL) were used as a calibrator for producing all expression ratios. Dissociation curves of the PCR products were analysed using ABI SDS 2.2 software. The experiment was performed in three biological replicates each of which consisted of three technical replicates.

Establishment and Screening of an EMS-Mutagenized Population

Hemp seed (C. sativa L.) of the Finola variety were purchased from the Finola company (http://www.Finola.com), Finland, and grown in controlled glasshouse facilities at the University of York. The seed was treated with 300 mM EMS for 5 hours and then directly sown onto soil-based John Innes Compost No. 2. Mutagenised M1 female plants were out-crossed with male wild type Finola plants to produce a heterozygous M2 screening population. Typically, DNA from four siblings per M2 family was screened by TILLING. Genomic DNA was isolated from leaves of two week-old M2 individuals using the BioSprint 96 DNA Plant isolation kit (Qiagen) according to the manufacturer's protocol. After fluorometric quantification using Hoescht 33258 dye, DNA samples were normalised to 5 ng $\mu L^{-1}$ and pooled four-fold for screening.

A 1140 bp fragment of CSFAD2A was amplified in a two-step PCR amplification. The first step was carried out with unlabeled primers (5'CCCATTGCTTTAAACGCTCTCTA-ATTCGCT3' (left) (SEQ ID No 22) and 5'CACCCCTAACCACATTAAGCCATACCCCAT3' (right) (SEQ ID No 23) on 12.5 ng pooled gDNA in 10 $\mu L$ volumes. Labeling of the amplified gene fragment with infrared dyes occurred during the second PCR step, where a mixture of labeled and unlabeled primers was used for further amplification and simultaneous labeling using appropriately diluted product from the first PCR step as template (left primer labeled with IRDye 700, right primer labeled with IRDye 800 (MWG, Ebersberg, Germany) ratio labeled: unlabeled=3:2; right primer labeled with diluted IRDye 800, ratio labeled:unlabeled=4:1).

A 1500 bp fragment of CSFAD3A was also amplified in a two-step PCR reaction using non-labeled gene-specific primers: 5'cgccattcctaagcattgtt3' (left) and 5'atagtggtcctggctgatgc3' (right) in the first step. As for the Δ12-desaturase fragment, labeling with infrared dyes occurred during the second PCR but using 5'M13-tailed primers: 5'TGTAAAACGACGGCCAGTgggctgctcaaggaaccatgttct3' (SEQ ID No 24) (left) and 5'AGGAAACAGCTATGACCATccttggtagcttccacaagatgg3' (right) (SEQ ID No 25) mixed with M13 primers labeled with IRDye 700 and IRDye 800. The ratios of labeled to unlabeled primers were as above for the CSFAD2A fragment. Heteroduplex formation was carried out as described by Till et al. (2006) followed by digestion with CEL I nuclease as described elsewhere (Till et al., 2006). CEL I digested products were purified by isopropanol precipitation and resuspended in formamide-containing buffer, loaded onto polyacrylamide gels and run on the LI-COR 4300 DNA sequencer platform (Till et al., 2004; Till et al., 2006).

Cloning and Expression of C. sativa CSFAD2A and CSFAD3A in Saccharomyces cerevisiae Full length open reading frame (ORF) of CSFAD2A (1154 bp) was amplified by PCR using Phusion Hot Start DNA polymerase (Finnzymes, Espoo, Finland) from Finola wild type genomic DNA with the following primers: 5'ATA GGATCCaaaatgggagccggt3' (SEQ ID No 26) and 5'GC CTCGAGCctaaaacttgttttttgtacc3' (SEQ ID No 27). The amplified product of CSFAD2A was ligated into pESC-TRP yeast expression vector (Stratagene, La Jolla, Calif., USA) between BamHI and XhoI restriction sites (underlined in primer sequences) under the galactose-inducible GAL1 promoter and transformed to chemocompetent E. coli DH5α.

The coding sequence of CSFAD3A (1191 bp long) was amplified in PCR using Phusion Hot Start DNA polymerase (Finnzymes) from the Upturned stage of hemp seed embryo cDNA of Finola wild type with the following primers: 5'GGGGAATTCataatgacagaatcacatgc3' (SEQ ID No 28) and 5'TAGCGGCCGCATACTACATTTGCTTGGC3' (SEQ ID No 29). CSFAD3A PCR product was ligated into pESC-TRP vector between EcoRI and NotI restriction sites (underlined in primer sequences) under the alternative GAL10 galactose-inducible promoter and transformed to chemocompetent E. coli DH5a cells.

Plasmid constructs were extracted from the small scale bacterial liquid cultures with a NucleoSpin Plasmid mini kit (Macherey-Nagel, Duren, Germany) and the orientation and identity of inserts were confirmed by Sanger DNA sequencing. The S. cerevisiae strain G175 (ScanBi, Alnarp, Sweden) were transformed with pCSFAD2A and pCSFAD3A plasmid constructs by the lithium acetate method (Gietz and Woods 2002) and selected on Synthetic Dextrose Minimal Medium lacking tryptophan.

For the functional expression of CSFAD2A and CSFAD3A, corresponding yeast transformants were cultivated at 28° C. with shaking at 150 rpm in 50 mL volume of synthetic minimal medium containing 2% (w/v) raffinose and 1% Tergitol NP-40 (Sigma, St. Louis, USA). Expression of the transgene was induced by addition of 2% (w/v) galactose to cultures upon reaching $OD_{600}$=0.2-0.3 and further incubation was carried out at 25° C. with shaking at 150 rpm for 28 hours. For the studies on CSFAD2A and CSFAD3A desaturase specificities the cultures at the time point of induction were supplemented with exogenous fatty acids (LA, GLA, or $20:1^{\Delta 11}$ eicosenoic acid) up to 50 µM final concentration. Each experiment was performed with at least three replicates, with a pESC-TRP empty vector yeast transformants control cultivated simultaneously. For the FAMEs analyses, the yeast cells were harvested by centrifugation at 4500 g for 5 min at 4° C. and washed three times with deionized water. Obtained yeast pellets were either stored at −80° C. for a short period of time or were directly analyzed for their fatty acids profiles. The corresponding open reading frames (ORF) of the hemp Δ12 desaturase CSFAD2A and Δ15 desaturase CSFAD3 were amplified by PCR using Phusion Hot Start DNA polymerase (Finnzymes) and the following pairs of specific primers: 5'ATA GGATCCaaaatgggagccggt3' (left) (SEQ ID No 30) and 5'GCCTCGAGCctaaaacttgttttgtacc3' (right) (SEQ ID No 31) for CSFAD2A and 5'GGG GAATTCataatgacagaatcacatgc3' (left) (SEQ ID No 32) and 5'TAGCGGCCGCATACTACATTTGCTTGGC3' (right) (SEQ ID No 33) for CSFAD3. For ligation behind the constitutive GAL1 gene promoter of the yeast expression vector pESC-TRP (Stratagene), the primers for CSFAD2A were extended by a BamHI and XhoI restriction site (underlined) and for ligation behind the alternative constitutive GAL10 gene promoter the primers for CSFAD3 were extended by an EcoRI and NotI restriction site (underlined). The resulting PCR products and the pESC-TRP vector were digested with the corresponding restriction enzymes and ligated. The nucleotide sequence of corresponding inserts was confirmed by sequencing. The S. cerevisiae strain G175 was transformed with these plasmids by the lithium acetate method (Gietz and Woods 2002) and selected on minimal agar plates lacking tryptophan.

For functional expression, cultures were grown at 28° C. in the presence of 2% (w/v) raffinose and 1% (w/v) Tergitol NP-40 (Sigma). Expression of the transgene was induced when $OD_{600}$ reached 0.2-0.3 by supplementing galactose to 2% (w/v). At that time the appropriate fatty acids were added to a final concentration of 50 µM. Incubation was carried out at 25° C. for four generations (28 hours). For each experiment, an empty pESC-TRP vector-transformed control was cultivated simultaneously. Each experiment was performed with three replicates. Yeast cells were harvested by centrifugation at 4500 g for 5 min at 4° C., and washed three times with deionized water.

Fatty Acid Analysis

Fatty Acid Methyl Esters (FAMEs) were prepared by direct transmethylation of single seeds or ~10 mg oil samples (Browse et al., 1986). FAME content was determined by gas-chromatography with flame ionization detection (GC Trace Ultra, Thermoquest Separation Products, Manchester, UK). A 1 µL aliquot of FAMEs in hexane was injected into a 3 mm internal diameter FocusLiner containing glass wool (SGE, Milton Keynes, UK) at 230° C. in programmed flow mode with $H_2$ as carrier gas. The $H_2$ flow program was as follows: initial hold 0.3 mL min$^{-1}$ for 0.1 min, then ramped at 5 mL min$^{-2}$ to 0.5 mL min$^{-1}$ for the remainder of the run. The split ratio was maintained at 1:250 and a gas saver slow of 20 mL min$^{-1}$ was initiated at 1.5 min into the run. Separation was achieved using a narrow-bore cyanopropyl polysilphenylene-siloxane capillary column (SGE BPX70; 10 m length×0.1 mm internal diameter×0.2 µm film thickness). FAMEs were separated using the following temperature program: initial hold 150° C. 0.1 min, then ramped at 16° C. min$^{-1}$ to 220° C., followed by cool-down to initial conditions at 120° C. min$^{-1}$. The FID was run at 300° C. with air, $H_2$ and make-up N2 gases flowing at 350, 35, and 30 mL min$^{-1}$, respectively. The signal was collected and peaks detected and integrated using ChromQuest 4.2 software (Thermo Electron Corporation, Manchester, UK). FAMEs were identified and quantified relative to the Supelco 37 component FAME mix (Sigma-Aldrich, Gillingham, UK).

Extracts containing FAMEs that did not coelute with standards or whose identity was unclear were concentrated and further derivatized to their 3-pyridylcarbinol esters (Dubois et al. 2006), chromatographed using a longer, thicker-film BPX70 column using He as carrier gas with an extended thermal gradient, and 70 eV electron impact mass spectra generated using a Leco Pegasus IV mass spectrometer running ChromaTof 4.5 software (Leco, Stockport, UK). Under these conditions, retention time order was preserved as per the GC-FID analyses. Mass spectra were interpreted to localise dienoic double bond positions as described by Christie et al. (1987).

Phenotyping for fatty acid content was carried out on single cotyledons dissected from two-days-old seedlings germinated on moist filter paper. The surviving seedlings were planted to soil, grown, genotyped and selected individuals were used for subsequent crosses.

Cold Pressing of Oil Seeds.

Oil pressing was carried out using a small capacity Komet screw press (Model CA 59 G, IBG Monforts, Mönchengladbach, Germany), with a 6 mm press nozzle die and a screw speed of 20 rpm. Running temperature was checked with a digital thermometer inserted into the restriction die, with screw-press barrel temperature not exceeding 60° C. After each sample, all press devices were cleaned and dried.

Assessment of Oxidative Stability of Oils.

The oxidative stability of the pressed oils was determined using a Metrohm Rancimat model 743, according to AOCS Official Method Cd 12b-92. Briefly, the induction times (n=4) for portions of oil (3.0 g) were determined at 100, 110 and 120° C. and 20 L h$^{-1}$ air throughput. Projected shelf life stability was calculated by extrapolation of the relationship between the measured induction time and the temperature (Metrohm Application Bulletin No. 141/3e).

EXAMPLE 1

Genome Mining Reveals Multiple Copies of Soluble and Membrane Bound Desaturases in *C. sativa*

In dicotyledonous oilseeds, storage oil in the form of triacylglycerol (TAG) is synthesized during embryo growth. We isolated mRNA from the Upturned (U) stage of embryo development of the Finola variety since this represents a stage of significant storage oil deposition in dicotyledonous oilseeds (Baud et al., 2002) and used this for cDNA library construction. We initially generated 1893 Expressed Sequence Tags (ESTs) from the upturned U stage cDNA library by conventional Sanger sequencing and a BLASTX similarity search revealed 11 ESTs with homology to desaturase genes. Two of the resulting unigenes contained an incomplete Open Reading Frame (ORF) giving a predicted amino acid sequence with homology to the Δ12-desaturases. Two homologous full-length cDNA sequences were obtained by RACE PCR, and the corresponding genes were named CSFAD2A and CSFAD2B (FIG. 12; Table 1). We also cloned a FADS desaturase fragment by PCR amplification using degenerate primers (Lee et al., 1998) on the upturned U stage cDNA. RACE PCR produced a 1188 bp full-length cDNA sequence that we name CSFAD3A (FIG. 14; Table 1).

We used CSFAD2A, CSFAD2B, CSFAD3A and various other previously characterized plant membrane bound Δ12- (FAD2), Δ15-(FAD3) and Δ6-/Δ8-sphingo-lipid, as well as the soluble Δ9-Stearoyl-ACP-desaturases as queries to retrieve additional membrane bound and soluble desaturase sequences from the genome sequences of two different varieties of *C. sativa*, Purple Kush (canSat3) and Finola (Finolal) (van Bakel et al., 2011). This resulted in the identification of putative sequences for seven FAD2 (designated CSFAD2A to CSFAD2G) three FAD3 (designated CSFAD3A, CSFAD3B and CSFAD3C), two genes with homology to both Δ8-sphingo-lipid desaturases and Δ6-fatty acid desaturases (designated CSD8 and CSD6) and five Δ9-Stearoyl-ACP-desaturases (designated CSACPD-A to CSACPD-E) in the more complete genome of the Purple Kush variety. For all but CSFAD2F and CSFAD3C orthologous sequences were also identified in the Finola genome (Table 1), which probably reflects the draft nature of this genome.

EXAMPLE 2

Deep Sequencing of the Developing Seed Transcriptome Identifies Candidate Desaturases Involved in Modifying Fatty Acid Composition of Seed Oil EST libraries were prepared by deep sequencing cDNA prepared from RNA isolated from Torpedo (T), Upturned (U) and Filled Not Desiccated (FND) stages of Finola embryo development as depicted in FIG. 1A. Raw reads were mapped to the open reading frames of seventeen putative desaturase genes as detailed in Table 1. Three of the five plastidial stearoyl-ACP desaturases are expressed with CSSACPD-C transcripts being the most abundant, three of the seven CSFAD2 genes are expressed with CSFAD2A being the highest, all three of the CSFAD3 genes are expressed but of these only CSFAD3A increases during embryo development with CSFAD3B and CSFAD3C present at very low levels. CSD8 and CSD6 show similar low levels of expression up until the Upturned stage with transcripts of both genes being absent at the later FND stage (FIG. 1A). Based on homology and expression analysis lead candidates for each of the desaturation steps shown in FIG. 1B can be identified as CSACPD-C, CSFAD2A, CSFAD3A and CSD6. We focused our efforts on functionally characterizing CSFAD2A and CSFAD3A.

EXAMPLE 3

Characterisation of the *Cannabis sativa* Microsomal Desaturase CSFAD2A

Figure 2B:
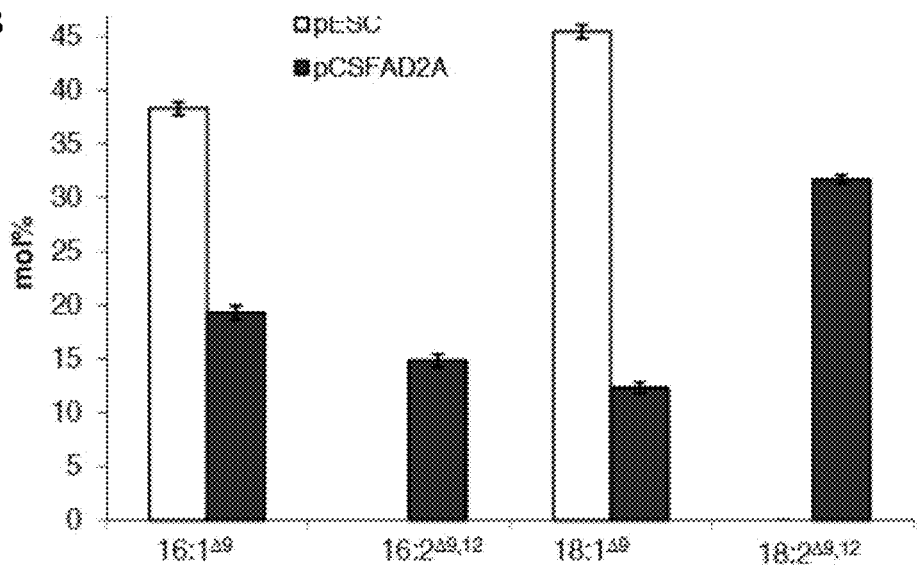
Figure 6A:
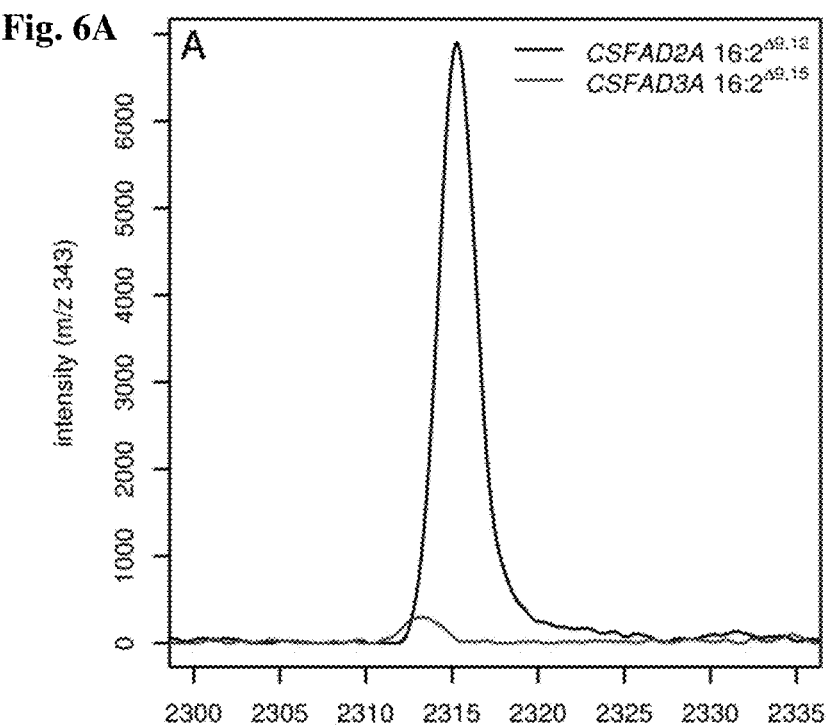
FIGS. 6A-6C: Hexadecadienoic acid double bond localisation; Hexadecadienoic acid double bond localisation. S. cerevisiae pellets from cultures expressing CSFAD2A or CSFAD3A were harvested 28 h after gal induction and transmethylated to FAMEs. An aliquot of the isolated FAME fraction was transesterified to 3-pyridylcarbinol esters, which were then chromatographically separated and detected by GCMS on a polar BPX70 column. Extracted ion chromatograms for the expected molecular ion of m/z 343 consistent with 16:2 indicated two resolved peaks (A). Mass spectra from the first eluting peak (from the CSFAD2A expressing sample) identified this peak as 16: $2\Delta9,12$ (B). Mass spectra from the second eluting peak (from the CSFAD3A expressing sample) identified this peak as 16:$2\Delta9,15$ (C). Insets show the molecular structure of the relevant 3-pyridylcarbinol fatty acid esters with predicted abundant mass spectral fragments containing the pyridyl headgroup; i.e. fragments arising from cumulative methyl-end losses. Mass spectra are labelled with all predicted mass spectral fragments that were actually found in the mass range shown.
Figure 6B:
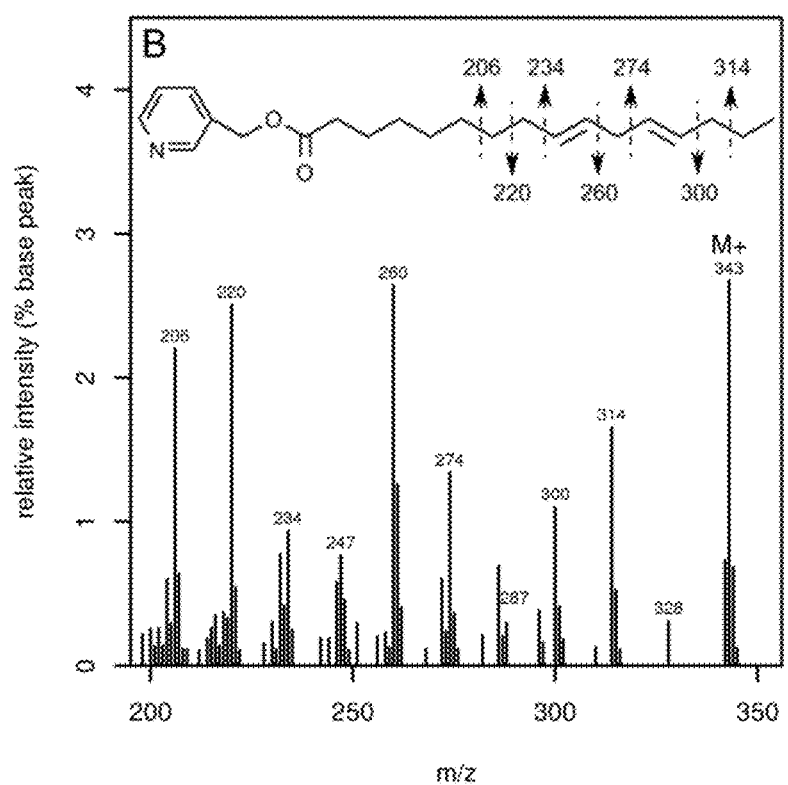
Figure 6C:
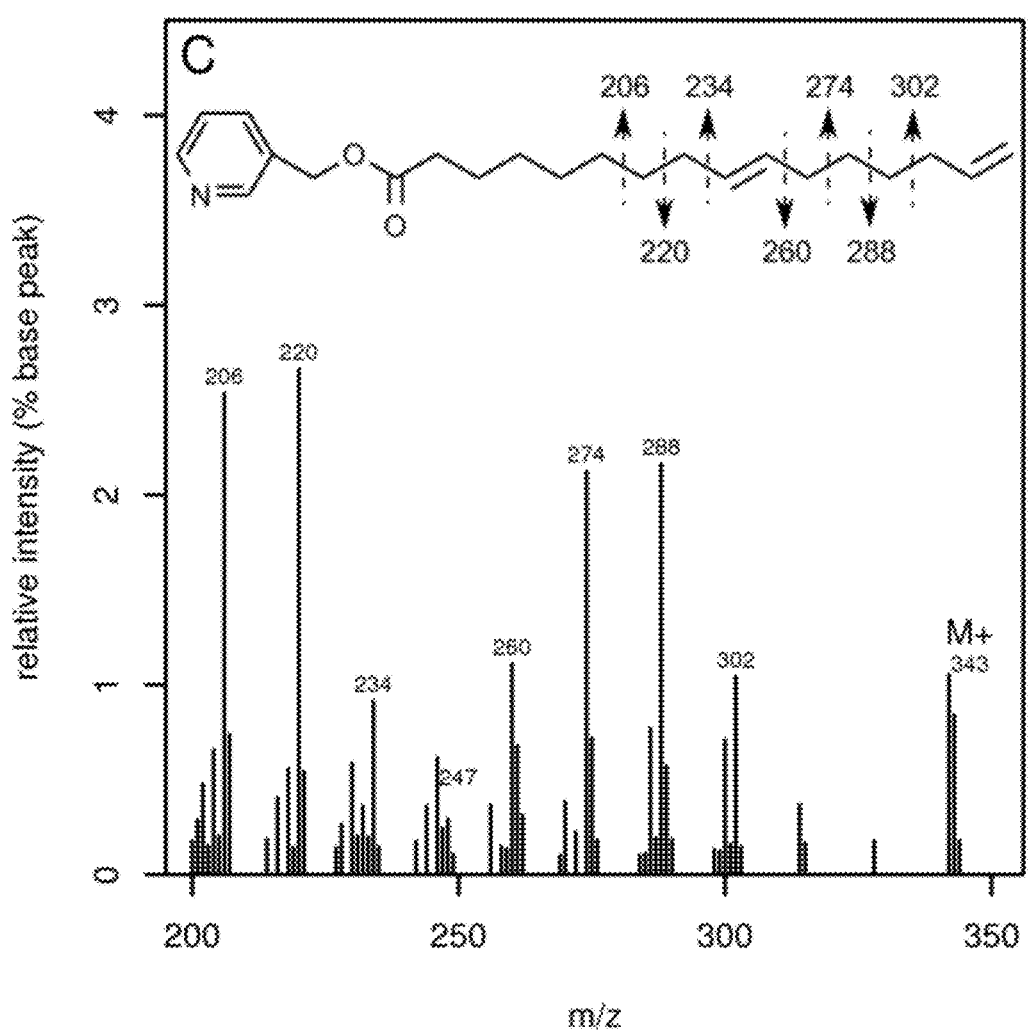
Figure 7A:
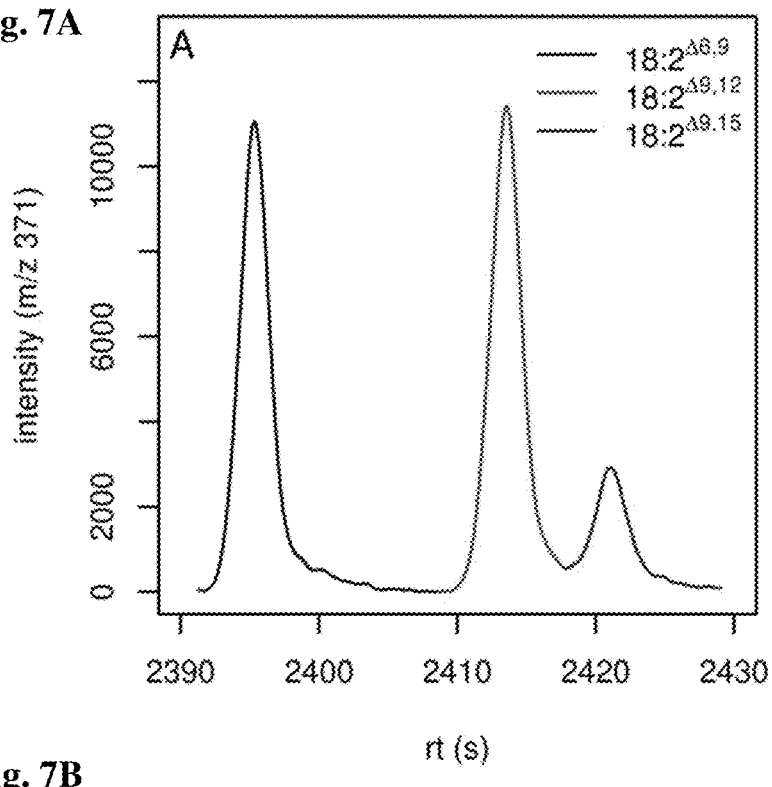
FIGS. 7A-7D. Octadecadienoic acid double bond localisation; Oil samples extracted from field-grown high-oleic acid hemp were analysed and plotted as described in FIG. 6. Extracted ion chromatograms for the expected molecular ion of m/z 371 consistent with 18:2 indicated three resolved peaks (A). Mass spectra from the first eluting peak identified this peak as 18:$2\Delta6,9$ (B), the second as 18:$2\Delta9,12$ (C), and the third as 18:$2\Delta9,15$ (D). This third peak was also found in yeast extracts expressing CSFAD3A.
Figure 7B:
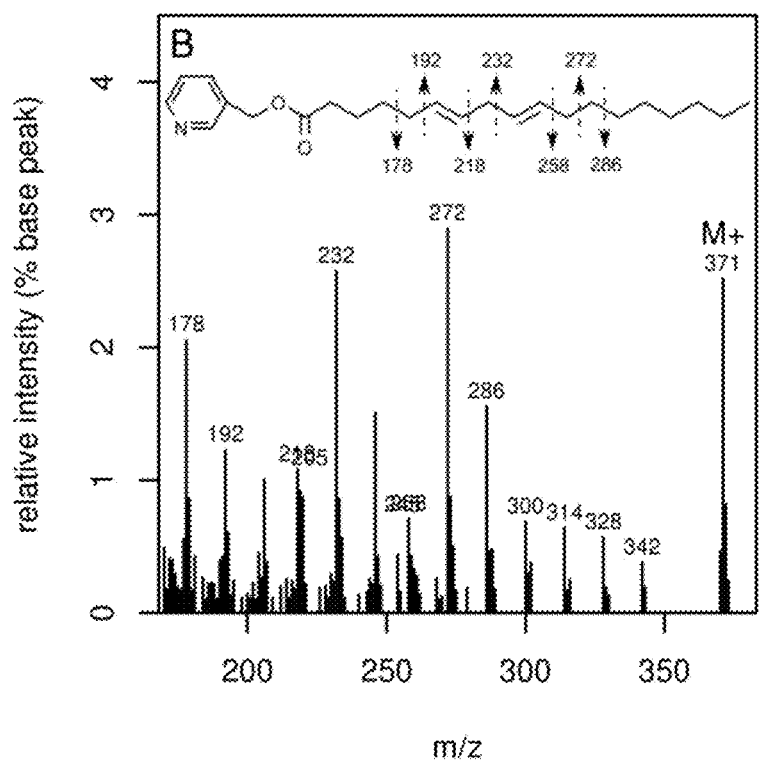
Figure 7C:
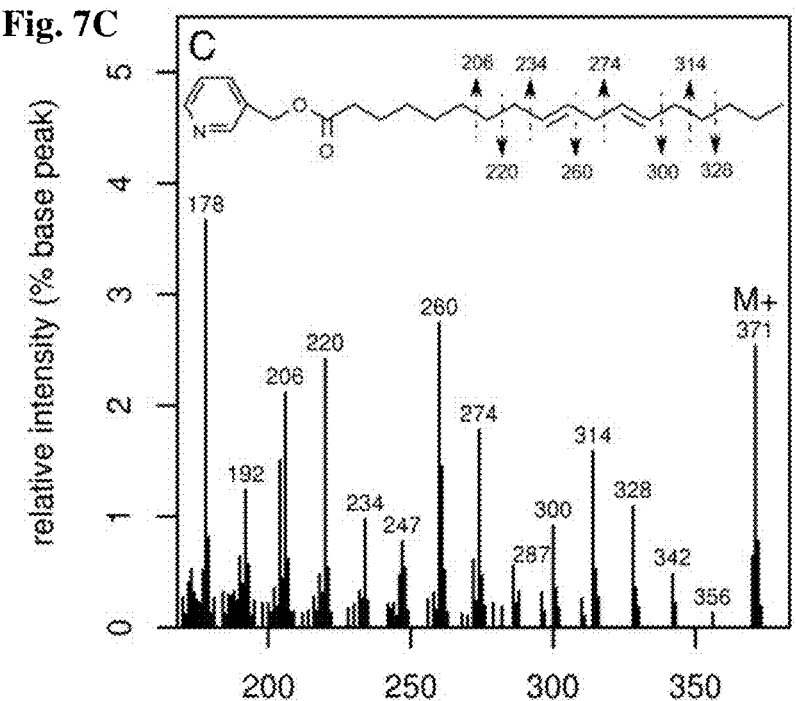
Figure 7D:
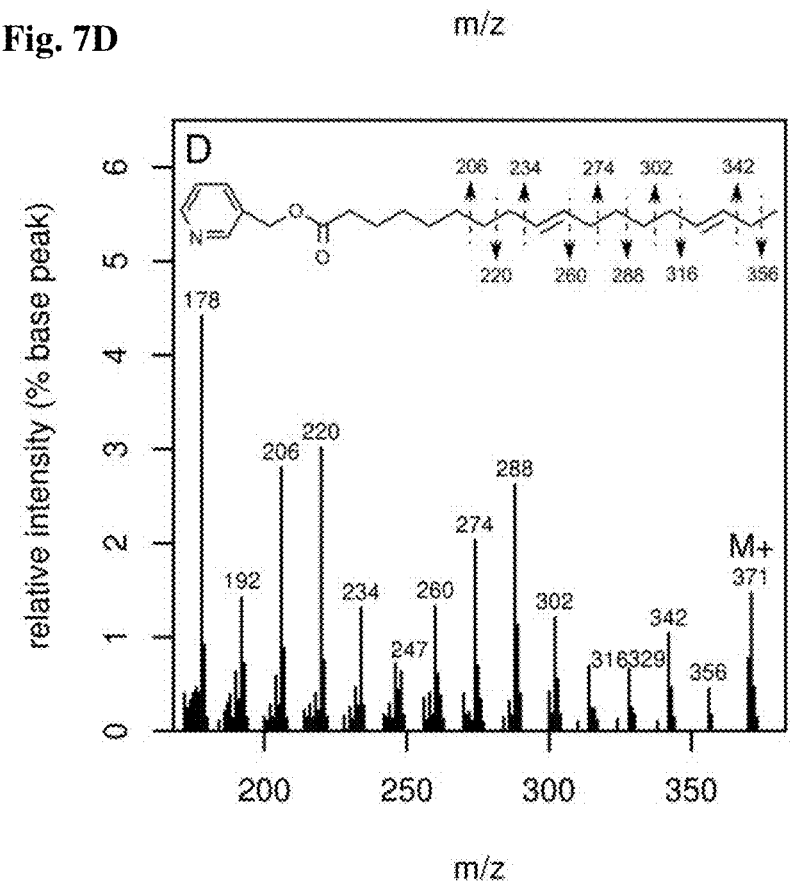
Figure 8A:
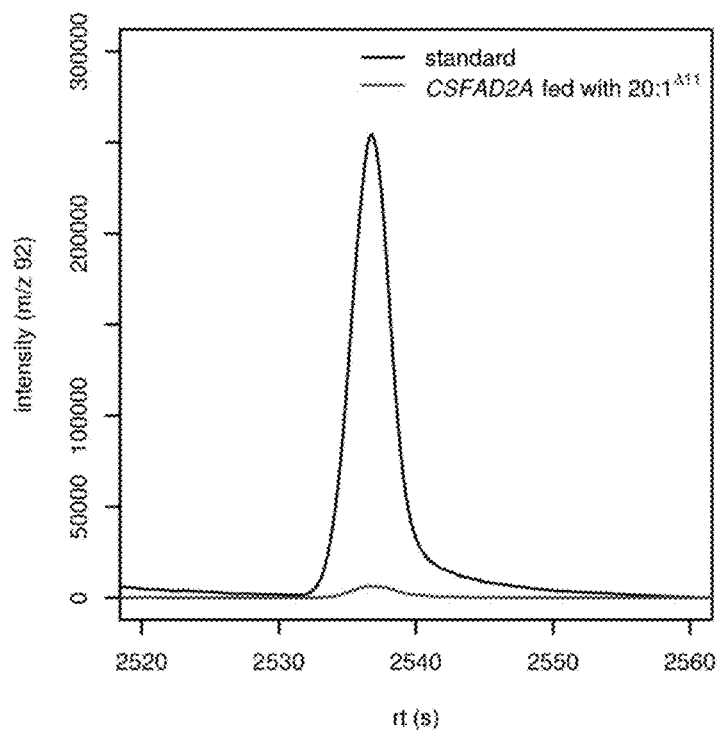
FIGS. 8A-8C. Eicosadienoic acid double bond localisation; The standard 37-FAME mix containing 20:$2\Delta11,14$ as the only 20:2 FAME and FAMEs from yeast expressing CSFAD2A fed with 20:$1\Delta11$ were transesterified to their 3-pyridylcarbinol esters and analysed as described in FIG. 6. Although the expected molecular ion of m/z 399 could be detected in both samples, the signal was weak in the yeast extracts; therefore for clarity the 3-pyridylcarbinol ester common base ion of m/z 92 was used to identify co-elution of candidate 20:2 peaks (A). Mass spectra from the standard (A) and the yeast extract (B) confirmed a single peak with the identity 20:$2\Delta11,14$.
Figure 8B:
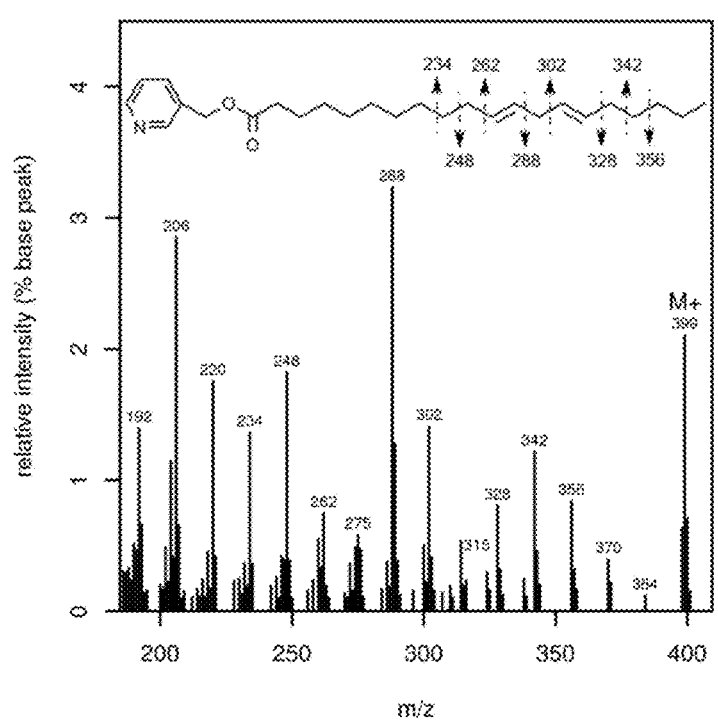
Figure 8C:
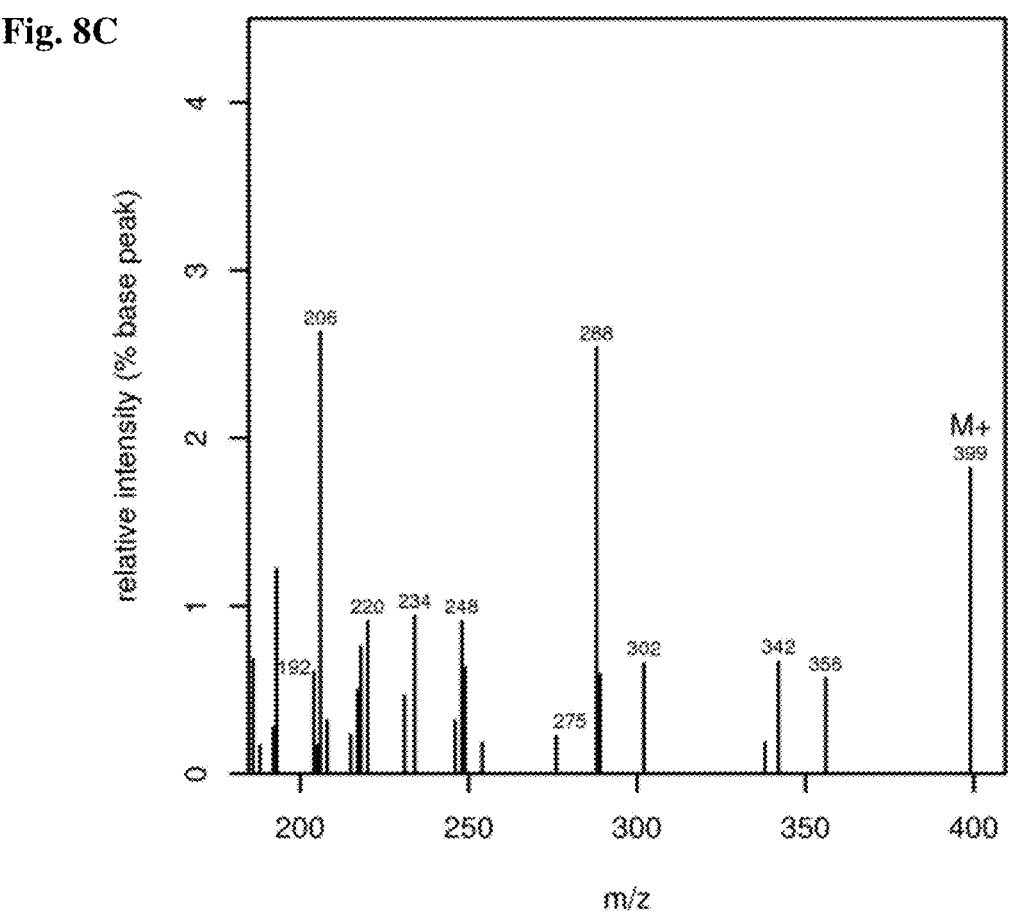

Quantitative RT-PCR analysis confirmed the high level expression of CSFAD2A during embryo development, peaking at the FND stage where it was more than 1000 times higher than in young leaves (FIG. 2A). A similar pattern of expression but at much lower levels was observed for the CSFAD2B gene with the difference in expression between leaves and embryo much less pronounced, being about 20 times higher at the FND stage (FIG. 2A). To confirm the functional identity of CSFAD2A we cloned the corresponding ORF into the expression vector pESC-TRP containing the galactose-inducible GAL1 promoter and heterologously expressed this in the yeast *Saccharomyces cerevisiae*. This yeast has been used successfully for functional expression of several plant microsomal desaturases, since it acts as a convenient host with a simple fatty acid profile due to the presence of only a Δ9-desaturase producing palmitoleate and oleate, and the appropriate redox chain in a suitable membrane (Reed et al., 2000). Fatty acid analysis of the transformed yeast cells revealed the presence of two new fatty acids that were not present in either the wild-type yeast or in the empty vector control (FIG. 2B; Table 4). GC analysis of the fatty acid methyl esters (FAMEs) demonstrated that the major novel peak is linoleic acid. As shown in Table 4, 72% of the endogenous oleic acid ($18:1^{\Delta 9}$) appears to have served as substrate for CSFAD2A and been converted into linoleic acid ($18:2^{\Delta 9,12}$) confirming CSFAD2A to have Δ12-desaturase activity. We trans-esterified the FAME fraction to 3-pyridylcarbinol esters and used GCMS to identify the second novel peak as $16:2^{\Delta 9,12}$ (FIG. 6). We therefore conclude that CSFAD2A can also use palmitoleic acid ($16:1^{\Delta 9}$) as substrate, with a conversion efficiency to $16:2^{\Delta 9,12}$ of 43% (FIG. 2B; Table 4). Feeding eicosenoic acid ($20:1^{\Delta 11}$) to the CSFAD2A-transformed yeast cultures resulted in 62% conversion to $20:2^{\Delta 11,14}$ demonstrating that the enzyme can accept 16-20C fatty acids and that the specificity is most accurately described as Δx+3 (Schwartzbeck et al., 2001).

EXAMPLE 3

Identification and Characterization of Three CSFAD2A Desaturase Mutants

To establish the in-vivo role of CSFAD2A we screened an ethyl methane sulphonate (EMS) mutagenized M2 outcrossed population of Finola using the TILLING method (Till et al., 2006). We identified an allelic series of mutations among which csfad2a-1 carries a stop codon at amino acid position 167. We performed two rounds of backcrossing of csfad2a-1 to Finola and obtained homozygous csfad2a-1 individuals ($BC_2F_1$) by crossing heterozygous male and female $BC_2$ siblings. csfad2a-1 homozygotes displayed a dramatic increase in oleic acid content to 77 molar % in seed oil (FIG. 2C; Table 2). In parallel, the levels of LA and ALA were strongly decreased compared to the fatty acid profile of the segregating wild type seed oil from the same population suggesting that this decrease was at the expense of the increase in oleic acid (FIG. 2C; Table 2). Two novel fatty acids appeared in csfad2a-1 at 5 and 2 molar percent (Table 2). GC retention times indicated these to be 18:2 fatty acids and GCMS following derivatization to 3-pyridylcarbinol esters revealed these to be $18:2^{\Delta 6,9}$ and $18:2^{\Delta 9,15}$ respectively (Table 2). These may arise through the action of other desaturases on the high percentage oleic acid present in the developing embryos of csfad2a-1. Summarising, the dramatic fatty acid level changes observed in csfad2a-1 seed confirmed that the predicted truncated CSFAD2A protein is non-functional. Interestingly, no major changes in seed fatty acid profile were observed if the mutation was present in the heterozygous state indicating that only one copy of this highly expressed CSFAD2A gene is sufficient to maintain the near wild type level of fatty acids in hemp seed.

We also identified a second allele, csfad2a-2, which carries two point mutations giving rise to a proline to serine transition at positions 218 and 375 of the predicted amino acid sequence of CSFAD2A. Homozygous csfad2a-2 ($BC_1F_1$) seed accumulate nearly 70 molar percent of oleic acid, low level accumulation of $18:2^{\Delta 6,9}$ and $18:2^{\Delta 9,15}$ and decreased levels of LA and ALA compared to heterozygous and segregating wild type seeds from the same population (FIG. 2D; Table 2). This seed oil phenotype is very similar to that of csfad2a-1 (FIG. 2C) and is consistent with one or both of the P to L transitions disrupting protein function. This is expected given the importance of proline amino acids in determining protein structure. Interestingly, the levels of oleic acid, linoleic acid and α-linolenic acid remained unchanged in leaf tissues of both csfad2a-1 and csfad2a-2 compared to wild type plants (Table 3) which is consistent with the gene expression data showing CSFAD2A to be largely seed specific (FIG. 2A).

Figure 4A:
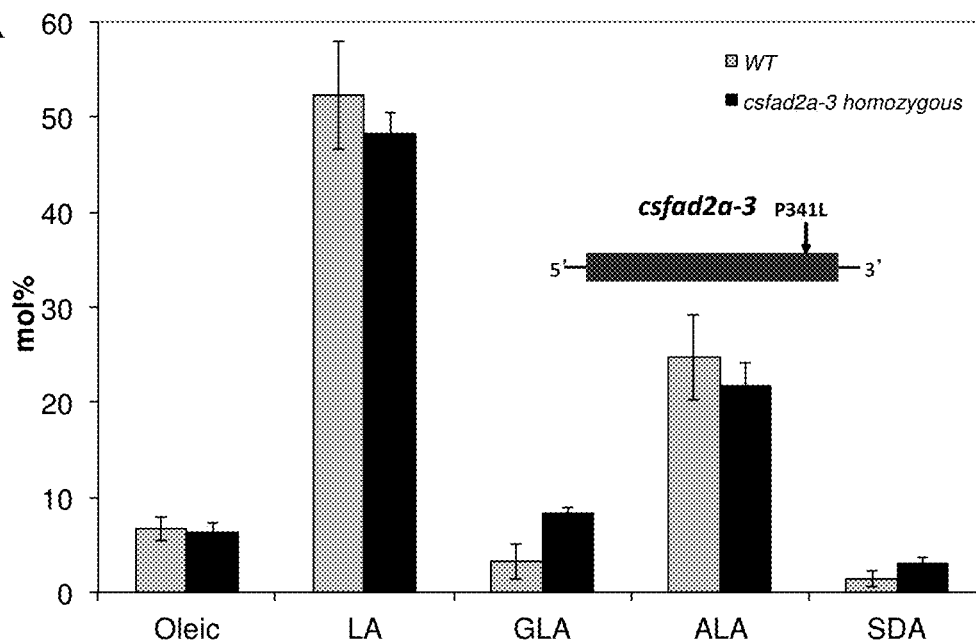
FIGS. 4A-4B. (A) Fatty acid composition of seed oil from homozygous csfad2a-3 ($BC_4F_1$) compared to respective segregating wild type plants from the same generation as detailed in Table 2. Each value is the mean±SD from 20 (WT) and 60 seeds (csfad2a-3) from the same line and generation; (B) Fatty acid composition of seed oil from homozygous csfad2a-3×csfad3a-1 ($BC_4F_2$) double mutant compared to respective segregating homozygous csfad2a-3, csfad3a-1 and wild type plants from the same generation as detailed in Table 2. Each value is the mean±SD from 6 to 40 seeds from the same line and generation.

We also identified a third mutant allele, csfad2a-3, which carries a point mutation giving rise to a proline to serine transition at position 341 of the predicted amino acid sequence of CSFAD2A. We performed four rounds of backcrossing of csfad2a-3 to Finola and obtained a segregating $BC_4F_1$ population by crossing heterozygous male and female $BC_4$ siblings. Sibling crosses were then set up between homozygous csfad2a-1 $BC_4F_1$ plants and homozygous CSFAD2a-1 $BC_4F_1$ wild-type plants, respectively, and fatty acid profiling carried out on resulting seed. Compared to CSFAD2a-1 wild type seed homozygous csfad2a-1 seed displayed an increase in gamma linolenic content of up to 9 molar % in their oil (FIG. 4A; Table 2). Likewise, stearidonic acid levels increased to 2.6 molar %. In parallel, the levels of LA and ALA slightly decreased compared to the fatty acid profile of the segregating wild type seed oil from the same population suggesting that this decrease was at the expense of the increase in gamma linolenic and stearidonic acid (FIG. 4A; Table 2). The increase of gamma linolenic and stearidonic acid in the seed oil of homozygous csfad2a-3 plants is unexpected and points towards increased access of the CSFAD2 product, LA, to Δ6-desaturase activity.

EXAMPLE 4

Characterisation of the *Cannabis sativa* Microsomal Desaturase CSFAD3A

Figure 3A:
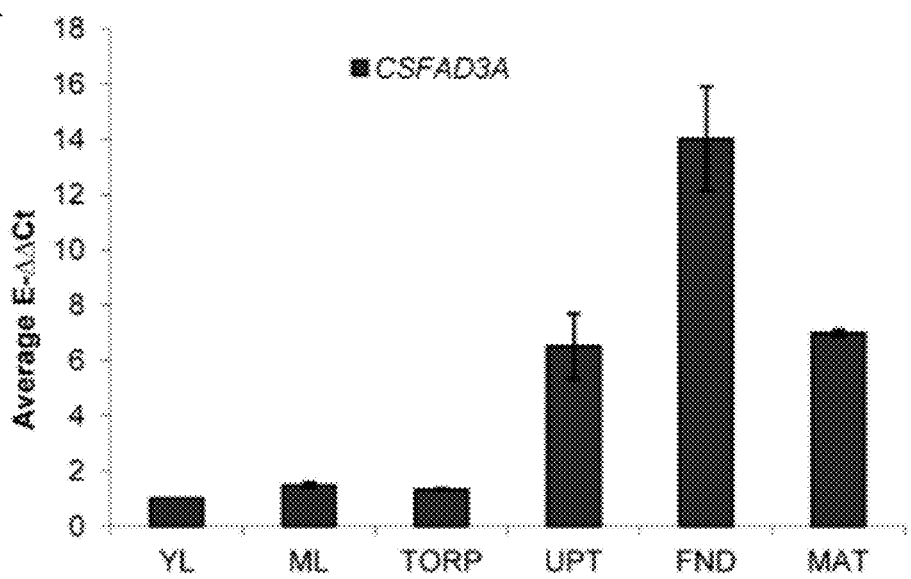
FIGS. 3A-3D Characterisation of CSFAD3A gene function. (A) Expression of CSFAD3A in developing embryo and mature leaf tissue compared to levels in young hemp leaves. Raw quantitative PCR data were normalised to hemp ACT2 transcript level in each tissue and expressed as $(1+E)-\Delta\Delta Ct$ where E is the amplification efficiency. Mean values represent the average of three biological replicates each consisting of three technical replicates. YL, young leaves; ML, mature leaves; TORP, torpedo stage of hemp embryo; UPT, U-upturned stage of hemp embryo; FND, filled-not-desiccated stage of hemp embryo; MAT mature seed embryo. (B) Fatty acid composition of S. cerevisiae transformed with either CSFAD3A cDNA or an empty vector (pESC-TRP) control. Both transformants were subjected to similar induction and feeding with LA and GLA. Each value is the mean±SD from three independent experiments. (C) Fatty acid composition of seed oil from homozygous csfad3a-1 ($BC_3F_1$) and (D) homozygous csfad3a-2 ($BC_2F_1$) plants compared to respective segregating heterozygous and wild type plants from the same generation as detailed in Table 2. Each value is the mean±SD from 4 to 20 seeds from the same line and generation.
Figure 3B:
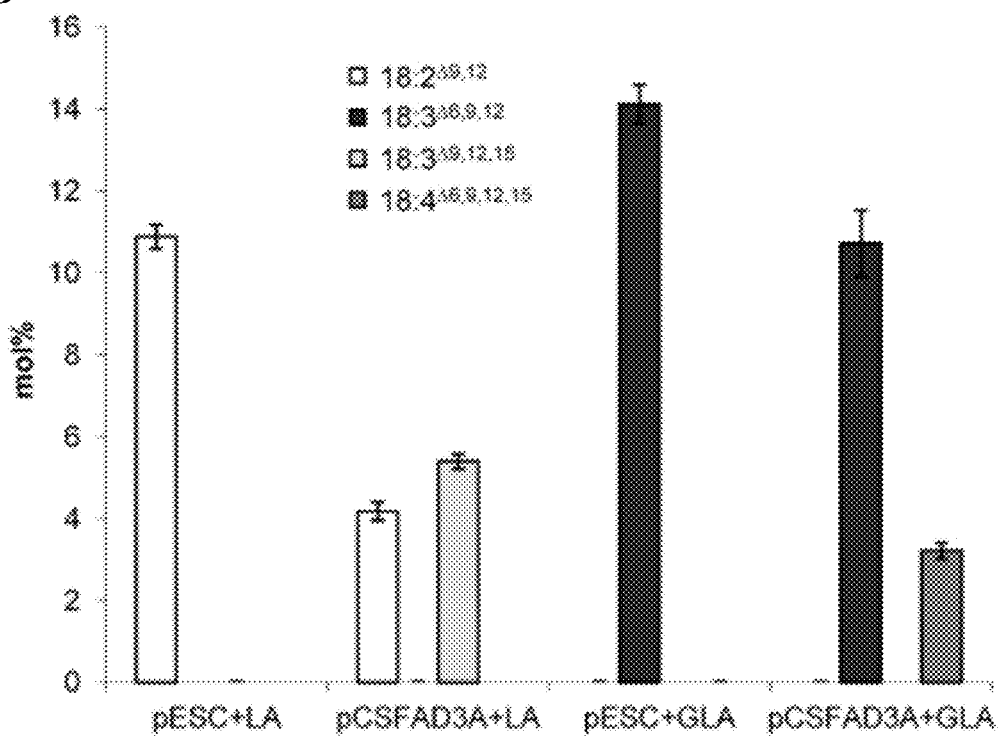

Quantitative RT-PCR confirmed expression of CSFAD3A in both leaves and embryos and showed it to be induced during seed development peaking at the FND stage where it is about 14 times higher than levels in young leaves (FIG. 3A). Heterologous expression of CSFAD3A in *S. cerevisiae* followed by fatty acid feeding resulted in desaturation of linoleic ($18:2^{\Delta 9,12}$) to α-linolenic acid ($18:3^{\Delta 9,12,15}$) and γ-linolenic acid ($18:3^{\Delta 6,9,12}$) to stearidonic acid ($18:4\Delta^{6,9,12,15}$) at a conversion efficiency of 56% and 23%, respectively (FIG. 3B; Table 3). The yeast CSFAD3A transformants also exhibited low level activity with endogenous $16:1^{\Delta 9}$ and $18:1^{\Delta 9}$ resulting in what we identified as $16:2^{\Delta 9,15}$ and $18:2^{\Delta 9,15}$ respectively (Table 3, FIGS. 6A-6C and 7A-7D). CSFAD3A transformants did not show any activity on exogenously supplied $20:1^{\Delta 11}$ after 28 hrs incubation. Together these results confirm that CSFAD3A acts as a Δ15-desaturase when expressed in *S. cerevisiae*.

EXAMPLE 5

Identification of Mutations in CSFAD3 Confirms Δ15-Desaturase Activity

Figure 3C:
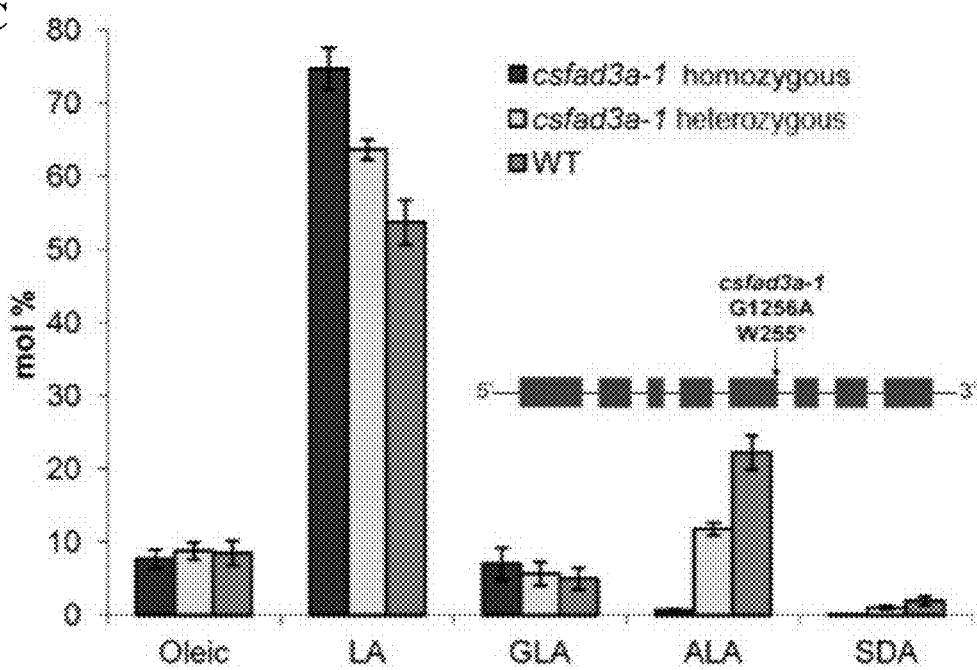
Figure 3D:
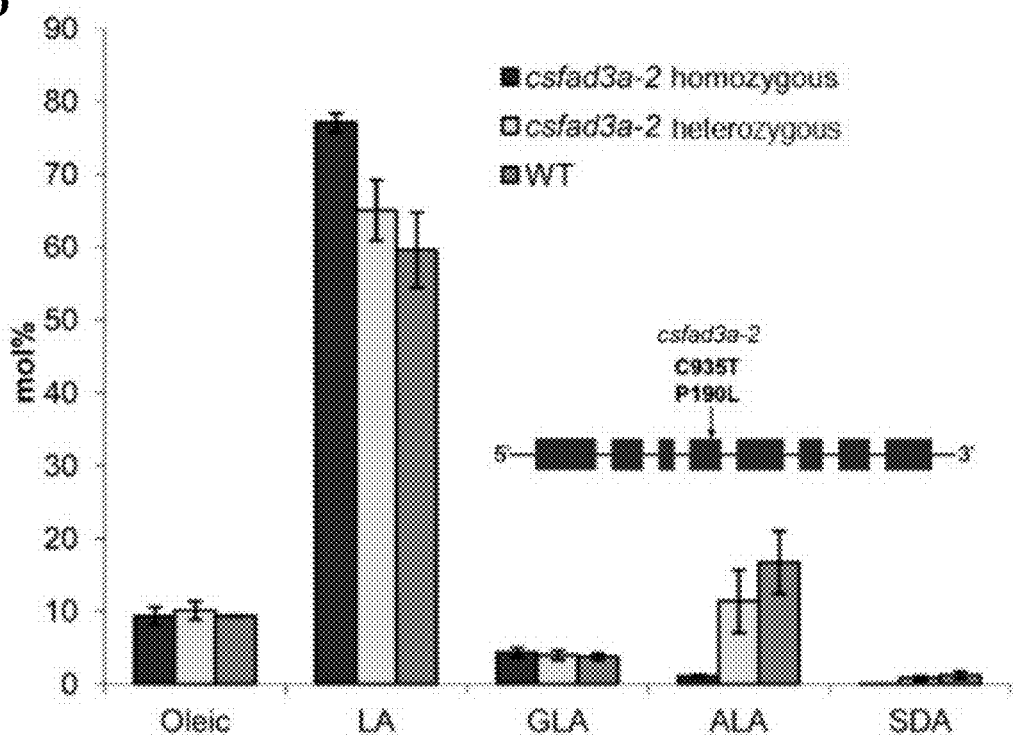

We screened our EMS mutagenized hemp population and identified an allelic series of mutations in CSFAD3 including one that results in a stop codon being introduced at codon position 255 that was designated csfad3a-1. We performed three rounds of backcrossing to Finola and obtained homozygous csfad3a-1 ($BC_3F_1$) seeds by crossing $BC_3$ siblings. Seed oil of the homozygous csfad3a-1 contained near zero and zero levels of ALA and SDA, respectively, an elevation of LA from 55 to 75 molar percent and no significant effect on GLA compared to the segregating wild type and heterozygotes in the M5 generation (FIG. 3C, Table 2). A similar seed oil phenotype was seen in $BC_2F_1$ material (Table 2). These dramatic changes in the homozygous csfad3a-1 seed oil profile confirmed that CSFAD3A acts as a Δ15-desaturase in-vivo as well as in a heterologous host. Interestingly, when the mutation is in the heterozygous state, an intermediate phenotype is displayed in the seed oil with just half the levels of ALA and SDA compared to wild type. A second mutant, csfad3a-2, carried a point mutation resulting in conversion of proline to leucine at amino acid position 190 and this resulted in a similar seed oil phenotype to csfad3a-1 (FIG. 3D, Table 2). In contrast with seed oil, production of ALA in the leaf tissue of both csfad3a-1 and csfad3a-2 is decreased by only 6 and 7% respectively compared to wild type (Table 3). This suggests the expression of other genes encoding Δ15-desaturase enzymes in leaf tissue with CSFAD3B and CSFAD3C being obvious candidates.

EXAMPLE 6

High Oleic Hemp Oil Product Performance

Figure 5A:
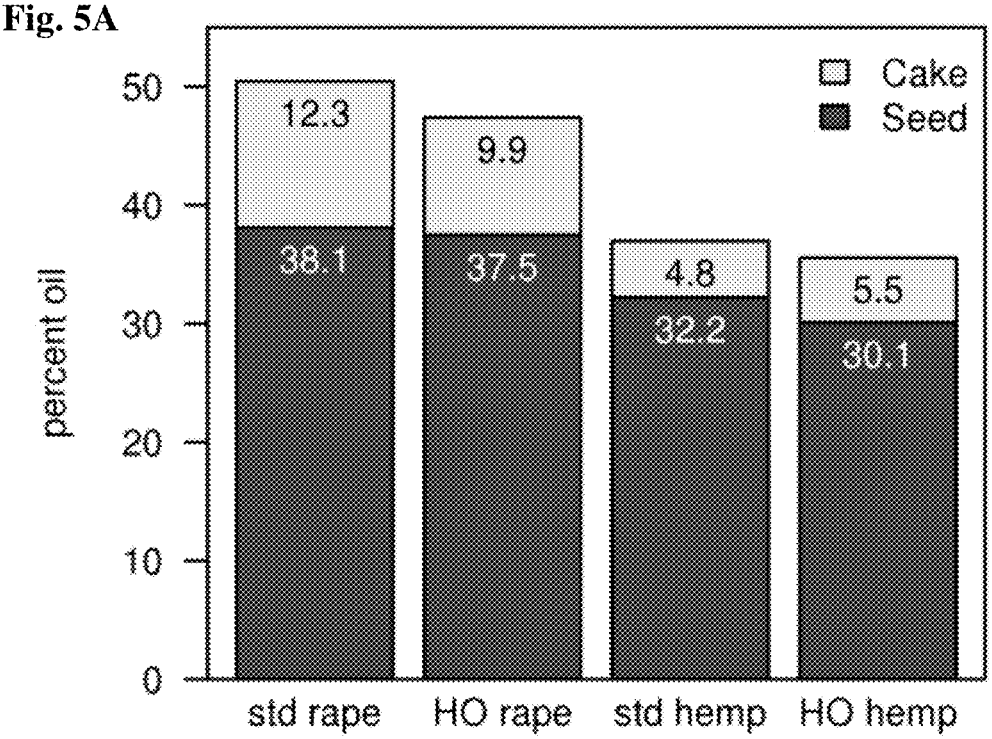
FIGS. 5A-5D Cold-pressed oil analyses from standard (std) or high oleic (HO) hempseed and rapeseed. Small batches of seed harvested from field plots (~150 g) were cold-pressed and analysed for total oil content in the cake and seed (A), relative distribution of fatty acids (B) and rancimat-assayed stability at three different temperatures (C). Tocopherol assays are shown for hemp seed only (D). All data are representative assay values taken from the second or third pressed oil batches after the press had been preconditioned with appropriate seed and reached uniform operating temperatures. For tocopherol analyses (D), values are means±1 standard error from five analyses from the same oil batches with letters above bars indicating significantly different groups (ANOVA and Tukey's HSD; $P<0.05$)
Figure 5B:
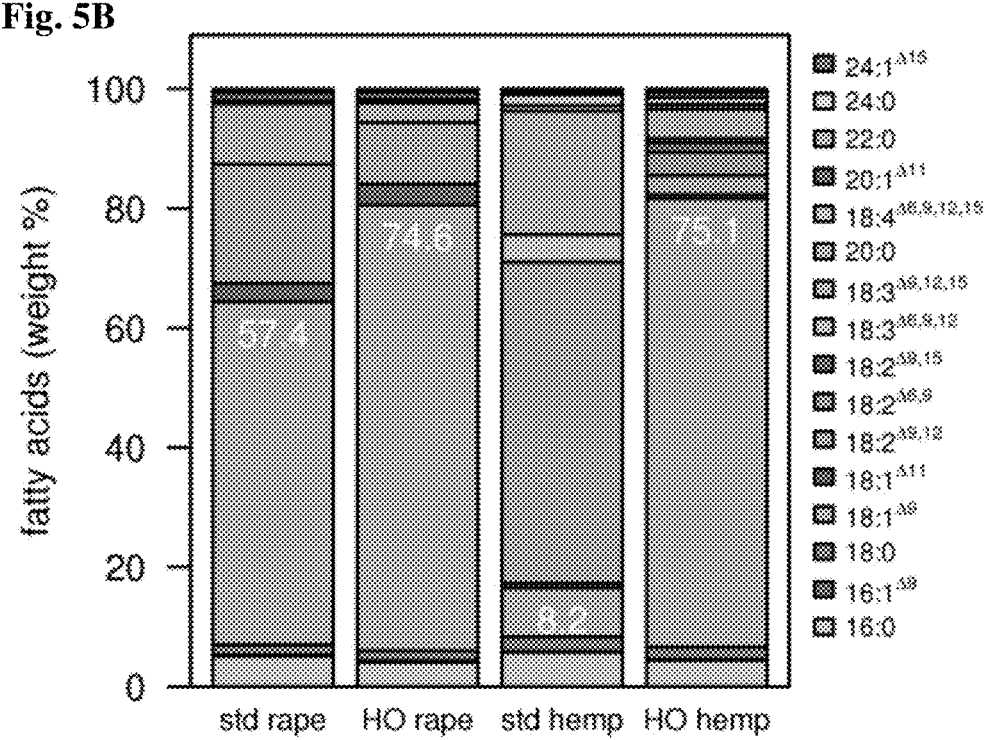
Figure 5C:
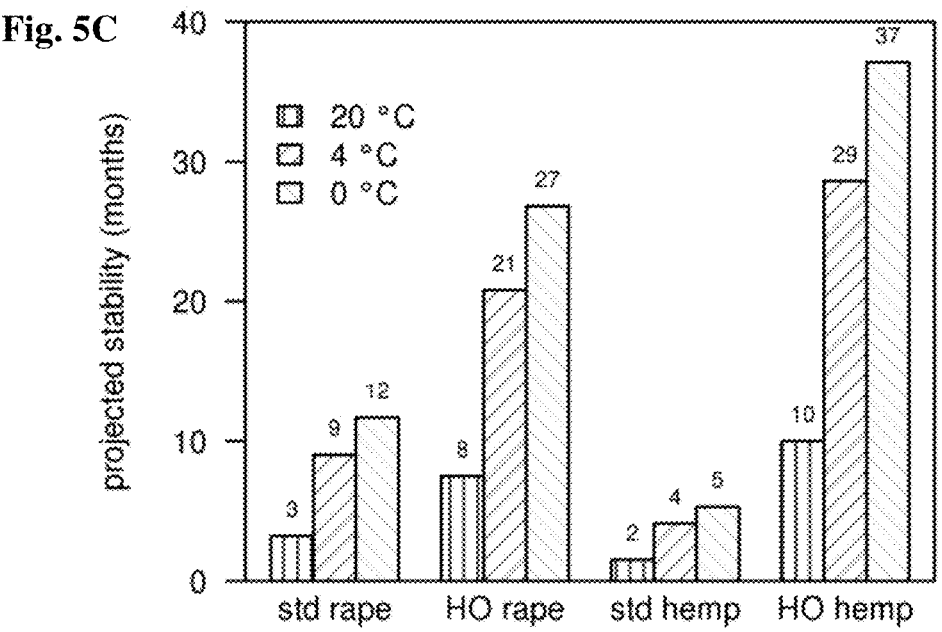
Figure 5D:
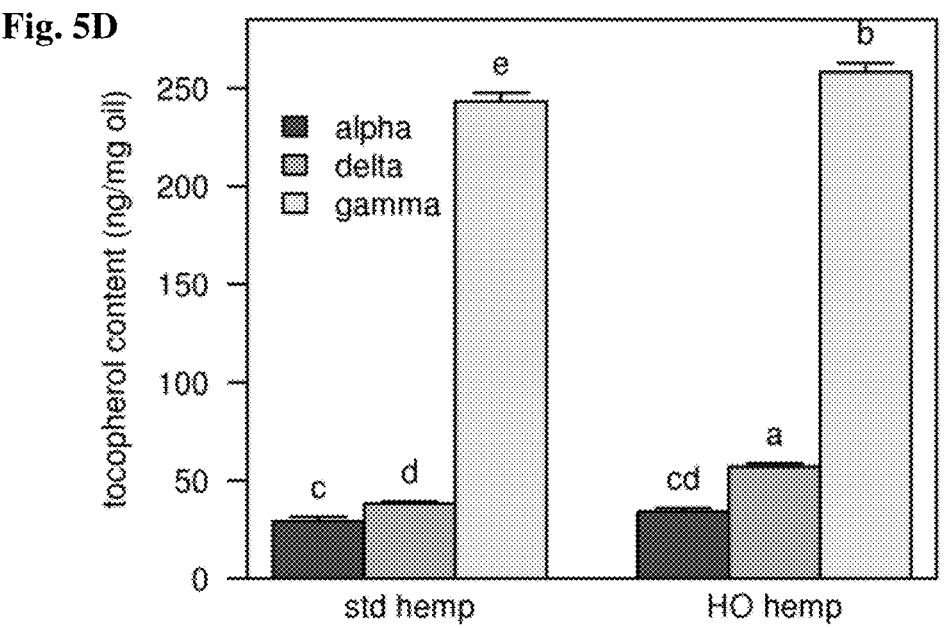
Figure 9:
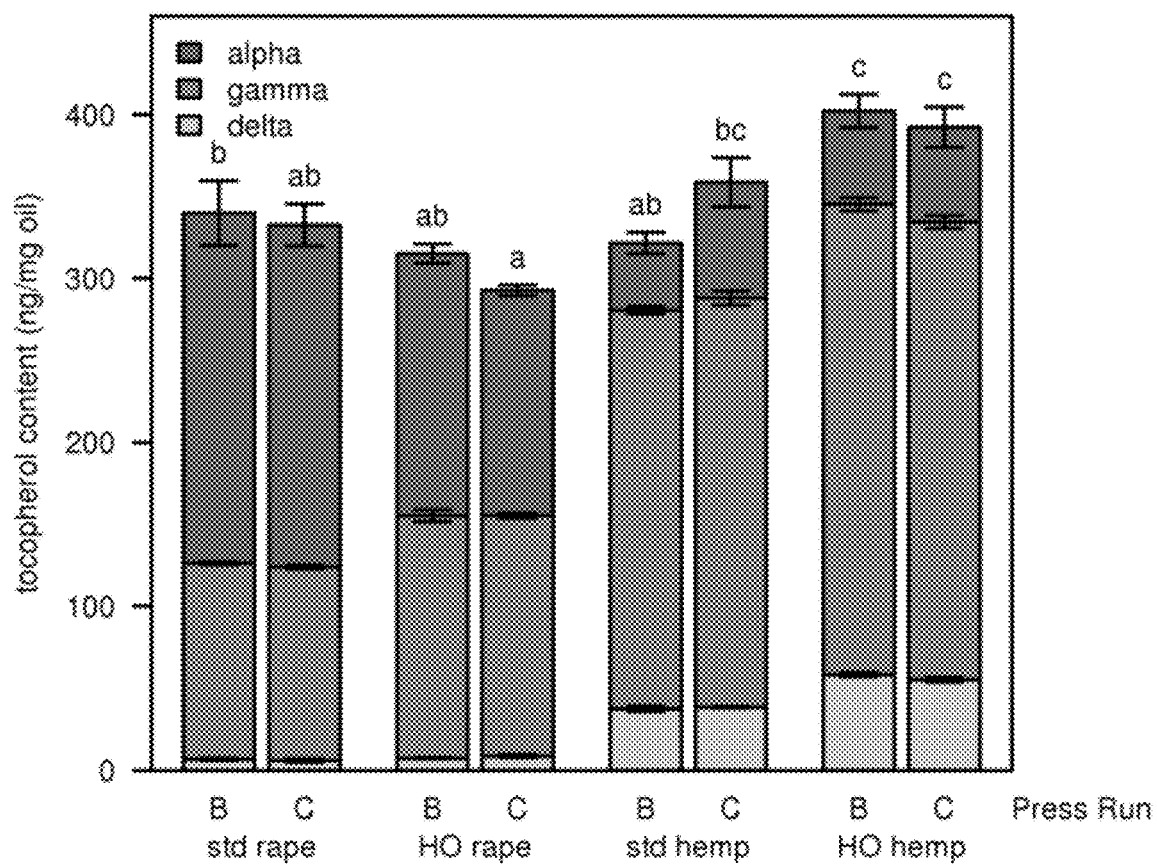
FIG. 9. Comparison of tocopherol content in standard and high oleic rapeseed and hemp seed oil; Oil from second and third press runs (B and C on graph, respectively) were analysed as per FIG. 5.
Figure 10:
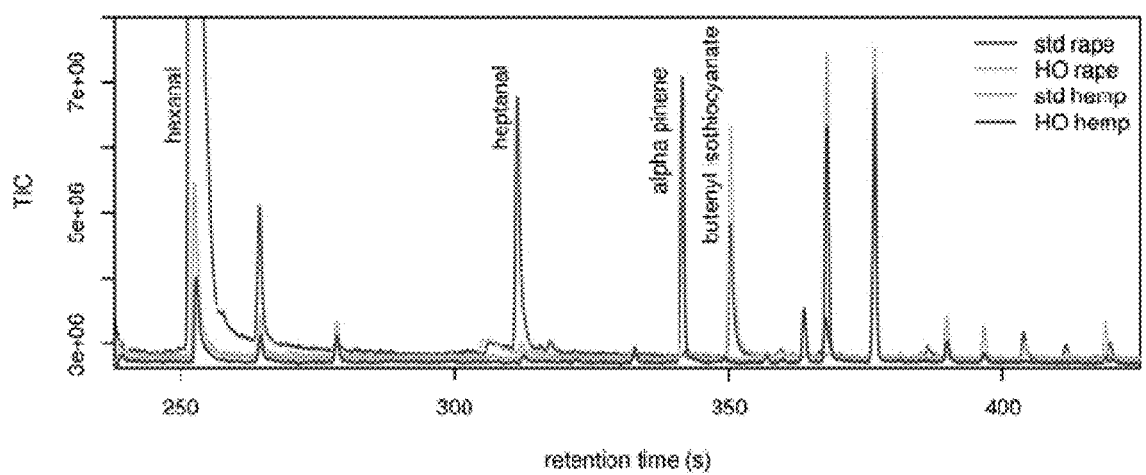
FIG. 10. Comparison of small molecule volatiles emitted from standard and high oleic rapeseed and hemp seed oil; Volatiles were analysed by SPME of headspace above cold-pressed oil samples followed by separation and detection by GCMS. Representative traces are shown with major peaks identified by reference to authentic standards (hexanal, heptanal, alpha pinene) or to the NIST 05 mass spectral library (butenyl isothiocyanate)
Figure 11:
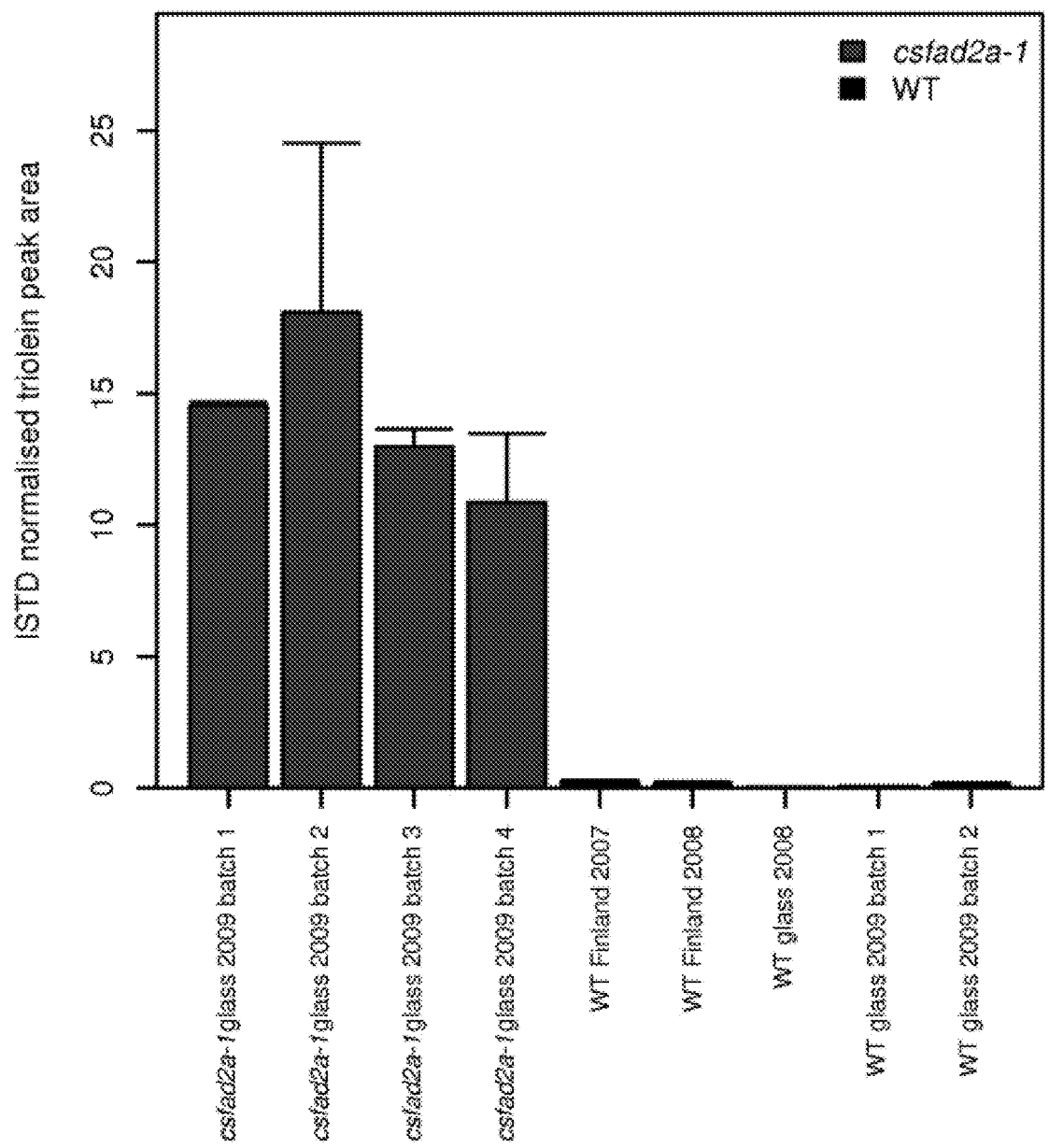
FIG. 11. Triacylglycerol analysis reveals that triolein accumulates in High Oleic Hemp seed and is absent in WT seed. Single seeds were harvested from mutant or wild type plants grown under glass or in the field over different seasons. These were analyzed for triacylglycerol content by LCMS. Results are means±1 standard error for n=5 analyses.
Figure 16:
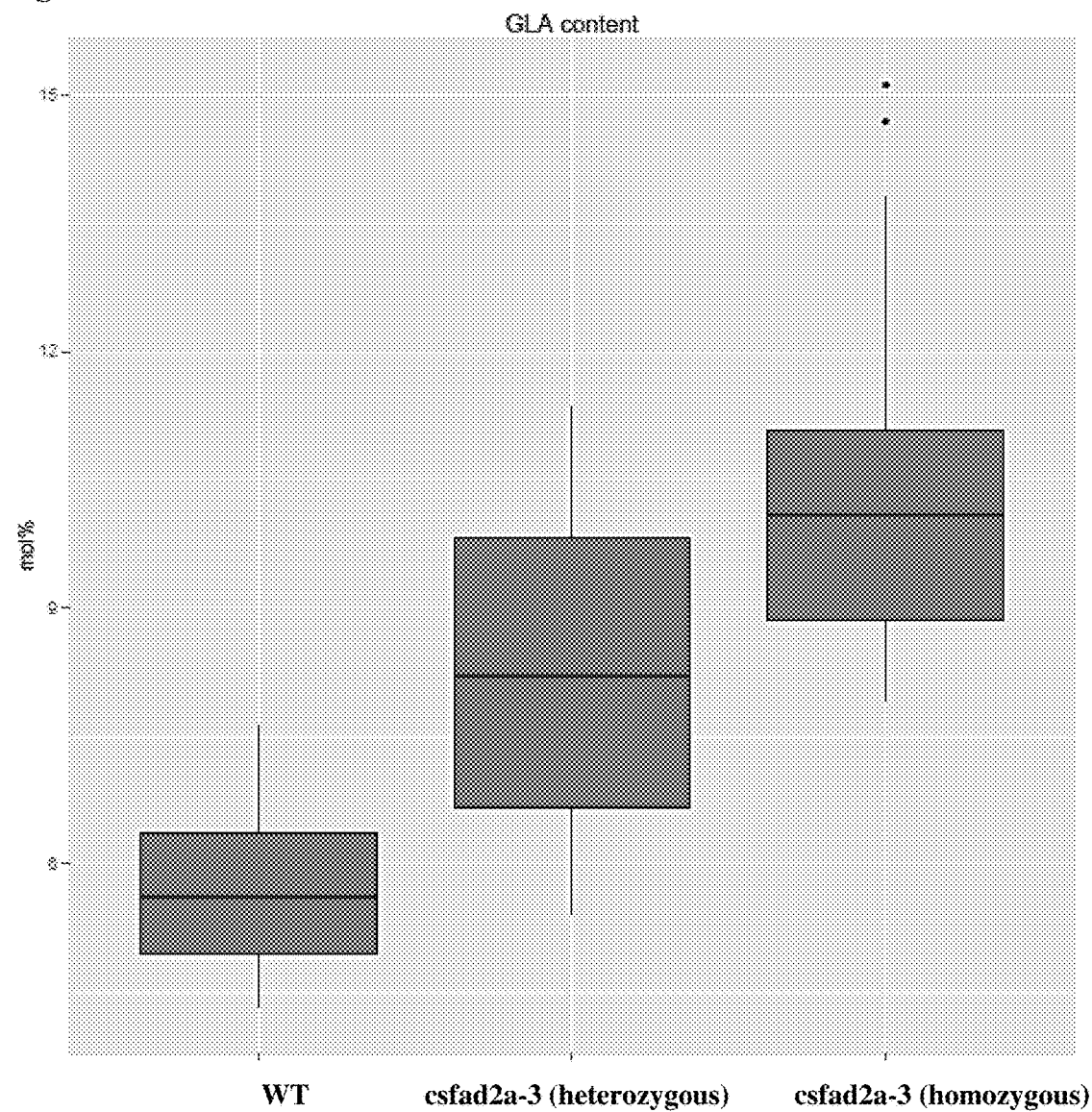
FIG. 16: A boxplot depiction of molar percent GLA in oil from individual seeds from a wild type (WT), heterozygous and homozygous csfad2a-3 mutant. This analysis demonstrates a significant increase in GLA content in seed oil from the homozygous mutant seed material compared to wild type with the heterozygote showing a GLA content inter diary between WT and homozygous mutant.

We selected csfad2a-1 for further analysis and extended the backcrossing to generate $BC_4$ material and csfad2a-1 seed was bulked up by crossing homozygous mutant siblings. This material, that we now refer to as 'High Oleic Hemp' was grown in a single block field trial in Yorkshire, UK during the 2011 growing season. Overall plant growth habit, flowering time and seed yield per plant were similar to the Finola wild type. Seed was cold pressed giving a percentage oil of approximately 36% in the wild type and csfad2a-1 material (FIG. 5A). Fatty acid composition analysis confirmed the high oleic status of the cold pressed field grown csfad2a-1 material confirming it to be on a par with a commercial High Oleic rapeseed material (FIG. 5B). Rancimat determination of oxidation stability of the pressed oil is an industry standard methodology that allows shelf life to be determined by extrapolation of oxidation at elevated temperatures. We found that our High Oleic Hemp csfad2a-1 oil had an increased shelf life from 1.5 to 10 months at 20° C., 4.1 to 28.6 months at 4° C. and 5.3 to 37.1 at 0° C. (FIG. 5C). Shelf Life of High Oleic Rapeseed Oil is also longer than standard rapeseed oil (FIG. 5C) but shelf life of the High Oleic Hemp exceeds that calculated for high oleic rapeseed oil despite them having equivalent amounts of oleic and polyunsaturated fatty acids (FIGS. 5B and 5C). Plant seeds contain antioxidants such as tocopherols, which are thought to play a role in preventing oxidation of polyunsaturated fatty acids. We measured levels of tocopherols in our High Oleic Hemp Oil and found these to be significantly higher than that present in Finola hemp oil (FIG. 5D) and also significantly higher than in both standard rapeseed oil and High Oleic Rapeseed Oil (FIG. 9). Consistent with the increased stability of the High Oleic Hemp and Rapeseed oils we found that they produced decreased levels of volatile aldehydes as determined by head space analysis (FIG. 10). Not surprisingly, the High Oleic Hemp TAG composition consisted mainly of triolein which was completely absent from Finola hemp oil (FIG. 11).

EXAMPLE 7

Figure 4B:
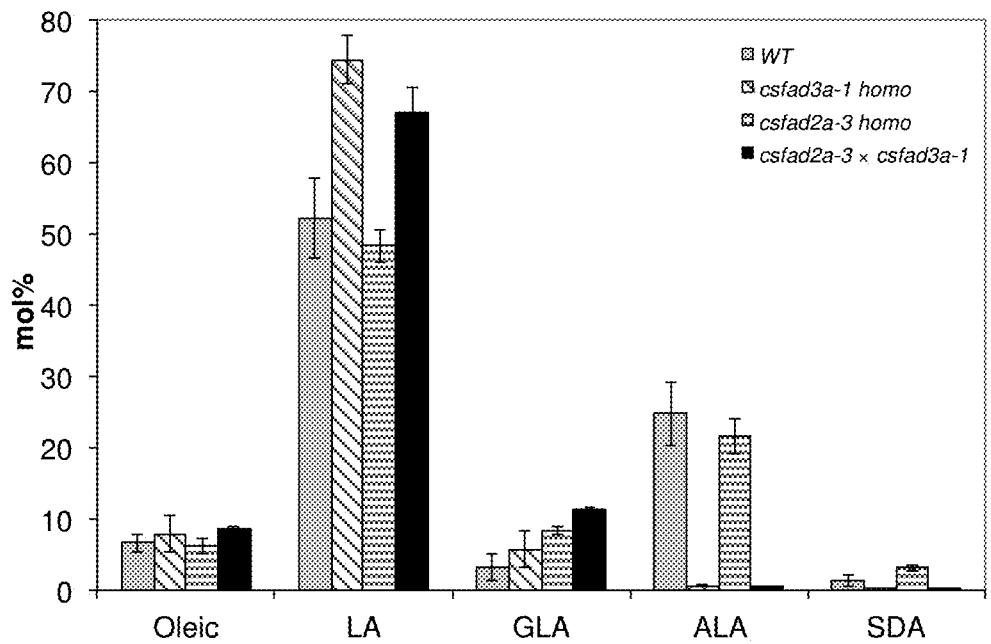

Breeding and Seed Oil Characterisation of a csfad2a-3×csfad3a-1 Double Mutant We obtained csfad2a-3 and csfad3a-1 double mutants by crossing heterozygous $BC_4$ csfad2a-3 plants with heterozygous csfad3a-1 $BC_4$ plants followed by sibling crosses between plants heterozygous for both alleles to yield a segregating $BC_4F_2$ population. From this segregating population wild type (CSFAD2a-3 and CSFAD3a-1), csfad2a-3 (and null for csfad3a-1), csfad3a-1 (null for csfad2a-3) and csfad2a-3×csfad3a-1 double homozygous plants were selected and for each class sibling crosses set up. The resulting $BC_4F_3$ seed were used for fatty acid profiling (FIG. 4B, Table 2). The GLA content of seed of homozygous csfad2a-3×csfad3a-1 double mutant plants reached up to 11.7 molar % and is thus higher than that found in the seed of homozygous csfad2a-3 and the csfad3a-1 single mutant plants originating from the same population (FIG. 4B, Table 2). The ALA content was markedly reduced (0.5 molar %) in the double mutant and identical to that found in homozygous csfad3a-1 single mutants. Although LA content increased in the double mutant (67 molar %) compared to wild type plants originating from the same population it was lower than the LA content found in csfad3a-1 single mutants (74 molar %, FIG. 4B, Table 2). This suggests that a proportion of the LA accumulating as the result of the csfad3a-1 allele is partitioned towards increased GLA synthesis in the homozygous presence of the csfad2a-3 high GLA allele. Taken together the fatty acid profiling reveal that combining the single mutant allele phenotypes of csfad3a-1 and the csfad2a-3 leads to a further increase in GLA seed oil content.

EXAMPLE 8

GLA Content in Seed Oil from Heterozygous and Homozygous csfad2a-3 and Wild Type (WT)

In order to generate seeds of the desired genotype, the WT and homozygous csfad2a-3 plants were grown in parallel and then the following crossing strategy was undertaken:

To obtain csfad2a-3 homozygous seeds: male (M) and female (F) homozygous csfad2a-3 parental material was crossed (in 3 independent crosses);

To obtain heterozygous seeds for the csfad2a-3 allele: male homozygous csfad2a-3 parental lines (M) were crossed with female WT (F) and alternatively male WT (M) parental lines were crossed with female homozygous csfad2a-3 parental material (F). WT seed were produced at the same time by crossing wild type male and female parents. Replicates of all above crosses were performed.

At least five, randomly selected, mature seeds descending from each cross were weighed and sampled individually for fatty acid composition analysis. This was performed by standard Gas Chromatography analysis of fatty acid methyl esters.

The results demonstrate that levels of GLA are significantly higher in the csfad2a-3 mutant seed material compared to wild type. Levels of GLA in heterozygous csfad2a-3 seed material is intermediate between that of the homozygous mutant and the wild type suggesting that the mutant allele is semi-dominant, consistent with a biochemical modification of the protein that results in an increased flux of fatty acids into GLA when the mutant form of the protein is present in the cell.

REFERENCES

Baud S, Boutin J P, Miguel M, Lepiniec L, Rochat C (2002) An integrated overview of seed development in *Arabidopsis thaliana* ecotype WS. Plant Physiology and Biochemistry 40: 151-160

Browse J, McCourt P J, Somerville C R (1986) Fatty acid composition of leaf lipids determined after combined digestion and fatty acid methyl ester formation from fresh tissue Anal Biochem 152: 141-145

Callaway J (2004) Hempseed as a nutritional resource: an overview. Euphytica 140: 65-72

Callaway J C, Laakkonen T T (1996) Cultivation of *Cannabis* oil seed varieties in Finland. Journal of the International Hemp Association 3: 32-34

Christie W W, Brechany E Y, Holman R T (1987) Mass spectra of the picolinyl esters of isomeric mono- and dienoic fatty acids. Lipids 22: 224-228.

de Gyves E M, Sparks C A, Sayanova O, Lazzeri P, Napier J A, Jones H D (2004) Genetic manipulation of γ-linolenic acid (GLA) synthesis in a commercial variety of evening primrose (*Oenothera* sp.). Plant Biotechnology Journal 2: 351-357

Dubois N, Barthomeuf C, Berge J-P (2006) Convenient preparation of picolinyl derivatives from fatty acid esters. Eur J Lipid Sci Technol 108: 28-32

Felsenstein J (1989) PHYLIP—Phylogeny inference package (Version 3.2). Cladistics 5: 164-166

Gietz R D, Woods R A (2002) Transformation of yeast by lithium acetate/single-stranded carrier DNA/polyethylene glycol method. In G Christine, RF Gerald, eds, Methods in Enzymology, Vol 350. Academic Press, pp 87-96

Graham I A, Besser K, Blumer S, Branigan C A, Czechowski T, Elias L, Guterman I, Harvey D, Isaac P G, Khan A M, Larson T R, Li Y, Pawson T, Penfield T, Rae A M, Rathbone D A, Reid S, Ross J, Smallwood M F, Segura V, Townsend T, Vyas D, Winzer T, Bowles D (2010) The Genetic Map of *Artemisia annua* L. Identifies Loci Affecting Yield of the Antimalarial Drug Artemisinin. Science 327: 328-331

Hitz W D, Carlson T J, Booth J R J, Kinney A J, Stecca K L, Yadav N S (1994) Cloning of a higher-plant plastid ω-6 fatty acid desaturase cDNA and its expression in a cyanobacterium. Plant Physiol 105: 635-641

Hong H, Datla N, Reed D W, Covello P S, MacKenzie S L, Qiu X (2002) High-level production of γ-linolenic acid in *Brassica juncea* using a Δ6 desaturase from *Pythium irregulare*. Plant Physiol 129: 354-362

Kinney A J (1998) Production of specialised oils for industry. In: Plant Lipid Biosynthesis: Fundamentals and Agricultural Applications. Ed. J. L. Harwood, Cambridge University Press, Cambridge (UK), pp 273-286

Lee M, Lenman M, Banas A, Bafor M, Singh S, Schweizer M, Nilsson R, Liljenberg C, Dahlqvist A, Gummeson P-O, Sjodahl S, Green A, Stymne S (1998) Identification of non-heme diiron proteins that catalyze triple bond and epoxy group formation. Science 280: 915-918

Li H, Durbin R (2009) Fast and accurate short read alignment with Burrows-Wheeler transform. Bioinformatics 25: 1754-1760

Li H-L (1974) An archaeological and historical account of *cannabis* in China. Econ Bot 28: 437-448

Liu J-W, Huang Y-S, DeMichele S, Bergana M, Bobik E, Hastilow C, Chuang L-T, Mukerji P, Knutzon D (2001) Evaluation of the seed oils from a canola plant genetically transformed to produce high level of γ-linolenic acid. In Huang Y-S, Ziboh A eds, γ-Linolenic Acid: Recent Advances in Biotechnology and Clinical Applications, AOCS Press, Champaign, Ill., pp 61-71

Ohlrogge J, Browse J (1995) Lipid biosynthesis. Plant Cell 7: 957-970

Ramakers C, Ruijter J M, Deprez R H L, Moorman A F M (2003) Assumption-free analysis of quantitative real-time polymerase chain reaction (PCR) data. Neurosci Lett 339: 62-66

Reddy A S, Thomas T L (1996) Expression of a cyanobacterial Δ6-desaturase gene results in γ-linolenic acid production in transgenic plants. Nat Biotech 14: 639-642

Reed D W, Schafer U A, Covello P S (2000) Characterization of the *Brassica napus* extraplastidial linoleate desaturase by expression in *Saccharomyces cerevisiae*. Plant Physiol 122: 715-720

Ruijter J M, Ramakers C, Hoogaars W M H, Karlen Y, Bakker O, van den Hoff M J B, Moorman A F M (2009) Amplification efficiency: linking baseline and bias in the analysis of quantitative PCR data. Nucleic Acids Res 37: e45

Salamov A A, Solovyev V V (2000) Ab initio Gene Finding in *Drosophila* Genomic DNA. Genome Res 10: 516-522

Sayanova O, Davies G M, Smith M A, Griffiths G, Stobart A K, Shewry P R, Napier J A (1999a) Accumulation of Δ6-unsaturated fatty acids in transgenic tobacco plants expressing a Δ6-desaturase from *Borago officinalis*. J Exp Bot 50: 1647-1652

Sayanova O, Shewry P R, Napier J A (1999b) Histidine-41 of the cytochrome b5 domain of the borage Δ6 fatty acid desaturase is essential for enzyme activity. Plant Physiol 121: 641-646

Schwartzbeck J L, Jung S, Abbott A G, Mosley E, Lewis S, Pries G L, Powell G L (2001) Endoplasmic oleoyl-PC desaturase references the second double bond. Phytochemistry 57: 643-652

Shanklin J, Cahoon E B (1998) Desaturation and related modifications of fatty acids 1. Annu Rev Plant Physiol Plant Mol Bioly 49: 611-641

Song L Y, Lu W X, Hu J, Zhang Y, Yin W B, Chen Y H, Hao S T, Wang B L, Wang R R, Hu Z M (2010) Identification and functional analysis of the genes encoding Δ6-desaturase from *Ribes nigrum*. Journal Exp Bot 61: 1827-1838

Sperling P, Heinz E (2003) Plant sphingolipids: structural diversity, biosynthesis, first genes and functions. Biochimica et Biophysica Acta (BBA)—Molecular and Cell Biology of Lipids 1632: 1-15

Thompson J D, Higgins D G, Gibson T J (1994) CLUSTAL W: improving the sensitivity of progressive multiple sequence alignment through sequence weighting, position-specific gap penalties and weight matrix choice. Nucleic Acids Res 22: 4673-4680

Till B J, Burtner C, Comai L, Henikoff S (2004) Mismatch cleavage by single-strand specific nucleases. Nucleic Acids Res 32: 2632-2641

Till B J, Zerr T, Comai L, Henikoff S (2006) A protocol for TILLING and Ecotilling in plants and animals. Nature protocols 1: 2465-2477 van Bakel H, Stout J M, Cote A G, Tallon C M, Sharpe A G, Hughes T R, Page J E (2011) The draft genome and transcriptome of *Cannabis sativa*. Genome Biology 12: R102

Vrinten P, Hu Z, Munchinsky M-A, Rowland G, Qiu X (2005) Two FAD3 desaturase genes control the level of linolenic acid in flax seed. Plant Physiol 139: 79-87

Zhang P, Burton J W, Upchurch R G, Whittle E, Shanklin J, Dewey R E (2008) Mutations in a Δ9-Stearoyl-ACP-desaturase gene are associated with enhanced stearic acid levels in soybean seeds. Crop Sci. 48: 2305-2313

Zhang D, Pirtle I L, Park S J, Nampaisansuk M, Neogi P, Wanjie S W, Pirtle R M, Chapman K D (2009) Identification and expression of a new delta-12 fatty acid desaturase (FAD2-4) gene in upland cotton and its functional expression in yeast and *Arabidopsis thaliana* plants. Plant Physiol Biochem-(Paris) 47: 462-471

The invention claimed is:

1. A modified *Cannabis* spp plant generated by mutagenesis with a chemical mutagen or physical mutagen, comprising: a modified delta-12 desaturase gene comprising a termination codon at position 167 of SEQ ID NO: 3, resulting in a truncated and non-functional delta-12 desaturase polypeptide in the modified *Cannabis* spp plant, wherein the modified delta-12 desaturase gene comprising a termination codon at position 167 of SEQ ID NO: 3 is homozygous, and wherein the modified plant has an oleic acid content of between 70-85% of the total oil content of the modified plant.

2. The modified plant of claim 1, wherein said modified plant comprises reduced linoleic add content, reduced alpha linolenic add content, reduced gamma linolenic add content, or combinations thereof, as compared to a wild-type plant.

3. The modified plant of claim 1, wherein said modified plant has a gamma linolenic acid content 5-15% of the total oil content of the modified plant.

4. The modified plant of claim 1, wherein the delta-12 desaturase gene is modified by a chemical mutagen comprising a base analogue, deaminating agent, DNA intercalating agent, alkylating agent, transposon, bromine, or sodium azide.

5. The modified plant of claim 1, wherein the delta-12 desaturase gene is modified by a physical mutagen comprising ionizing radiation or psoralen exposure combined with ultraviolet irradiation.

6. The modified plant of claim 1, wherein the *Cannabis* species is *Cannabis sativa*.

7. A modified *Cannabis* spp plant generated by mutagenesis with a chemical mutagen or physical mutagen, comprising: a modified delta-12 desaturase gene comprising amino add substitutions at serine 218 and serine 375 of SEQ ID NO: 3 with proline, resulting in the modified *Cannabis* spp plant wherein the modified delta-12 desaturase gene comprising amino acid substitutions at serine 218 and serine 375 of SEQ ID between 70-85% of the total oil content of the modified plant.

8. The modified plant of claim 7, wherein said modified plant comprises reduced linoleic acid content, reduced alpha linolenic acid content, reduced gamma linolenic add content, or combinations thereof, as compared to a wild-type plant.

9. The modified plant of claim 7, wherein said modified plant has a gamma linolenic acid content 5-15% of the total oil content of the modified plant.

10. The modified plant of claim 7, wherein the delta-12 desaturase gene is modified by a chemical mutagen comprising a base analogue, deaminating agent, DNA intercalating agent, alkylating agent, transposon, bromine, or sodium azide.

11. The modified plant of claim 7, wherein the delta-12 desaturase gene is modified by a physical mutagen comprising ionizing radiation or psoralen exposure combined with ultraviolet irradiation.

12. The modified plant of claim 7, wherein the *Cannabis* species is *Cannabis sativa*.

* * * * *